United States Patent [19]

Cox, Jr. et al.

[11] 4,044,240
[45] Aug. 23, 1977

[54] TOMOGRAPHY SYSTEM HAVING AN ULTRA HIGH SPEED PROCESSING UNIT

[75] Inventors: Jerome P. Cox, Jr., St. Louis; Vernon W. Gerth, Jr., Kirkwood, both of Mo.

[73] Assignee: Picker Corporation, Cleveland, Ohio

[21] Appl. No.: 635,953

[22] Filed: Nov. 28, 1975

[51] Int. Cl.² .................. G01T 1/16; G06F 15/52
[52] U.S. Cl. .................. 235/151.3; 364/300; 250/445 T; 250/369
[58] Field of Search .......... 235/151.3; 444/1; 250/369, 336, 362, 363, 445, 445 T

[56] References Cited

U.S. PATENT DOCUMENTS

| | | | |
|---|---|---|---|
| 3,684,886 | 8/1972 | Muehllegner | 250/445 T X |
| 3,743,843 | 7/1973 | Reser | 250/320 |
| 3,784,820 | 1/1974 | Miraldi | 250/362 |
| 3,793,520 | 2/1974 | Grenier | 250/363 S |
| 3,831,032 | 8/1974 | Putod | 250/445 T |
| 3,852,603 | 12/1974 | Muehllehner | 250/445 T X |
| 3,852,611 | 12/1974 | Cesar | 250/445 T |
| 3,878,373 | 4/1975 | Blum | 250/303 X |
| 3,924,131 | 12/1975 | Hounsfield | 250/445 T X |
| 3,936,636 | 2/1976 | Percival | 250/369 X |
| 3,946,234 | 3/1976 | Hounsfield | 250/445 T X |

*Primary Examiner*—Edward J. Wise
*Attorney, Agent, or Firm*—Watts, Hoffmann, Fisher & Heinke Co.

[57] ABSTRACT

A transverse section tomography system has an ultra-high-speed data processing unit for performing back projection and updating. An X-ray scanner directs X-ray beams through a planar section of a subject from a sequence of orientations and positions. The scanner includes a movably supported radiation detector for detecting the intensity of the beams of radiation after they pass through the subject. The detector generates a series of scan data signals representative of the detected intensities. The data processing unit is coupled to the scanner and operates on the scan data signals to produce a set of filtered scan data signals representative of the contribution of each of the scan data signals towards reconstructing an image of the planar section of the subject.

The data processing unit includes a scan storage section for retrievably storing the filtered scan signals in scan storage locations corresponding to predetermined beam orientations. An array storage section is provided for storing image signals as they are generated. The image signals are stored in array storage locations coordinated with a preselected array of points of the planar section. The image signals are each successively updated to eventually represent the density of the planar section at each of the selected array of points. The processing unit also includes array storage and scan storage address calculators. The array storage address calculator determines, on a row-by-row basis, the addresses of the array storage locations corresponding to points of the planar section. The scan storage address calculator calculates the addresses of the scan storage locations containing the filtered scan signals which contribute to the reconstruction of the image at the points determined by the array storage address calculator. A reconstruction updating unit is provided for combining the addressed filtered scan signal with the addressed image signal to provide the updated image signal. According to one feature, a control unit is provided for operating the scan storage address calculator concurrently with the array storage address calculator for minimizing overall data processing time. According to another feature, the array storage section is equipped with addressing and data transfer circuitry which is operated concurrently with at least one of the address calculators for writing the updated image signal into the appropriate array storage location.

27 Claims, 56 Drawing Figures

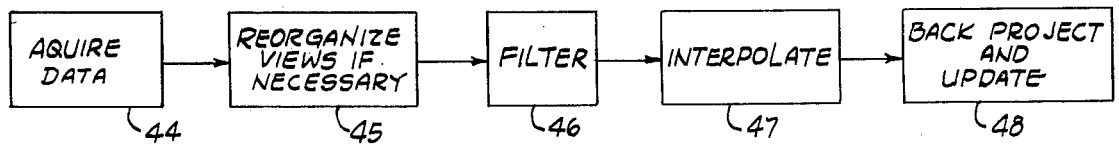
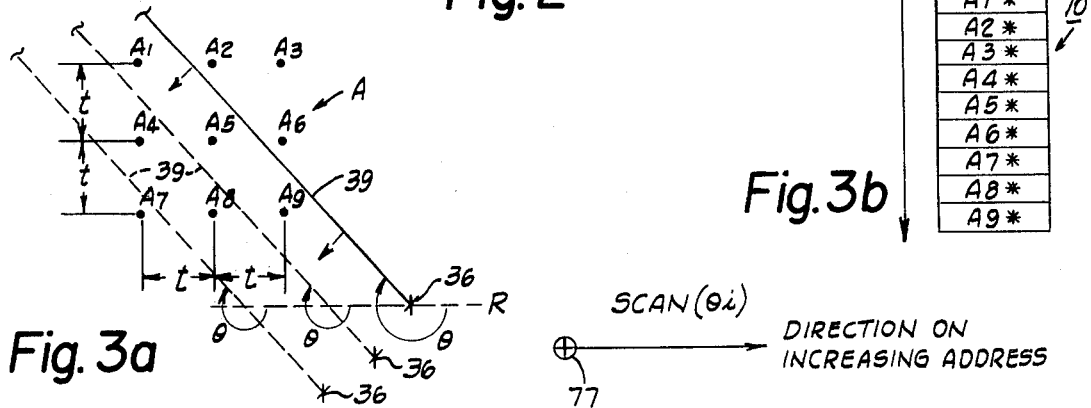
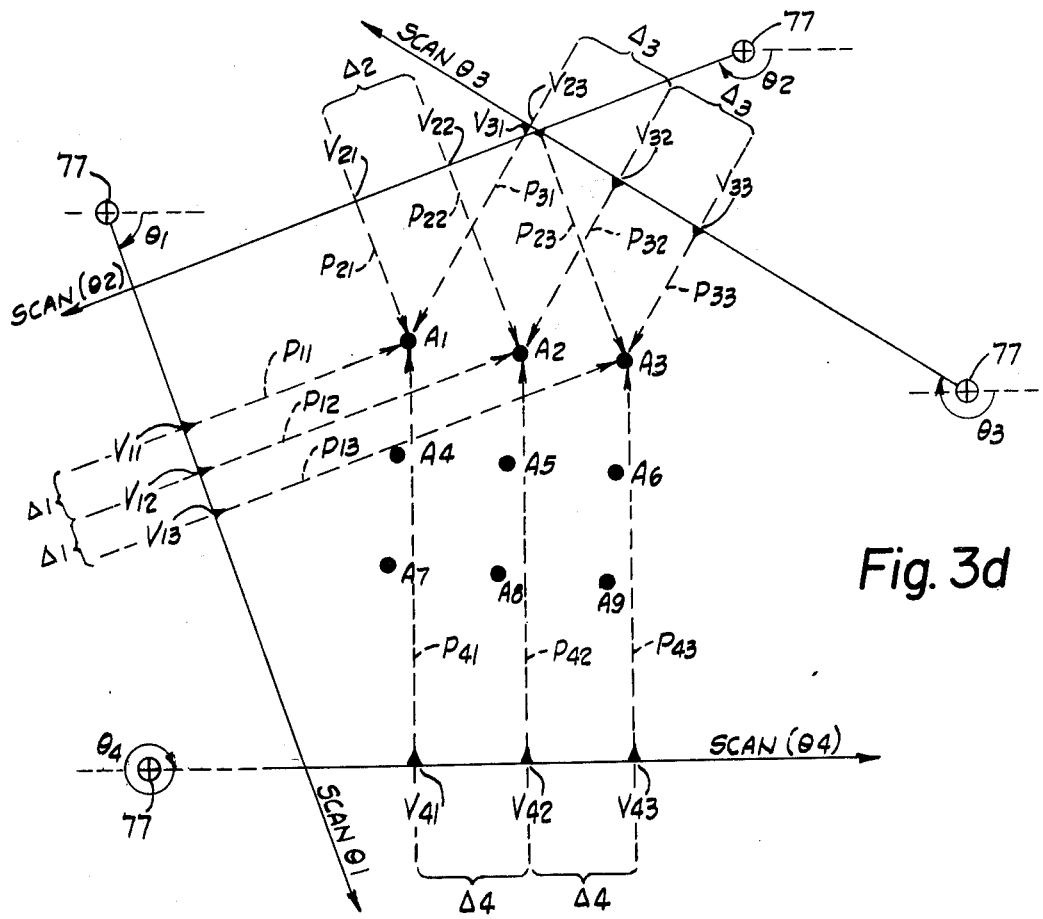

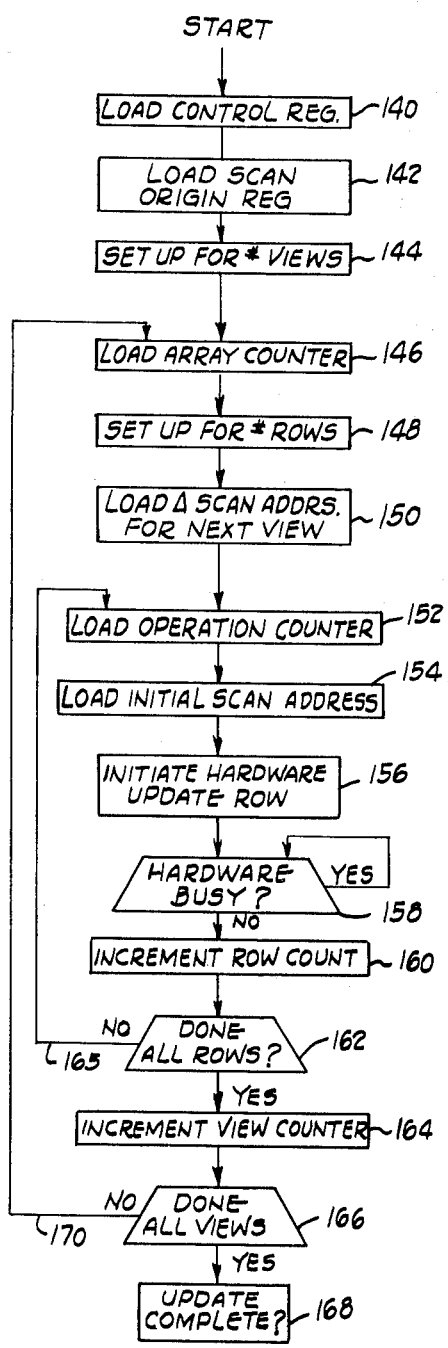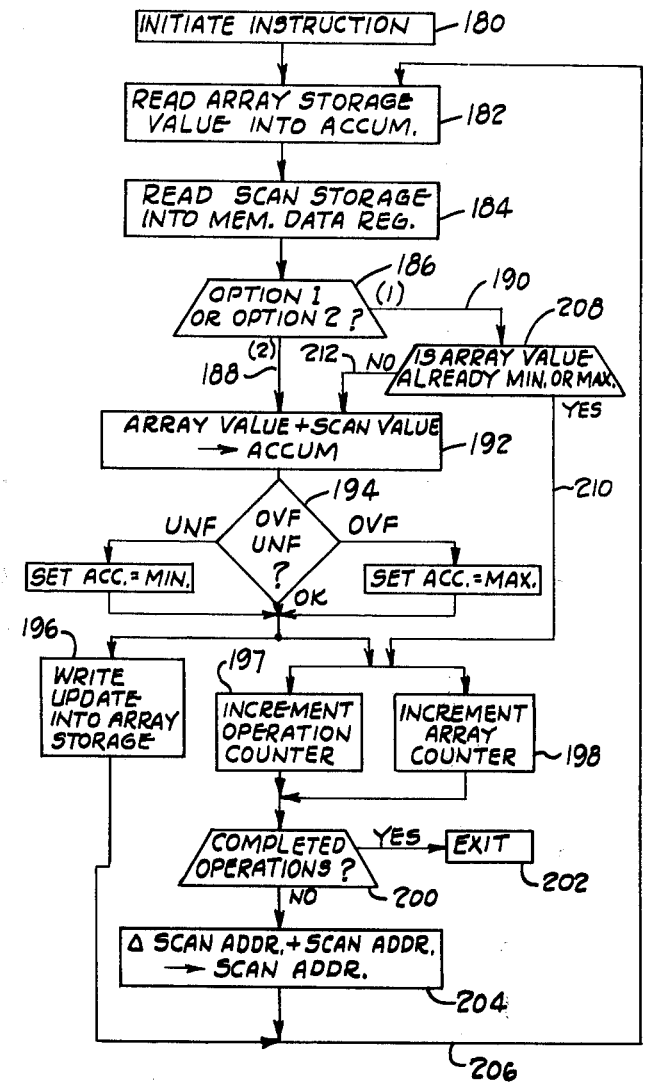
Fig. 6
Fig. 5

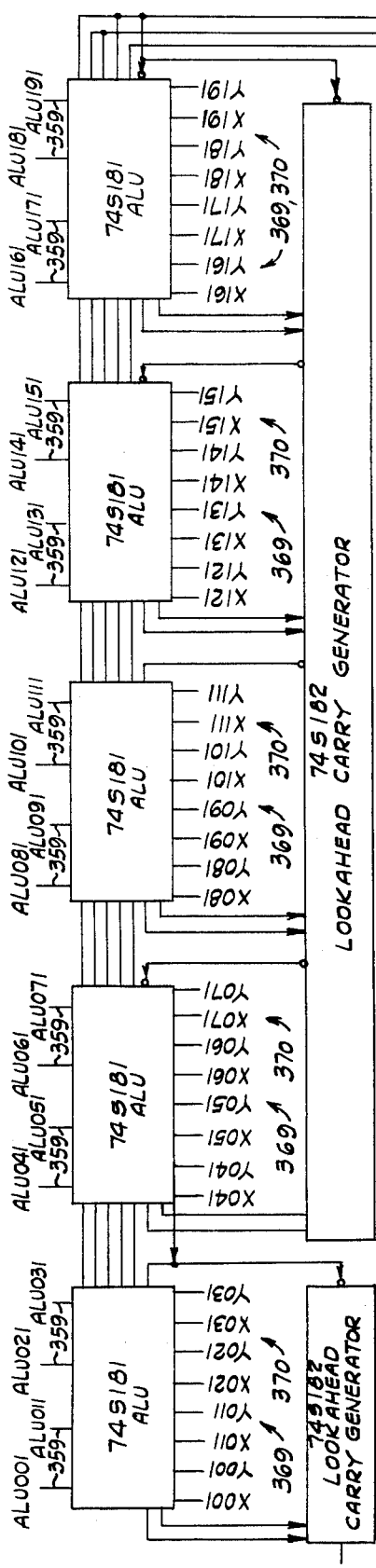
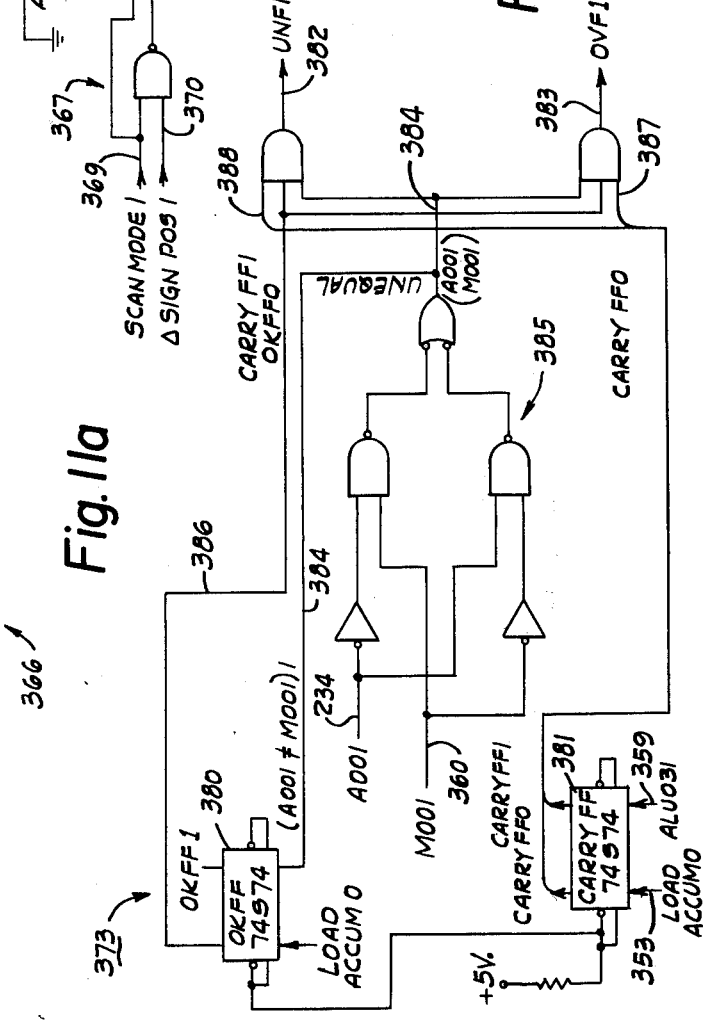
Fig. 11a
Fig. 11b

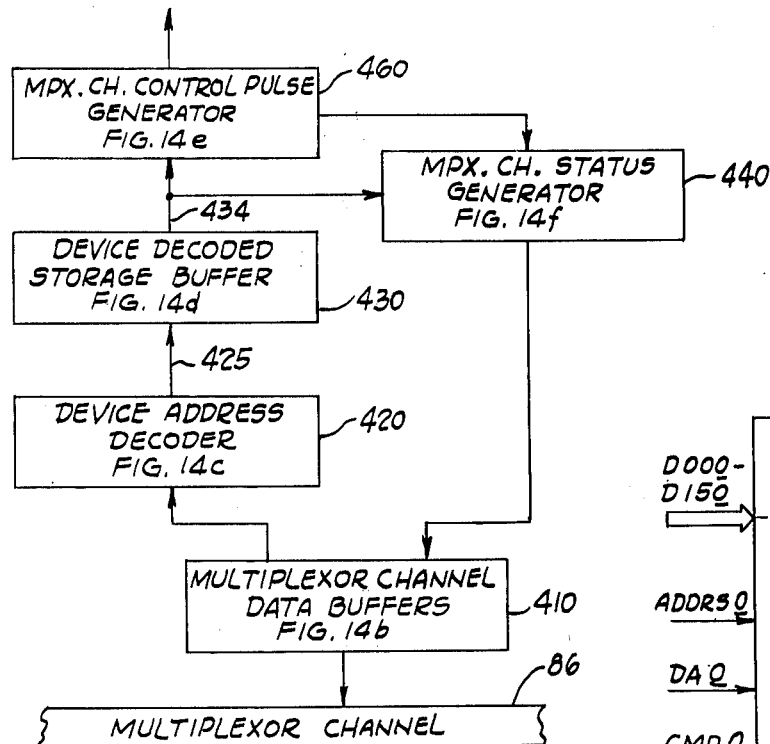
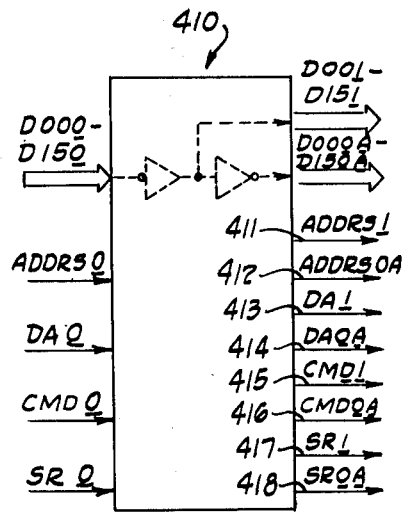
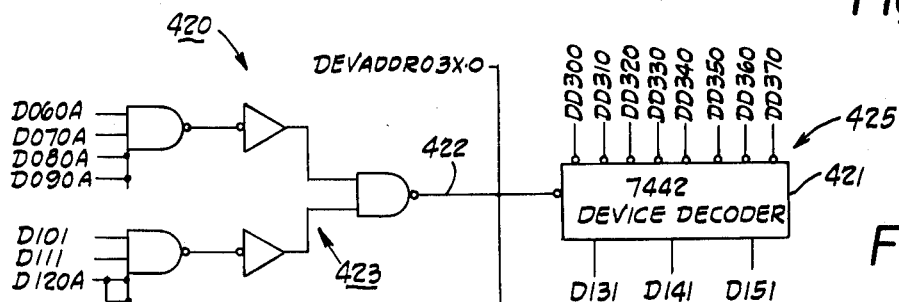
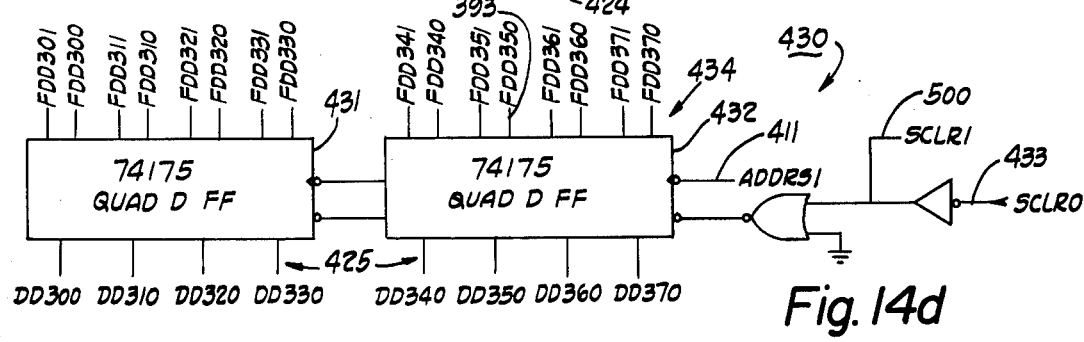

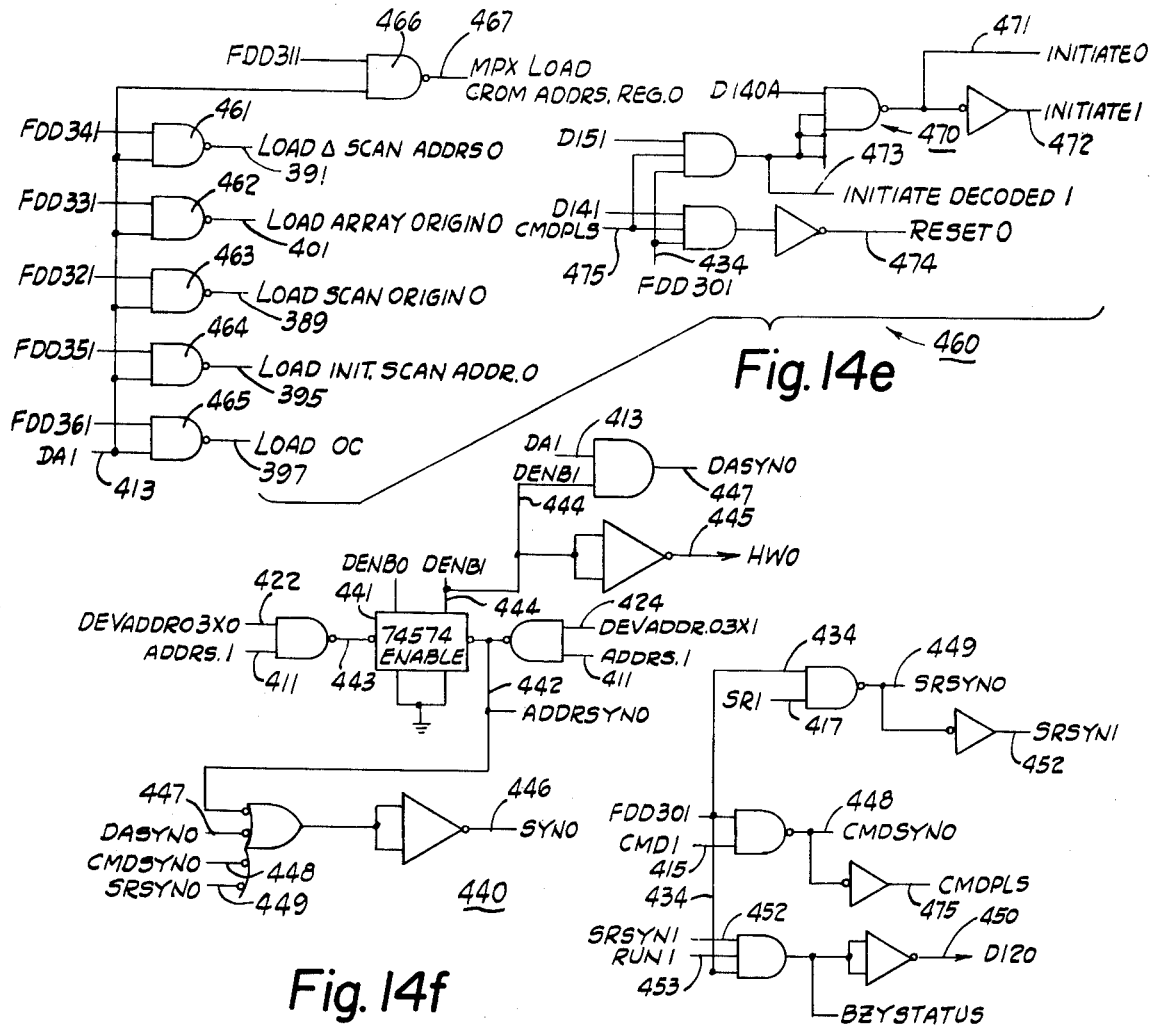
Fig. 14e
Fig. 14f
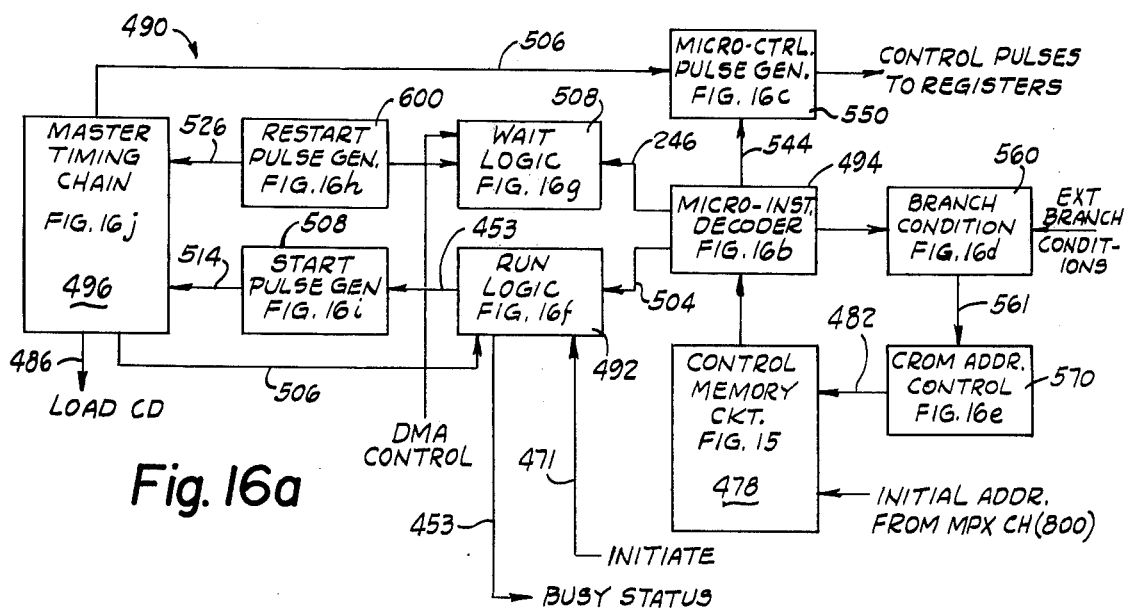
Fig. 16a

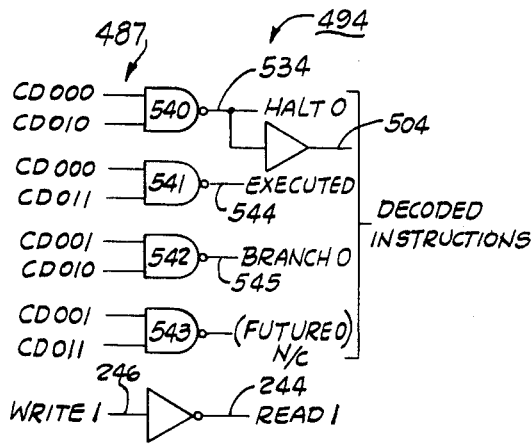
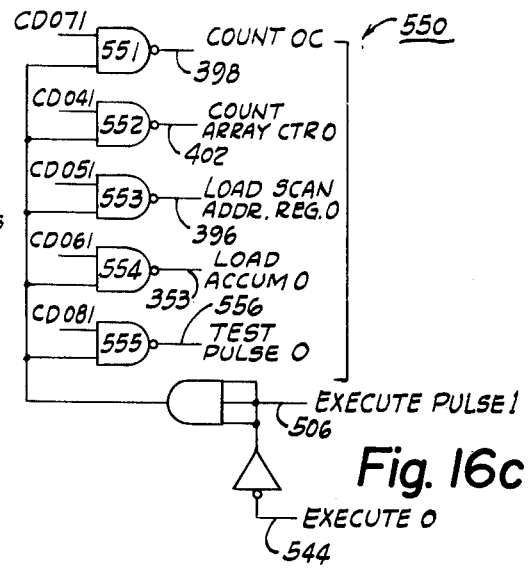
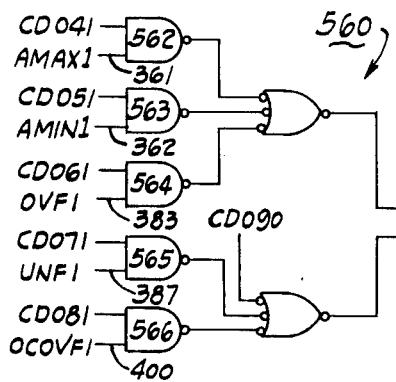
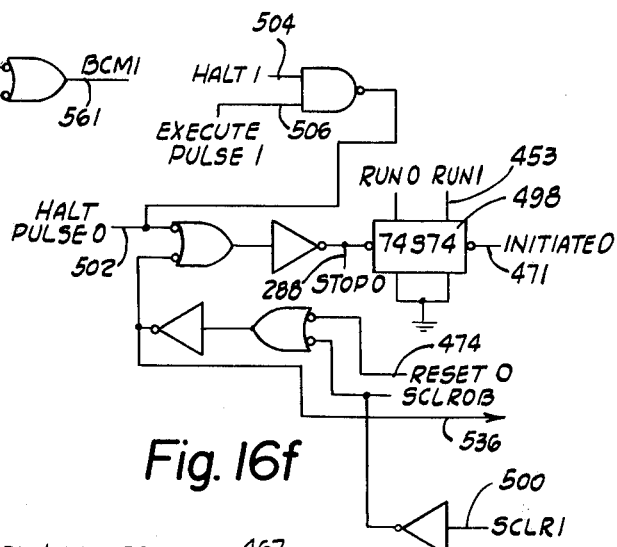
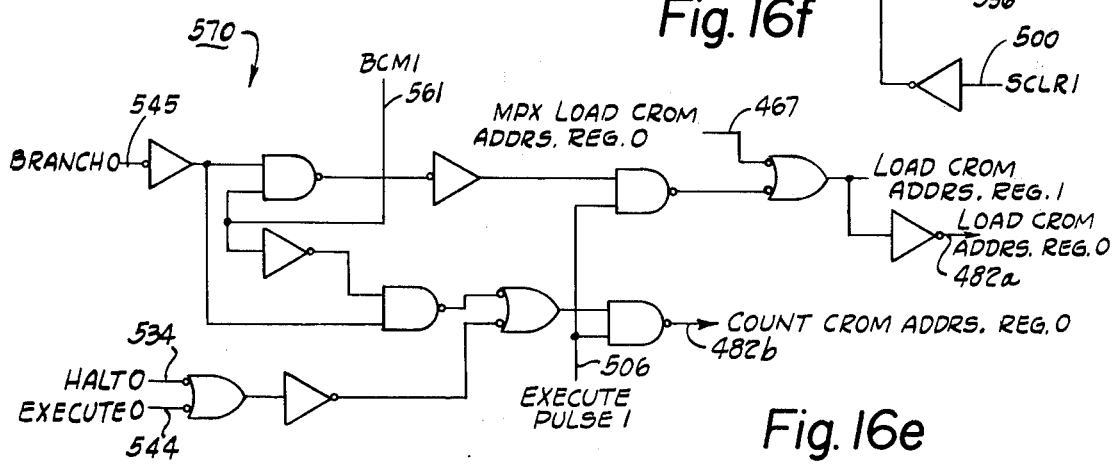
Fig. 16b
Fig. 16c
Fig. 16d
Fig. 16f
Fig. 16e

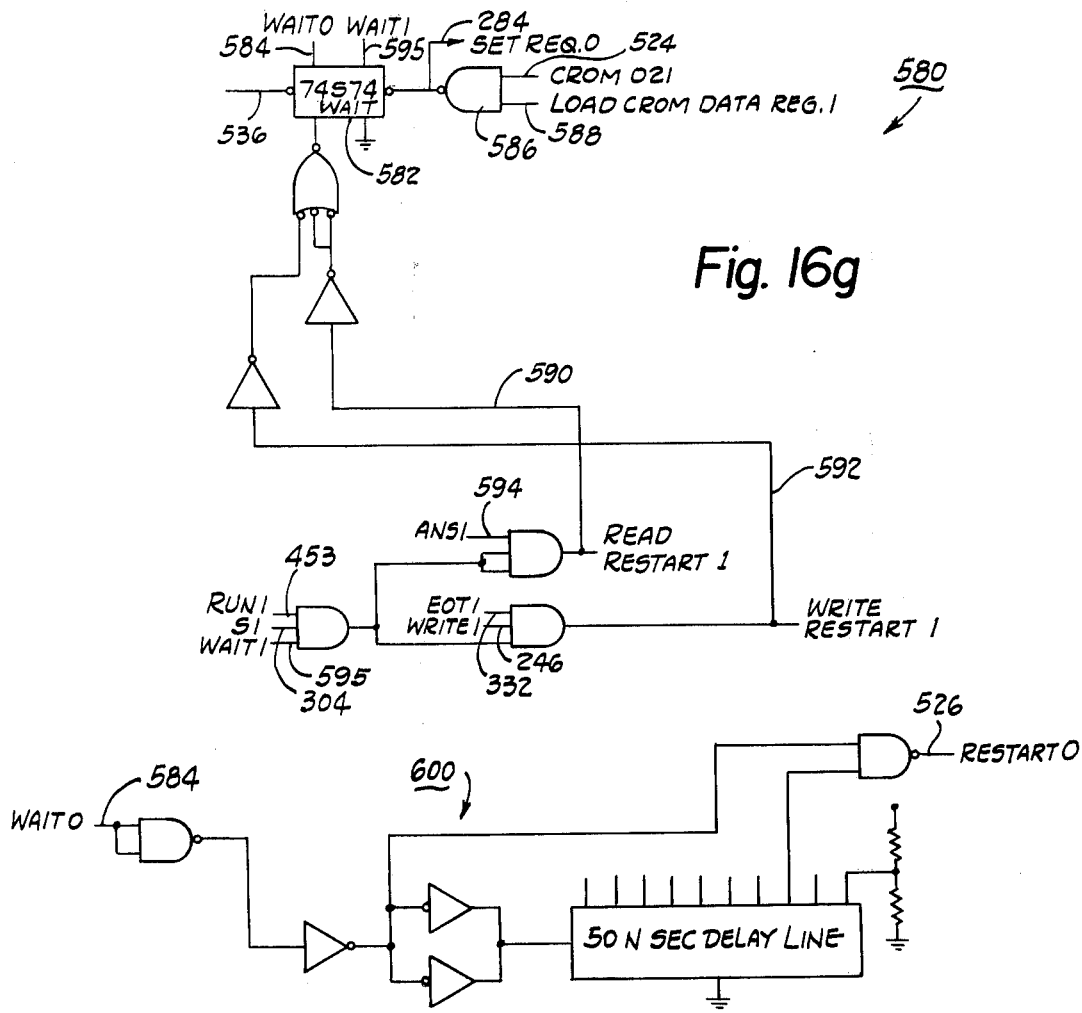
Fig. 16g
Fig. 16h
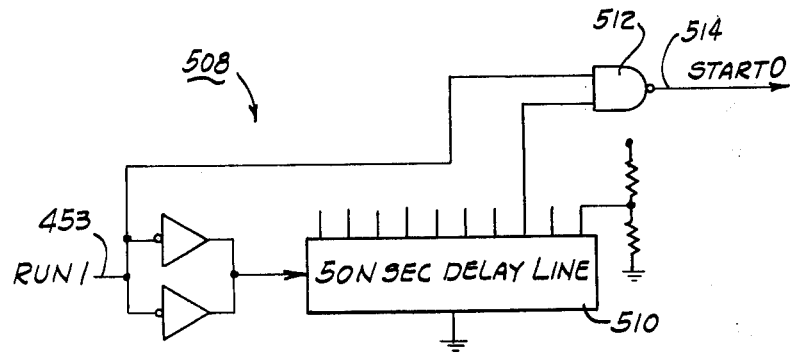
Fig. 16i

TOMOGRAPHY SYSTEM HAVING AN ULTRA HIGH SPEED PROCESSING UNIT

REFERENCES TO RELATED AND RELEVANT PATENTS AND APPLICATIONS

U.S. Patent Application Ser. No. 559,411, entitled TOMOGRAPHY SYSTEM HAVING NONCONCURRENT COMPOUND AXIAL SCANNING, filed Mar. 18, 1975;

United States Patent Application Ser. No. filed Nov. 28, 1975, Ser. No. 635,952, entitled TRANSVERSE TOMOGRAPHY SYSTEM HAVING MULTIBEAM ORBITAL SCANNING WITH ALL BEAMS OFFSET FROM THE CENTER OF ORBIT (7-343), (here the BACKSIDE SCANNING case).

BACKGROUND OF THE INVENTION

This invention relates generally to tomography and, more particularly, relates to a data processing unit for processing data generated in a transverse section, tomographic system to provide a characterization of an internal planar section of a subject.

FIELD OF THE INVENTION

A conventional radiograph is a two-dimensional shadow image of a three-dimensional subject. The depth dimension is not apparent as all interior portions of the subject appear to be in a single plane. As a consequence, a conventional radiograph often fails to provide necessary detail as to spatial location of a condition, is difficult to interpret, and may not reveal a condition which exists.

Tomographic procedures have been developed to fulfill some objectives which are unobtainable by conventional radiographic procedures. In tomography, an image of a crosssectional plane of a subject is developed by sequentially directing radiation through the subject from a plurality of origins. Tomography, in which the radiation is only in what is essentially a single plane and which produces an image of the section of the subject in the plane which includes the axis of the radiation, is known as transverse section tomography.

According to one type of transverse section tomography, called transmission scanning, one or more X-radiation detectors are supported in alignment with one or more highly collimated beams of radiation generated by an X-radiation source. If, as will be assumed for purposes of discussion, a plurality of beams are utilized, they are coplanar. The radiation source and the detectors are moved relative to the subject. The beams are positioned such that they pass through the subject with their axes lying within the plane containing the section of the subject to be examined.

The relative movement may be orbital or rectinlinear with respect to the subject. If rectilinear, the relative movement (referred to as scanning) causes the beams to pass through a succession of coplanar, parallel paths through the subject. The intensity of each beam is detected and recorded after it has passed through the subject. The paths are spaced from one another by predetermined increments. The paths are orientated to be orthogonal to selected radii lying in the plane and extending at predetermined angles from a central axis intersecting the plane. The passage of a beam of radiation along a give path is referred to as a scan element.

The data corresponding to detected intensities at all successive scan elements at a particular orientation about the central axis is said to be data from a particular "view." The angular orientation of the source and detectors about the central axis is incremented after each view and before another view is obtained. This process continues until a predetermined number of views, such as 180, have been performed and the sets of collected data have been stored.

Where studies are conducted with orbital movement of a radiation source and the detectors about the subject, generally a radiation source is utilized which produces a plurality of nonparallel beams of X-radiation. A system of this type is described in the referenced BACKSIDE SCANNING application. The intensities of these nonparallel beams are detected after they have passed through the subject and as the source and detectors orbit the subject. Since the beams are not parallel to one another, sequential detection of the intensities of adjacent beams does not provide data arranged according to a particular "view" at any given orientation about the oribital axis. Accordingly, the data representing the detected intensities must be rearranged if it is to be recorded according to "views" about the oribital axis.

The detected intensities of the beams are utilized for computing X-ray transmission or X-ray absorption characteristics throughout the scanned section. A plot of these characteristics provides a reliable image of the internal structure of the patient in the scanned plane.

A type of transverse section tomography, called emission scanning, which utilizes nuclear radiation has also been proposed. According to this proposal, radioisotope is administered to the subject. A pair of detectors diametrically disposed about the subject measures the intensity of emitted radiation. These measurements are made from a variety of orientations and positions. The values of the detected intensity are used in reconstructing an image of a planar section of the subject. A proposed emission scanning tomographic system is described in Kuhl, et al., "Cylindrical and Section Radioisotope Scanning of the Liver and Brain," Radiology, Vol. 83, No. 5, pp 926–936; 1964.

In transverse section tomography, a back projection computational process is commonly utilized. The back projection computational process operates on a filtered form of the detected radiation intensity data to recontruct an image of the planar section under study.

In order to use the back projection computational process in transmission tomography, the detected X-ray intensity values are stored, in the form of scan data signals, in locations partitioned according to views. Thus, for orbital studies, the stored scan data signals are rearranged according to views, i.e., so that the signals stored at adjacent locations have values which correspond to intensities detected along adjacent parallel paths.

After the scan data signals are arranged according to views they are usually compensated (referred to as the filtering stage) to place them in a form compatible with the back projection process. That is, the back projection process results in a less accurately reconstructed image if the measured values of the scan data signals are used as the values which are to be back projected. The reason for this is that each scan element should contribute to the array, not only along its own path, but also to neighboring paths in decreasing and opposing amounts. The filtering to remove the error usually takes the form of (1) mathematical transformation or, (2) linear weighting operations. The mathematical transformations usually involve direct and inverse Fourier transformation and the linear weighting operations usually involve a mathematical convolution which weights the values of the scan data signals appropriately. The values of the resulting filtered scan data signals are used as the values which are to be back projected for reconstructing the planar section image.

The various types of filtering are well understood and documented. A detailed discussion of Fourier techniques is found in Shepp, et al., SOME INSIGHTS INTO THE RECONSTRUCTION OF A HEAD SECTION, (1974). Detailed discussions of convolution techniques are found in: Gilbert, THE RECONSTRUCTION OF A THREE-DIMENSIONAL STRUCTURE FROM PROJECTIONS AND ITS APPLICATION TO ELECTRON MICROSCOPY, Proc. R. Soc. London B. 182, 89–102, (1972); Ramachandran, et al., THREE DIMENSIONAL RECONSTRUCTION FROM RADIOGRAPHS AND ELECTRON MICROGRAPHS: APPLICATIONS OF CONVOLUTIONS INSTEAD OF FOURIER TRANS, Proc. Nat. Acad. Sci. USA, Vol. 68, No. 9, pp. 2236–2240, Sept., 1974.

A comparison of different types of filtering processes is found in Cho, GENERAL VIEWS ON 3-D RECONSTRUCTION AND COMPUTERIZED TRANSVERSE AXIAL TOMOGRAPHY, IEEE, Transactions on Nuclear Science, Vol. NS-21, June, 1974.

After the filtering process has been completed, the filtered scan signals are stored according to views. Usually these signals are stored in linearly disposed storage locations which are spaced from one another. The storage locations used for the filtered scan signals correspond to scan elements in the planar section of the subject.

The values of the filtered scan signals are interpolated, and the interpolated values are stored in the intermediate storage locations. This provides for an overall reconstruction of greater resolution than if the step of interpolation had not been performed.

These stored filtered scan values are then back projected to provide back projected image signals representative of the structure of the planar section. Back projection means that the stored filtered scan values are projected back, with constant value, along a path through the reconstruction array storage locations corresponding to the path of the X-ray beam which produced the scan value. At all points in the reconstruction array, the values of intersecting back projected views are combined. The steps of combining the values at each of the reconstruction points is said to be the step of updating the value of that point. After updating the values of all reconstruction points, the resultant updated pattern represents the density of the planar section at points corresponding to the reconstruction points. Display of the values of these signals provides an image representative of the structure of the planar section.

This back projection technique is described in Kuhl, A CLINICAL RADIOISOTOPE SCANNER FOR CYLINDRICAL AND SECTION SCANNING, Proc. Symp., Athens 1964, Medical Radioisotope Scanning, I.A.E.A., Vienna, 1, 273, 1964.

An in-depth analysis of the effect of the availability of only a finite number of points for back projecting is found in the paper delivered by Snyder, et al., AN OVERVIEW OF RECONSTRUCTIVE TOMOGRAPHY AND LIMITATIONS IMPOSED BY A FINITE NUMBER OF PROJECTIONS, Proceedings of the Workshop on Reconstructed Tomography in Diagnostic Radiology and Nuclear Medicine, San Juan, Puerto Rico, April 17–19, 1975. The described stages of filtering, back projection, and updating have been performed on digital computers. Since these steps are mathematical computations and usually each requires thousands of repetitious calculations, the digital computer is theoretically suitable for performing the computations. However, as transverse section tomography has developed from the clinical evaluation stage into reliable and accepted medical procedure, the capabilities of digital computers have become limiting factors.

Each overall tomographic study should be completed in a minimal amount of time with the minimum risk and discomfort to the subject of the examination. As the intensity detecting apparatus, i.e., the X-ray scanner, is refined for generating the necessary scan data signals in a minimal amount of time (for example, it is anticipated that the scanner in the referenced BACKSIDE SCANNING application will gather the required intensity data on the order of two to twenty seconds depending on the degree of desired resolution), the data processing equipment must also be refined to match the performance of the scaner. Although a digital computer is capable of performing the thousands of necessary computations, it is relatively slow and is unable, by itself, to provide the desired data processing performance.

The speed limitation of the digital computer is better understood by considering an example of a typical data processing task. During development of the present invention, it was deduced that the order of magnitude of the number of computations for each of the described data processing stages is as follows, with "N" representing the number of views or orientations about the subject at which parallel beams of radiation are detected;

| 1. | Acquire data (N views with $\frac{2N}{\pi}$ intensity readings each) | $\rightarrow N^2$ total |
|---|---|---|
| 2. | Reorganize data by views | $\rightarrow N^2$ total |
| 3. | Filtering (using fast Fourier Transform) | $\rightarrow N^2 \ln(N)$ |
| 4. | Interpolation | $\rightarrow N^2$ |
| 5. | Back projection and update | $\rightarrow N^3$ |

Choosing, for purposes of discussion, N equal to 360 views, which is sufficient to reconstruct an array of 240 × 240 points with an acceptable degree of resolution, it is seen that some 130,000 computations are involved for each of the first, second and fourth stages, some 760 thousand for the filtering stage, and some 46 million for the back projection and update stage.

Another expression which was deduced during development of the present invention characterizes the total back projection and updating processing time. This expression reflects row-by-row processing of the array and is:

$$\text{Time (sec.)} = MN(kP^2 + Pt)$$

where

M = Memory cycle time (in sec.).

k = Number of computer memory cycles per array point per row.

P = Array dimension.

t = Number of memory cycles needed to make the changes necessary to shift processing to the next row of array.

If the chosen computer has a cycle time M equal to 750 nanoseconds, with $k=20$, $t=10$, it would take the computer some 5.3 minutes to complete only the back projection and update stage. Considering that the X-ray scanner described in the BACKSIDE SCANNING case is anticipated to collect the necessary data in less than twenty seconds, it is easily understood how it is undesirable for a data processor to take many times as long to perform the back projection stage as the scanner takes to collect the data. For example, the added processing time dictates that the system accommodates fewer studies per given time period, i.e., a reduced patient throughput. More specifically, the fastest known transverse tomography systems take approximately four minutes to produce a reconstructed image from only 180 views. This is acceptable only if the scanner requires four minutes to gather the data, as data collected for one image could be processed while data for another image is being collected. In this way the scanner is not limited by the data processing capabilities. However, a scanner which collects the data in less than twenty seconds is unavoidably idled if the data processor requires some four minutes of processing time. This is so even considering that time is required for the radiologist to reposition the patient between successive data collections corresponding to successive images. This idle time is not only economically unattractive to a hospital for recovery of capital investment, but also could mandate a requirement for additional such systems and for the additional hospital space and personnel for the additional systems.

Another important consideration is that of the impact on the patients. If overall data processing time results in too much idle time of the scanner, such that the patient cannot remain in the radiology room awaiting the results of a first examination, the patient must be reprepared if a second examination is needed. This undesirably subjects the patient to the second preparation, which, depending upon the health of the patient, could be an unpleasant ordeal. Also, the uncertainty of the necessity for a reexamination could mandate a prolonged and otherwise avoidable hospital stay, inconveniencing the patient and tying up hospital facilities.

There has been a prior proposal for reducing the overall amount of data processing time by providing a special processor for operating in association with a digital computer to perform the filtering stage. However, as has been indicated, considerably more steps are required in computing the values for the back projection and update stage than are needed in satisfactorily computing the values for the filtering stage. Accordingly, a reduction in the time required for performing each step of the back projection and update stage, such as by using a special processor dedicated to the specific task, should be considered prior to attempts to reduce the time required for each step of the other stages. This conclusion could not be reached, however, until an in-depth comparative analysis revealed the described, steprequirement relationships among the data processing stages.

There are other considerations, in addition to speed, in the design of a special processor for use in a tomography system. The special processor must provide the necessary degree of accuracy, yet should be sufficiently flexible to accommodate different approaches on handling overflow or underflow conditions in an arithmetic logic unit (ALU). More specifically, an overflow condition occurs when the ALU computes a value, such as the updated value at the intersection of the back projected signals, which is larger than can be accommodated by the data processing system. Upon the overflow condition, the data processing system could automatically indicate the maximum value and not proceed with additional computations for that point. Alternatively, it could indicate the maximum value and proceed to see if a subsequent back projection contributed a negative value to the computation, thereby decreasing the resultant value from the maximum. In the latter case, a negative value of a back projection refers to a back projected value which is less than the value associated with water. A versatile processor would be designed to accommodate either option.

Another important consideration in the design of the special processor is that it be optimally suited for the particular sequence of steps necessary in performing the data processing stage to which it is dedicated. For example, to perform back projection, given an PxP array of points to be updated, the design of the processor should be such that the required sequence for updating all points be accomplished using the least number of memory cycles. If the points of the array are taken row by row, the special processor could be designed to accommodate only the updating of each row of points, with overall row-by-row sequencing controlled by a digital computer. Alternately the complexity and overall cost of the special processor could be increased so that the entire point-by-point then row-by-row operation is wholly under control of the special processor.

If the row of points is to be repetitiously updated point by point for each row (referred to as the inner loop) and then row by row (the outer loop), the design of the special processor should, for a given overall cost and complexity limit, first optimize the required number of memory cycles in either the inner loop or in the outer loop, whichever is more beneficial. An indication of the solution to this design consideration is found in the earlier described expression for overall time required for back projection.

$$\text{Time (sec.)} = MN(kP^2 + Pt)$$

where k is indicative of the number of memory cycles in the inner loop and t is the number of memory cycles in the outer loop. For the computer having a 750-nanosecond memory cycle, a study having N equal to 360 views, an array size P of 240 points per side and the number k of inner loop memory cycles equal to 3, then an overall back projection time of 46.72 seconds is required if the number t of outer loop memory cycles is equal to 1. If the number t of outer loop memory cycles increases to 10, the overall time increases to only 47.3 seconds. Using the same example, if the number of inner loop memory cycles is increased to 4, the overall time increases to 62.27 seconds. Thus, increasing the outer loop memory cycles by 10 increases overall time by only approximately ½ second, but increasing the number of inner loop memory cycles by 1 increases the overall time by over 15 seconds.

All the above factors must be considered in any attempts to reduce the overall data processing time in a tomography system.

SUMMARY OF THE INVENTION

The above-noted and other drawbacks of the prior art are overcome by the present invention by providing an ultra-high-speed data processing unit which repetitively performs several time-consuming operations concurrently. The data processing unit reduces to a near minimum the amount of time required for computing back projected and updated values. Because the number of steps required for performing back projections and updating grows by a cubic factor with the number of data views, and the other data processing stages do not, minimizing the time required for the back projecting and updating stage results in a greater than proportional reduction in overall data processing time, thereby allowing images of whole body scan cycles to be reconstructed in a matter of seconds. This allows a radiologist to view the results of each scan cycle substantially immediately upon the completion of the scan cycle. Advantages of prompt image reconstruction include: (1) allowing immediate reexamination without repeating patient preparation and system set-up procedures, and (2) maximizing the number of examinations which may be conducted by minimizing the amount of time required for each examination. The data processing unit provides the accuracy needed for exact reconstructions, yet is of a design which is versatile for accommodating different computational processes and is relatively economic to manufacture.

The transverse section tomography system according to the invention includes a radiation detector and a data processing unit which coact to generate a set of resultant image signals characterizing structure of a planar section of a subject. The scanning detector is movably positioned for detecting radiation which has passed through the subject and generates a sequence of scan data signals indicative of the intensity of this radiation. Detection of the radiation at a given orientation and position defines a scan element, and detection of the radiation at all predetermined orientations and positions defines a scan cycle.

The data processing unit generates the set of resultant image signals in response to the sequence of scan element data signals. The data processing unit includes an input storage section for storing the respective scan element data signals in a particular sequence of input storage locations. A filtering processor is coupled to the input storage section for successively retrieving the scan element data signals and for producing therefrom filtered scan signals representative of the image contribution of each scan element.

A scan storage section is provided for storing the filtered scan signals. Each filtered scan signal is retrievably stored in a scan storage location corresponding to the scan element position and orientation from which the signal was derived.

A reconstruction array storage section is provided. As they are generated, elemental image signals are stored in array storage locations coordinated with an array of points of the planar section to be reconstructed. The elemental image signals are each successively updated to eventually represent the density of the planar section of the subject at each of the points.

Array storage and scan storage address calculators are provided. The array storage address calculator sequentially determines the address of and addresses the array storage location of each elemental image signal. The scan storage address calculator determines and addresses the scan storage location of the filtered scan signal which contributes to the reconstruction of the image at each point determined by the array storage address calculator.

The data processing unit additionally includes a reconstruction update unit. The reconstruction update unit combines each addressed filtered scan signal with the corresponding addressed elemental image signal to provide the updated elemental image signal. Eventually, the updated elemental image signals become the resultant image signals.

According to one outstanding feature of the invention, a control unit is provided for operating the scan storage address calcultor and the array storage address calculator concurrently.

According to another feature of the invention, the array storage includes addressing and data transfer circuitry which is operated concurrently with at least one of the address calculators. The circuitry writes each updated image signal corresponding to a selected point into the corresponding array storage location.

The preferred transverse section tomography system uses a scanner which includes an X-radiation source. The source produces at least one beam of X-radiation of relatively small cross-section having an axis in the plane of the subject to be examined. The beam is directed at several orientations from a succession of positions. The radiation detector detects the intensity of the beam of X-radiation after it has passed through the subject to constitute a scan element.

The data processing unit is connected to the scanner and includes first and second data processors. The first data processor includes the input storage, the filtering processor, the scan storage section, and the array storage section. The second data processor includes the array storage address calculator, the scan storage address calculator, the updating unit, and addressing units for addressing the scan and the array storage sections.

The first data processor is a programmed digital computer and the second data processor is a special processor implemented using Read-Only Memory (ROM) architecture. The array of points represented in the array storage is automatically updated with the updated elemental image signal by the special processor on a point-by-point basis for each row. The digital computer controls operations of the special processor for row-by-row updating.

In operation, the digital computer conditions the special processor to begin updating the first point in the first row of the array represented in the array storage section. Once conditioned, the special processor has complete control of its operation, as well as control of the scan and the array storage sections in the digital computer. This is a feature which allows the digital computer to perform, if desired, other data processing operations concurrently with and independent of the back projection and updating process performed by the special processor.

After the special processor has updated each point in the first row of the array (i.e., has provided and written the value of the updated elemental image signal into the proper array storage location), it gives control back to the computer. The computer then conditions the special processor for updating the second row of the array represented in the array storage section. The special processor then updates the second row and this sequence of operation continues until the entire array is updated.

The specific steps which are performed to accomplish the back projection and updating of each point are as follows. The initial conditioning by the digital computer provides the special processor with the addressing of the storage locations in the scan storage and in the array storage corresponding to the first point in the array which is to be updated. Control is obtained by the special processor, and it retrieves a filtered scan data signal and the corresponding elemental image signals. These signals are combined to provide the updated elemental image signal, and this signal is transmitted to the array storage section. While the digital computer is writing this signal into the appropriate array storage location, the special processor is calculating the next relevant addresses of the scan and array storage locations. When the digital computer has completed the step of writing the updated elemental image signal into the array storage section, the next calculated address locations are transmitted to the array storage for retrieving the next filtered scan data signal and the next elemental image signal.

The scan address calculator includes a scan origin register which is initially conditioned by the computer to store the origin of the computer's memory which defines the beginning of the scan storage section.

A scan address register and a scan address extension register are provided. They are initially conditioned by the computer to contain the address of the scan storage location, relative to the origin, of the relevant filtered scan data signal which contributes to the reconstruction of the first point in the array which contributes.

A delta scan address register is provided which also is initially conditioned by the computer. The delta scan address register is conditioned to indicate the relative increment (i.e., the delta) between successive relevant scan storage locations. The delta is calculated corresponding to the spacing between adjacent array points and the angle of the particular view.

An operation counter is provided. The operation counter is initially conditioned to indicate the number of points in each row of the array which are to be updated by the scan data signals. After completion of each step of updating, the operation counter is incremented and, unless it indicates that all points in the respective row of the array have been updated, enables calculation of the new scan address.

A processing unit is provided for successively adding the contents of the delta scan address register to the contents of the scan address and the scan address extension registers. This provides the addresses of successive locations in the scan storage corresponding to successive points in the array to be updated.

The array address calculator includes an array counter which is initially conditioned to indicate the address of the first point in the array to be updated. It is incremented after each step of updating, and its contents indicates the array storage location corresponding to the next point in the array to be updated.

The reconstruction update unit includes a memory unit, an accumulator unit, and the processing unit. In the preferred embodiment, the memory unit comprises a single register for temporary storage of data transmitted from the scan storage section. After the processing unit has added the contents of the delta scan address register, the scan address and the scan address extension registers to provide a new scan address, and after the array counter has been incremented to indicate the new array address location, the respectively addressed scan data and elemental image signals are retrieved and are transmitted respectively into the accumulator unit and into the memory unit. These signals are then transmitted to the processing unit and are combined to provide the updated elemental image signal. This signal is then written into the appropriate array storage location. As the computer is executing this operation, the special processor is concurrently incrementing the operation counter and the array counter in preparation for updating the next array point.

Accordingly, it is a general object of the present invention to provide a tomography system having a new and improved data processing unit.

Other objects and advantages will become more apparent when reading a detailed description of a preferred embodiment in conjunction with the following drawings.

BRIEF DESCRIPTION OF THE DRAWINGS

FIG. 2 is a generalized flow diagram of stages in a computational process utilized in the tomography system of FIG. 1;

FIGS. 3a-3j are illustrations of the relationships among a planar section of a subject scanned by the tomography system of FIG. 1, the position of points of an array represented in array storage locations in the system of FIG. 1, and the position of scan storage locations in the system of FIG. 1 which correspond to points of the array.

FIG. 5 is a flow diagram depicting the functional relationships between a general purpose processor and the special processor of the system in FIG. 1;

FIG. 6 is a flow diagram representing operation of the special processor as it performs its task in the overall back projection and update stage of the flow diagram in FIG. 2;

FIGS. 11a-11b are diagrams of an arithmetic logic unit utilized in the processing unit of FIG. 10;

FIG. 14a is a functional block diagram of FIGS. 14b-14f which are sectioned diagrams of control logic for a multiplexor channel control unit in the special processor of FIG. 4;

DETAILED DESCRIPTION OF A PREFERRED EMBODIMENT

Figure 1:
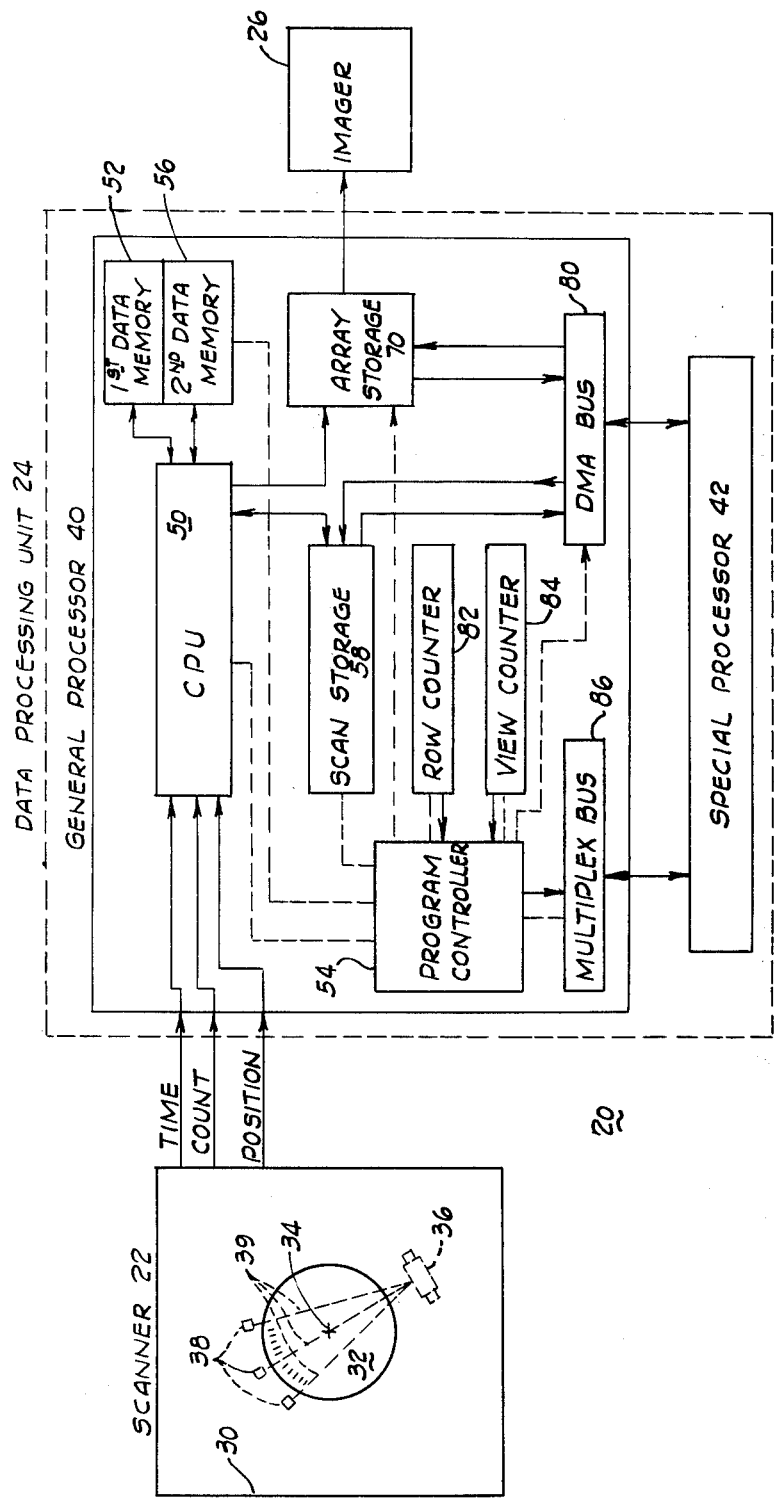
FIG. 1 is a functional diagram of a transverse section tomography system employing the invention.

A tranverse tomography system 20 is shown in FIG. 1. The system 20 includes a scanner 22 which passes beams of X-radiation through a subject, detects the intensity of the X-radiation after it passes through the subject, and provides signals indicative of the values of the intensity of the detected radiation. The beams are passed through the subject at predetermined orientations and positions and have axes which lie in a planar section of the subject. A data processing unit 24 is coupled to the scanner 22 for receiving the signals which characterize the intensity of the detected radiation. In response to these values, the data processing unit 24 generates a set of elemental image signals. The elemental image signals are repeatedly updated and eventually define density characteristics of the planar section of the subject.

An imager 26, such as a storage cathode ray tube or a printout device, is coupled to the data processing unit 24 for displaying the image signals and manifesting the density characteristics of the planar section of the subject.

The scanner 22 includes a housing and support structure 30 which defines a central passageway 32. A virtual system axis 34 is provided passing axially through the passageway 32. In operation the subject is positioned axially within the passageway 32.

An X-ray source 36 and a set of X-ray detector assemblies 38 are supported by structure (not shown) within the housing and frame structure 30 for orbital movement about the system axis 34. The X-ray source 36 directs one or more highly collimated X-ray beams 39 of relatively narrow cross-section through the central passageway 32. The beams 39 have axes which lie in the planar section of interest, and they pass through the subject positioned within the passageway 32. Orbiting of the source 36 causes the beams 39 to scan the planar section, while maintaining the axes of the beams 39 within the planar section, at a plurality of predetermined orientations and positions to the planar section. Passage of one beam 39 through the subject at a particular position and orientation with respect to the system axis 34 is referred to as a scan element and passage of the beams 39 through all predetermined orientations and positions is referred to as a scan cycle. Intensity data acquired by beams which are parallel to and incrementally spaced from one another about a particular orientation around the system axis 34 are referred to as a data from a particular view.

The detector assemblies 38 are supported in alignment with respective ones of the beams 39 and orbit with the source 36. The assemblies 38 produce scan data signals indicative of the intensities of the respective X-ray beams as they pass from the subject. As the source 36 and the detector assemblies 38 orbit about the system axis 34, and the scan data signals are generated, position indicators (not shown) generate POSITION SIGNALS indicative of the orientation of the source 36 and detector assemblies 38 about the system axis 34. The scan data signals take the form of COUNT SIGNALS indicative of the amount of radiation detected by the assemblies 38 over a period of integration, and TIME SIGNALS indicative of the value of the period of integration.

The scanner 22 is disclosed and described in detail in the referenced BACKSIDE SCANNING patent application, and the subject matter thereof is specifically incorporated by reference.

THE DATA PROCESSING UNIT 14

The data processing unit 24 includes a general processor 40 and a special processor 42. The general processor 40 is responsive to the scan data signals (i.e., the TIME SIGNALS and the COUNT SIGNALS) and to the POSITION SIGNALS, and operates on these signals in a manner depicted by the generalized flow diagram of FIG. 2.

The flow diagram of FIG. 2 represents a filtered back projection-type computation process and includes a first block 44 representing a data acquisition stage. To perform this stage, the general processor 40 includes a central processing unit 50 (here the CPU), a first data memory 52, and a program controller 54. The CPU 50 divides the magnitude of the COUNT SIGNAL by the magnitude of the TIME SIGNAL and stores the resulting scan data signals in storage locations in the first data memory 52 associated with the values of the corresponding POSITION SIGNALS. The program controller 54 operates the CPU 50 and the first data memory 52 in a conventional manner to accomplish this processing.

The next data processing stage in the flow diagram of FIG. 2 is functionally represented by a block 45. This stage may not be necessary, depending on the type of scanner used in collecting the intensity values, as it refers to the stage of reorganizing according to views the scan data signals which are stored in the first data memory 52. More specifically, if the scan data signals generated by the scanner 22 are in a sequence corresponding to parallel beams 39 of radiation passing through the subject at a given orientation, the scan data signals are naturally in a sequence for storage according to views. If not, the scan data signals are reorganized for storage according to views. To this end the general processor 40 additionally includes a second data memory 56. The program controller 54 causes the CPU 50 to extract the scan data signals from the first data memrory 52 and to write them into the second data memory 56 according to views.

The next functional block 46 in FIG. 2 refers to the stage of filtering the scan data signals. Because the back projection computational process is based on Fourier analysis, execution of this process on the scan data signals results in certain of the signals, depending on which scan element produced them, being inherently weighted differently from others of the signals. Unless this weight difference is compensated for, the resultant image signals contain distortion. Also, because the scanner 22 detects the intensity of the beams 39 at only a finite number of orientations and positions about the system axis 34, an amount of sampling error is introduced. The step of filtering eliminates or compensates for these error factors so that the resultant filtered scan signal is compatible with the computational process and is more indicative of the contribution of each scan element towards reconstructing the overall image of the planar section of the subject. Conventional filtering techniques are now well-known and include transformations using Fourier analysis and include linear weighting procedures using convolution. These techniques are described in the referenced Shepp, et al., Gilbert, Ramachandran, et al., and Cho articles which are incorporated herein by reference.

To perform the step of filtering, the general processor 40 additionally includes a scan storage section 58. The program controller 54 operates the CPU 50 to extract the reorganized scan data signals from the second data memory 56, to filter them according to either of the referenced filtering processes, and to write the value of the filtered scan signals into address locations in the scan storage section 58 corresponding to views.

The next functional block 47 in FIG. 2 refers to the stage of interpolating the filtered scan data. Interpolation provides values representative of filted scan data signals measured at angle and positions between the angles and positions at which the intensity of the beam was actually detected. These interpolated filtered scan data are stored in scan storage locations intermediate to the locations corresponding to the actually detected filtered scan signals. According to one known method of interpolation, the program controller 54 is conditioned to operate the CPU 50 to provide the filtered scan signals into spaced scan memory locations, to linearly interpolate between values of the detected intensities, and to place the resulting interpolated values into the appropriate locations. For example, the CPU could place adjacent filtered scan signals in alternate address locations in the scan memory 58 and could then provide the average of the two signals in the intermediate address location between the respective filtered scan signals.

As described, the general processor 40 may be any of well-known data processors. For example, it may take the form of a digital computer with the CPU 50, data memories 52, 56 and program controller 54 corresponding to those components in a digital computer. Computer programs for programming the controller 54 to operate the general processor 50 to perform the steps represented in the blocks 44-47 are well-known in the art and need not be explained further. For example, the referenced Shepp, et al., publication generally describes a computer program utilizing Fourier analysis as the filtering stage of block 46.

Figure 4:
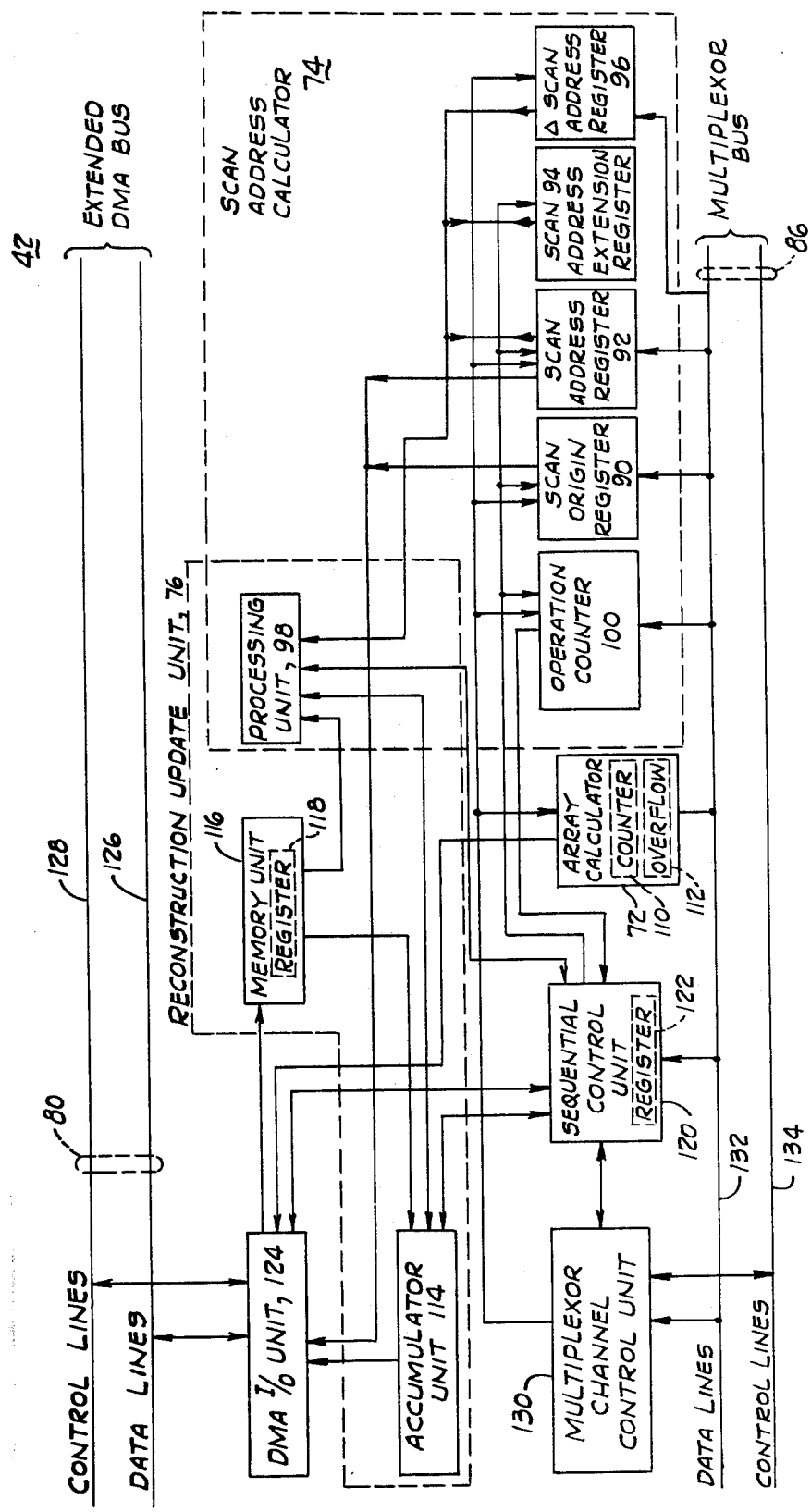
FIG. 4 is a functional diagram of a special processor used in the system of FIG. 1 for performing a back projection and update stage of the flow diagram in FIG. 2.

Referring again to FIG. 2, the last functional block 48 in the flow diagram refers to the back projection and update stage of the computational process. To perform this stage, the general processor 40 further includes an array storage section 70, and the special processor 42 includes an array address calculator 72, a scan address calculator 74, and a reconstruction update unit 76 (FIG. 4).

EXAMPLE OF BACK PROJECTION

Figure 3E:
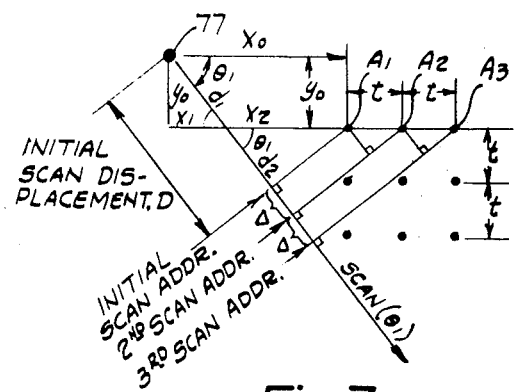

Referring to FIGS. 3a-3j understanding of the back projection and update stage of the computational process is facilitated by first describing a specific example. In FIG. 3a, a preselected array A of points Ai is selected in relation to the planar cross-section of the patient (not shown in FIG. 3a) under study. The array A is shown to comprise a rectangular three-row by three-column array of points (Ai with $i$ equal to 1, 2, . . . 9). The rows and columns are spaced by a spacing $t$.

The specific size and geometry of the array A is not limited to such a rectangular configuration, as the data processing unit 24 does not depend upon any given array size or configuration. Other exemplary array A configurations which may be selected are shown in FIGS. 3h-3j. FIG. 3h depicts an array A arranged in a triangular geometry. FIG. 3i depicts an array A arranged as paralleogram. FIG. 3j depicts an array A arranged in a generally circular-shaped geometry. As will subsequently become apparent, the only requirement for the data processing unit 24 according to the preferred embodiment is that points Ai of the array A be identified in rows, with substantially equal spacing $t$ between adjacent points in each row. The spacing between adjacent rows is chosen to equal the spacing between adjacent points in a row merely for convenience of description.

The preselected array of points Ai is assigned storage locations Ai* (FIG. 3b) in the array storage 70. Values referred to as elemental image signals are eventually calculated and written into the appropriate array storage location. The values are repeatedly updated according to the stage of back projection to eventually represent the density of the subject at the corresponding points Ai.

In FIG. 3a, one of the beams 39 is represented as emanating from the radiation source 36 at an angle $\theta$ measured from a reference line R. The source 36 is shown as having been translated to pass the beam 39 along several paths each oriented at angle $\theta$. In theory, the intensity value of the beam 39 after it has passed through the subject conveys density information about the points (corresponding to the points Ai) of the subject through which it passes. If the beam 39 does not pass through a point corresponding to a particular point of the array A for a given angle $\theta$ (i.e., for a given view) but passes near the particular point, it may be assumed to contribute towards reconstruction of the image at that point by virtue of the interpolation stage 47 of the computational process.

The detected intensity values of the beam 39 as it is translated to pass along several paths at a given angle $\theta$ (for a given view) are stored in the scan storage section 58 in succesive locations. The spacing between scan storage locations corresponds to the translational distance of the source 36. The succession of scan storage locations 58 is schematically represented for a given view (at angles $\theta = 1, 2, 3, 4$) in FIG. 3c as lines extending from respective origins 77 (representing the first memory location in the scan storage 58 and extending in a given direction) representing the successions of locations. The values stored in the scan storage 58 are referred to as values Vij as collected for a given view. The storage locations of the values Vij for a view at angle $\theta$ are represented in FIG. 3c as linearly disposed locations having addresses which increase from an origin 77. The storage of the values Vij is referred to as a SCAN ($\theta$i).

FIG. 3d schematically illustrates the process of back projection as it is implemented for the collection of filtered intensity data at four views: SCAN($\theta$1), SCAN($\theta$2), SCAN($\theta$3), SCAN($\theta$4). The four SCAN($\theta$i) representations are arbitrarily positioned in relationship with the points Ai, with the orientation of the SCAN($\theta$i) representation at the respective angle $\theta$i from which the values Vij were produced. Each SCAN($\theta i$) representation is shown having orthogonal paths Pij which extend into the array A. These paths Pij may be thought of as representing an assumed beam 39 which passed through or near the assumed points Ai, causing the corresponding values Vij to be generated and stored in the scan storage locations which are represented by the respective SCAN($\theta i$) representations.

Each point Ai is identified with a scan storage location and associated value Vij for each of the SCAN($\theta i$) representations. The address of the associated scan storage location and value is determined by calculating the scan storage location in the scan storage 58 which contains the value Vij attributed to the assumed X-ray beam 39 passing through the particular point Ai. Accordingly, for the point Ai, the path P41 extending orthogonally from the representation SCAN($\theta 4$) and passing through the point Ai identifies the storage location. The value at this storage location is the value of the filtered scan data signal V41. Looking at this determination from another viewpoint, the value V41 is back projected along the path P41 at its given value and is attributed to all points Ai of the array A through which the path P41 passes (which, in this case, is only the point A1).

In a like manner, the value V31 is back projected along the path P31 for the SCAN($\theta 3$) representations: the value V21 is back projected along the path P21 for the SCAN($\theta 2$) representation; and the value V11 is back projected along the path P11 for the SCAN($\theta 1$) representation. This procedure is repeated for the remaining points A2-A9 for all four views.

The step of updating is defined as the step of combining all values Vij which, when back projected along the respective path Pij, pass through or near the given point Ai. For example, the updated value of all back projections corresponding to point A1 is equal to V11 plus V21 plus V31 plus V41. This updated value is the updated image signal which is representative of the density of the subject at the point corresponding to A1.

Figure 3F:
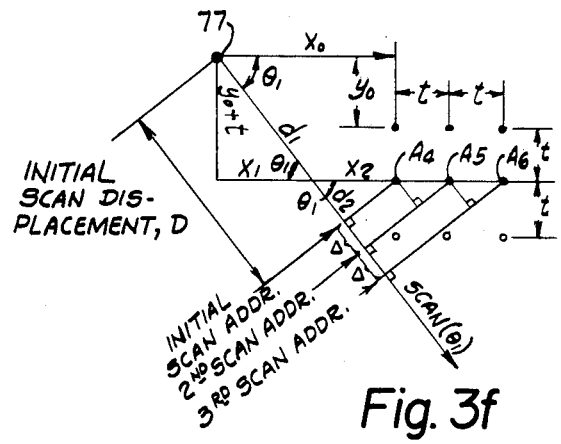
Figure 3G:
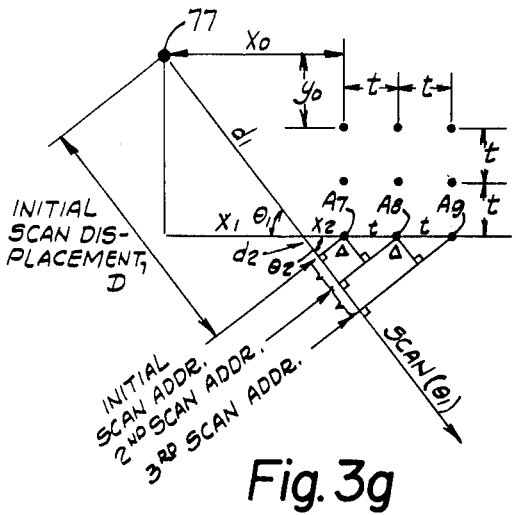
Figure 3H:
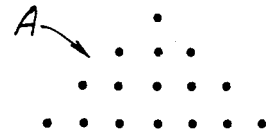
Figure 3I:
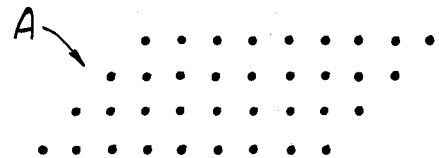
Figure 3J:
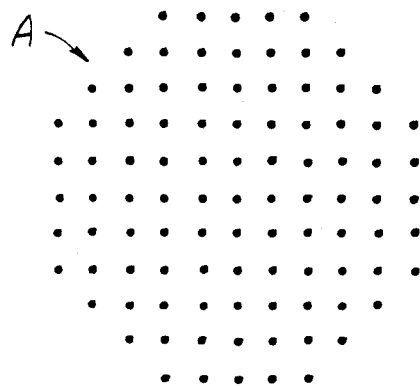

The operation of the data processing unit 24 in calculating the relevant scan address locations (hereafter Lij) is schematically illustrated in FIGS. 3e-3g. These figures respectively depict the step of back projection for each of the three rows of the array A for the view $\theta 1$ (with the stored filtered scan data signals represented by the SCAN($\theta 1$)) representation.

In FIG. 3e, the first relevant storage location (L11) whose address is to be calculated corresponds to the point A1. The address of the storage location L11 is initially computed by the general processor 40 as follows. The origin 77 of the SCAN($\theta 1$) representation has a location relative to the location of the point A1 in the array storage 70 defined by the coordinates $x0, y0$. This location $x0, y0$ is determined by the mapping relationship between the scan storage section 58 and the array storage section 70. The scan storage location L11 is determined in FIG. 3e to be equal to the sum of the distances $d1$ and $d2$ where $$d1 = y0/\sin(\theta 1) \qquad \text{EQN 1}$$

and it can be shown that $$d2 = (x0 - y0\cot(\theta 1))\cos(\theta 1) \qquad \text{EQN 2}$$

From Equations 1, 2 it can be shown that $$d1 + d2 = x0\cos(\theta 1) + y0\sin(\theta 1) \qquad \text{EQN 3}$$

Because adjacent points in the first row are consistently separated (by the spacing $t$), it can be shown that an increment, $\Delta$, between the scan storage location L11 and the scan storage location L12 is given by Equation 4.

$$\Delta = t\cos(\theta 1) \qquad \text{EQN 4}$$

Equation 4 is valid for determining the address of the next relevent scan storage location for each of the points in the first row of the array A, as long as the points are separated by equal spacings $t$. The address of location L12 is $d1 + d2 + \Delta$, and the address of the location L13 is $d1 + d2 + 2\Delta$.

The steps for back projecting the second row of the points Ai (points A4-A6) is characterized in FIG. 3f. The scan storage location L14 corresponding to the point A4 is determined as follows. Defining the sum of the distances d1, d2 to be the initial scan displacement, D, the displacement D equals $$D = d1 + d2 \qquad \text{EQN 5}$$

$$d1 = (y0 + t)/\sin(\theta 1) \qquad \text{EQN 6}$$

$$d2 = [x0 - (y0 + t)\cot(\theta 1)]\cos(\theta 1) \qquad \text{EQN 7}$$

Accordingly, combining Equations 6 and 7 yields $$D = d1 + d2 = x0\cos(\theta 1) + (y0 + t)\sin(\theta 1) \qquad \text{EQN 8}$$

As described with respect to FIG. 3e, the adjacent scan storage locations L14, L15, and L16 are separated by the constant increment $\Delta$. Accordingly, the address L15 and L16 are respectively given by D plus $\Delta$ and D plus 2 $\Delta$. The increment $\Delta$ is as previously given by Equation 4.

FIG. 3g depicts back projection of the third row of the array A (points A7-A9). From FIG. 3g it is seen that the initial scan displacement D which defines the scan storage location L17 corresponding to the point A7 is given by the equation $$D = d1 + d2 \text{ where } d1 = (y0 + 2t)/\sin(\theta 1) \qquad \text{EQN 9}$$

$$D = [x0 - (y0 + 2t)\cot(\theta 1)]\cos(\theta 1) \qquad \text{EQN 10}$$

Accordingly, combination of Equations 9 and 10 yields the initial displacement as given in Equation 11.

$$D = d1 + d2 = x0\cos(\theta 1) + (y0 + 2t)\sin(\theta 1) \qquad \text{EQN 11}$$

The spacing between the scan storage locations L17, L18, L19 corresponding to adjacent points in the third row of the array A is also given by Equation 4. Accordingly, the addresses of the locations L18, L19 are respectively given by D plus $\Delta$ and D plus 2$\Delta$.

From the above discussion it may be seen that equations may be generalized to characterize the increment $\Delta$, the initial scan displacement D, and the addresses of the succeeding points Ai in a given row. The expression for the initial scan displacement D which characterizes the first scan storage location corresponding to the first point Ai of a given row is given by Equation 12.

$$D = x0\cos(\theta 1) + [y0 + (n-1)t]\sin(\theta i) \qquad \text{EQN 12}$$

where $n$ is the row number of the given point under consideration. The increment $\Delta$ is given by Equation 13.

$$\Delta = t\cos(\theta i) \qquad \text{EQN 13}$$

The address if the second and successive points in a given row is given by Equation 14.

$$\text{Lim} = (D + (m-2)\Delta) + \Delta = D + (m-1)\Delta \qquad \text{EQN 14}$$

where $m$ is the number of the point in the row under consideration.

Calculating the new scan address of each successive scan storage location in the above manner eliminates unneeded data processing time. That is, the value of the initial scan displacement D and the value of the increment $\Delta$ can be precalculated once for each row for the selected geometry and then used on an as-needed basis for each row back projection. Specifically, in the illustrated and preferred embodiment, the general processor 40 calculates the values of the initial scan displacement D for each row at each angle $\theta i$ for all views and calculates in the increment $\Delta$ for each angle $\theta i$. With this information and given the number of points in the given row, the special processor 42 via the scan address calculator 74 can rapidly calculate the addresses of the required scan storage locations corresponding to all points Ai.

In the preferred and illustrated embodiment, the general processor 40 is implemented by a Model 7/32 digital computer manufactured by Interdata Corporation, Oceanport, New Jersey. The special processor 42 is specifically implemented to coact with the Interdata digital computer via a plug-in card connector in accordance with prescribed Interdata specifications. The specific interconnections will be described in detail subsequently.

According to the illustrated and preferred embodiment, the general processor 40 includes a direct memory access (DMA) bus 80 and a multiplexor bus 86 which directly communicate with the special processor 42. The general processor 40 further includes a row counter 82 and a view counter 84 respectively for keeping track of (1) which row of the array A represented in the array storage 70 is being back projected and updated and (2) which view of filtered scan signals are currently being back projected and updated.

THE SPECIAL PROCESSOR 42

The Scan Address Calculator 74

The scan address calculator 74 of the special processor 42 includes a scan origin register 90 which is initially conditioned by the general processor 40 to indicated the origin 77 of the scan storage locations SCAN($\theta i$) representing a given view. More specifically, the scan storage 58 includes 4,096 words of linearly disposed memory elements which contain the filtered scan data signals for all views. The scan origin register 90 is conditioned to indicate the origin or address of the first word location of each plurality of word locations in the computer memory which have been designated to store the filtered scan data signals for a given view.

A scan address register 92 and a scan extension register 94 are provided. The scan address register 90 is repetitiously conditioned to provide for a given view, relative to the address location of the respective origin 77 stored in the scan origin register 90, the address of the scan storage location of all filtered scan signals corresponding to the given array A. Thus the contents of the scan address register 92, when concatenated with the contents of the scan origin register 90, provides the absolute address of any element within the scan storage 58.

A delta scan address register 96 is provided. The delta scan address register 96 is conditioned by the general processor 40 to store the relative address increment, $\Delta$, (FIG. 3d). The increment $\Delta$ (which will also be referred to as DELTA) is added to each scan address in the scan storage 58 to produce the address of the next scan storage location corresponding to the next point Ai in the back projection row. The value of the increment DELTA is calculated according to the Equation 4. The delta scan address register 96 has a sign bit which is set to a logic one for angles $\theta$ corresponding to views between 90° and 270° and is a logic zero for all other values of the angle $\theta$.

A processing unit 98 is provided for combining the contents of the scan address register 92 and the scan address extension register 94 with the contents of the delta scan address register 96. This provides the address location of the next in-sequence value Vij in the scan storage 58 corresponding to the next in-sequence point Ai. Specifically, the value of the increment DELTA is added to, or subtracted from, the previous scan address. The processing unit 98, of the sign bit of the delta scan register 96 is a logic one, subtracts the value of the delta scan address register 96 from the contents of the registers 92, 94. Otherwise, the values are added.

The scan address calculator 74 also includes an operation counter 100. The operation counter 100 is conditioned by the general processor 40 to indicate the number of points Ai which are to be updated in a given row of the arrow A. Only if the operation counter 100 is indicative that another point Ai is to be updated will the processing unit 98 combine another DELTA value with the contents of the registers 92, 94.

The Array Address Calculator 72

The array address calculator 72 includes an array address counter 110 and an overflow unit 112. The array address counter 110 is initially conditioned by the general processor 40 to indicate the address of the array storage location (FIG. 3b) containing the first point Ai in the particular row of the array A which is to be updated. The indicated address is an absolute address and is automatically incremented each time a point Ai is updated. When incrementing of the counter 110 results in a carry, signifying that all points Ai in the given row have been updated, the overflow section 112 is operated to indicate this condition and to cause transfer of control from the special processor 42 back to the general processor 40.

The Reconstruction Update Unit 76

The reconstruction update unit 76 includes an accumulator unit 114. The accumulator unit 114 serves two primary purposes: (1) storing the result of each newly calculated scan address for transmission to the general processor 40 via the DMA bus 80 and, (2) receiving and storing the value of the point Ai (the respective elemental image signals) which is to be updated and transferring it to the processing unit 98.

The reconstruction update unit 76 further includes a memory unit 116. The memory unit 116 includes a memory data register 118 which stores the selected value Vij from the scan storage 58 which is to be used to update the value of the elemental image signal stored in the accumulator unit 114.

The processing unit 98 is also included in the reconstruction update unit 76 and combines the value Vij with the value of the elemental image signal stored in the units 114, 116 to provide the updated elemental image signal. The processing unit 98 is coupled for transmitting the updated signal back to the accumulator unit 114 for transmission back to the proper array storage location in the general processor 40.

A sequential control unit 120 is provided for controlling the sequence of operations of the address calculators 72, 74 and of the update unit 76. In the illustrated embodiment, the control unit 120 is programmed to effect either one of two alternate operations of the address calculators 72, 74. In order that a specific control sequence may be selected, the control unit 120 includes a control register 122. The control register 122 is initially conditioned by the general processor 40 for selecting the desired control sequence.

In order that the scan and array addresses and the updated elemental image signal may be transmitted to the general processor 40, and in order that the filtered scan value Vij and the value of the elemental image signal to be updated may be transmitted to the special processor 42, a direct memory access input/output (DMA I/O) unit 124 is provided. The DMA I/O unit 124 is coupled to a set of data lines 126 and to a set of control lines 128 of the DMA bus 80. The DMA I/O unit 124 is responsive to signals from the general processor 40 on the control lines 128 for being conditioned to receive the various data on the lines 126. The DMA I/O unit 124 is responsive to control signals generated by the sequential control unit 120 for transmitting the address calculations and the updated signals on the data lines 126 and for transmitting control signals on the lines 128 which control distribution of the signals provided to the general processor 40.

A multiplexor channel control unit 130 is provided. The multiplexor channel control unit 130 is coupled to a set of multiplexor data lines 132 and to a set of multiplexor control lines 134 of the multiplexor bus 86 for initializing the special processor 42 at the beginning of each update sequence for each row of the array A.

Operation of the general processor 40 and the special processor 42 to provide the back projection and update stage of the data processing is shown by the functional block diagram of FIG. 5. In carrying out the functional block diagram of FIG. 5, the general processor 40 generates a plurality of data signals (Dxxx) and a plurality of control signals (ADRS0, CMD0, DA0) respectively on the lines 132, 134 of the multiplexor bus 86. The special processor responds with a "status" signal which is transmitted back to the general processor on the data line 132 corresponding to the D120 data signal. The data signals are multiplexed on the lines 132, and the control signals on the lines 134 dictate the meaning of the data signals. Table 1 below sets forth the meaning of the control signals and data signals.

TABLE 1

| Data Signal | Control Signal |
|---|---|
| Dxxx | ADRS0 (address pulse to indicate that the signals Dxxx represent a device code address location on the special processor). |
| Dxxx | CMD0 (command pulse to indicate that the signals Dxxx represent command instruction). SR0 (Status Request-inquiry sent by general processor). DA0 (Data Available pulse sent by general processor to represent that the signals Dxxx represent initialization data for a given row). |
| D120 | (a status signal sent by special processor to the general processor on one of the data lines 132 in response to a SR0 instruction to indicate whether the special processor has completed its task.) HW0 -(Halfword-sent by special processor to indicate that a two-byte word is being considered). SCLR0 (system clear-sent by general processor to reset special processor). SYN0 -(synchronized-sent by special processor to indicate that the data sent by the general processor has been accepted). |

From Table 1 it is seen that there are three input/output instructions which utilize the data lines 132. These instructions are output command instructions, write halfword instructions, and sense status instructions.

The output command instruction commands the special processor to either "reset" or to "initiate" its task. The least significant bit on the data line corresponding to the D150 bit) is set if the command is "initiate," and the second least significant bit (on the data line corresponding to the D140 bit) is set if the command is "reset." The sense status instruction requests from the special processor the status of its operating condition and requires an answer on the data line corresponding to the D120 bit. The write halfword instruction identifies certain counters and certain registers for loading with information to be next transmitted on the data lines 132.

The various counters and registers are assigned "device address locations" as seen in Table 2. A pair of assumed registers, the output command register and the sense status register, are also assigned device address locations and are respectively called up when the output command and the sense status instructions are transmitted.

TABLE 2

| Control Signal | Function | Instruction | Device Address Location |
|---|---|---|---|
| CMD0 | Reset | Output Command | 30 |
| CMD0 | Initiate | Output Command | 30 |
| DA0 | Load Control Register, 122 | Write Halfword | 31 |
| DA0 | Load Scan Origin Register, 90 | Write Halfword | 32 |
| DA0 | Load Array Counter, 110 | Write Halfword | 33 |
| DA0 | Load Δ Scan Address Register, 96 | Write Halfword | 34 |
| DA0 | Load Scan Address Register, 92 | Write Halfword | 35 |
| DA0 | Load Operation Counter, 100 | Write Halfword | 36 |
| SR0 | Sense Busy | Sense Status | 30 |

To identify when one of the device locations is being addressed for receiving data on the data lines the address signal, ADRS0 is transmitted on the control lines 134. As will be explained with respect to FIGS. 14a–14p, the bits D130, D140, D150 are utilized for designating the device, and the bits D060, D070, D080, D090, D100, D120 are utilized as a group of bits which "enable" calling up of the designated device.

From Table 2 it is seen that the control register 122, the scan origin register 90, the array counter 110, the delta scan address register 96, the scan address register 92, and the operation counter 100 are respectively assigned device address locations 31–36. Accordingly, these devices are enabled for receiving and being conditioned by a subsequent set of data signals on the lines 132 whenever their device address is specified concurrently with the ADRS0 address signal.

Table 3 indicates a preferred interconnection between the Interdata 7/32 computer and the special processor 42 for transmission of the control and data signals.

TABLE 3

| "Backplane Connector 0" | | |
|---|---|---|
| Row 1 | Pin | Row 2 |
| P5 | 00 | GND |
| GND | 01 | GND |
| D000 | 11 | D010 |
| D020 | 12 | L030 |
| D040 | 13 | D050 |
| D060 | 14 | D070 |
| D080 | 15 | D020 |
| D100 | 16 | D110 |
| D120 | 17 | D130 |
| D140 | 18 | D150 |
| SRO | 19 | ADRSO |
| DRO | 20 | CMDO |
| CL070 | 21 | DA0 |
| RACKO | 22 | TACKO |
| SYNO | 23 | ATNO |
| SCLRO | 26 | HWO |
| DGND | 36 | BHO |
| RPCO | 37 | TPCO |
| GND | 40 | GND |
| P5 | 41 | GND |

Except for a pair of signals TPC0, RPC0, the signals in Table 3 which are not listed in Table 1 are for systems other than the special processor 42 connected to the processor 40 and do not form a part of the invention. The signals TPC0, RPC0 are discussed with respect to FIG. 6.

Referring to the flow diagram in FIG. 5, the general processor 40, as indicated by the block 140, initially loads the control register 122. More specifically, the program controller 54 calls up device address 31 (the control register 122) and then causes a write halfword instruction to be sent to the special processor 42 for entering the least significant eight bits of the halfword into the control register 122. These eight bits are decoded to select the starting address of the desired control sequence, stored in the sequential control unit 120, which is to operate the special processor 42.

Next, as indicated by a functional box 142, the program controller 54 causes the scan origin register 90 (i.e., device code address 32) to be called up for receiving a write halfword instruction. This instruction loads the scan origin register 90 with the least significant seven bits of the half word and defines the address of the scan storage location which corresponds to the origin 77 (FIG. 3d) corresponding to the particular SCAN($\theta i$).

The program controller 54 then conditions the view counter 84 (FIG. 1) according to the total number of views constituting the particular study. The view counter 84 is incremented upon completion of the back projection and updating process for each view, and indicates when the requisite number of views has been considered.

Next, the program controller 54, as indicated by a functional box 146 in FIG. 5, calls up the array counter 110 at device location 33. It then sends over to the counter 110 a write halfword instruction which loads the counter 110 with sixteen bits of the halfword. The sixteen bits are encoded to represent the address in the array storage 70 of the first point of the given row of the array A which is to be updated.

Next, as is indicated by a functional block 148, the program controller 54 conditions the row counter 82 (FIG. 1) according to the number of rows in the array A. The row counter 82 is then subsequently incremented upon completion of the updating process for each row and indicates when the total number of rows in the array A have been considered.

The program controller 54, as indicated by a functional block 150 in FIG. 5, next calls up the delta scan address register 96 at device address 34. It causes a write halfword instruction to be transmitted, and the delta scan address register 96 is loaded with the fourteen least significant bits of the halfword. The first of the fourteen bits is the sign bit; the next five bits represent the value of DELTA, indicating the increment between relevant address locations in the scan storage 58 corresponding to adjacent points Ai in the array A. The last eight bits of the fourteen-bit halfword represent extension bits for increasing the accuracy with which the next scan address is calculated.

The next step in the flow diagram of FIG. 5 is indicated by a functional block 152 and comprises calling up the operation counter 100 at device location 36. After the operation counter 100 has been called up, the program controller 54 transmits a write halfword instruction which loads the operation counter with the least significant eight bits of the halfword. The number loaded into the counter 100 is defined according to the expression $255 - n+1$ (to the base 10) where $n$ is the number of array elements to be updated in a given row of the array A. The operaton counter 100 is incremented after each point in a given row of the array A is updated, and is tested after each incrementing to see whether a carry has been generated out of the counter 110.

Next, the program controller 54, as indicated by a functional box 154, calls up the scan address register 92 at device address 35. A write halfword instruction is transmitted to the register 92, and the least significant twelve bits of the halfword are loaded into it. These twelve bits are encoded to represent the address of the first relevant point in the scan storage 58 which contributes to the first point Ai in the array A which is to be updated. The address corresponds to the initial scan displacement D for the given view and given row.

The foregoing sequence completes the preliminary conditioning of the special processor 42. Upon initiation by the general processor 40 (i.e., by the output command instruction meaning "initiate"), the special processor 42 begins its back projection and updating task. This is indicated by a functional block 156 in FIG. 5 which generally represents operation of the special processor 42 according to a flow diagram depicted in FIG. 6. This flow diagram will subsequently be described in detail.

After the special processor 42 has been given memory access control by the general processor 40, and after it has completed its back projection and updating task for a given row of the points of the array A, it gives control back to the general processor 40. The program controller 54 verifies that the special processor 42 has completed its task, as is indicated by a functional block 158 in FIG. 5. More specifically, the program controller 54 calls up device address 30 and transmits a SR0 status request signal. The special processor 42 transmits to the processor 40 a logic one as the D120 data signal if the processor 42 is busy. If the processor 42 is busy, the general processor 40 may stand by until the special processor 42 completes its tasks, or it may execute other functions concurrently with the operation of the processor 42.

After the special processor 42 indicates that it has completed its tasks, the program controller 54 increments the row counter 82, as indicated by a functional block 160. If, after this incrementing, the row counter 82 indicates that not all rows of the array A have been updated, a new number is loaded in the operation counter 100, and the sequence described with respect to the blocks 152-160 is repeated.

When the row counter 82 is indicative that all rows of the array A have been updated, the program controller 54 increments the view counter 84, as is indicated by a functional block 164. If, after incrementing the view counter 84, the counter 84 indicates that not all views prescribed by the functional box 144 have been considered, control is shifted back to the functional block 146, as indicated by the path 170. Operations according to the functional blocks 146-166 are repeated until the view counter 84 indicates that all views have been considered. At this point, a functional block 168 indicates that all rows of the array A have been considered for all views, and the stage of back projection and updating has been completed.

Referring now to FIG. 6, there is a general flow diagram characterizing the operations of the special processor 42 as it performs the functions represented by the functional block 156 (initiate hardware-update row processes in FIG. 5). The program controller 54 gives memory access control to the special processor 42 at the beginning of the back projection and updating process for each row. This is indicated by a block 180 in FIG. 6. According to this operation, a device address 30 is called up, and an output command instruction is transmitted having bit 15 set to a logic one. This enables the sequential control unit 120 to begin the sequence of operation, including the steps of transmitting and receiving information to and from the scan storage section 58 and the array storage section 70. To this end the DMA bus 80 is utilized. Table 4 below sets forth a listing of the mnemonics which are utilized for describing the data and control signals which respectively are transmitted on the lines 126, 128 for interfacing with the scan and array storage sections 58, 70. These signals are further described with respect to FIGS. 7 and 8.

TABLE 4

| Mnemonic | Description |
| --- | --- |
| ANS0 | Answer (Data on DMA bus is valid for transfer) |
| DMA000-DMA170 | Direct Memory Access (DMA bidirectional bus lines or corresponding signals thereon) |
| DMX120-DMX150 | Direct Memory Access (DMA bus lines or corresponding signals thereon) |
| EOT0 | End of Transmission (DMA Bus Signal Signifying end of transmission of data to general processor) |
| LMRQ0 | Local Memory Request (DMA Bus Signal requesting direct memory access for the special processor) |
| LOAD0 | Load DMA bus information |
| MOBZO-M3BZO | Memory Busy Lines (DMA Bus Signals) |
| P | Major DMA Control timing pulse |
| QUE0 | DMA Request One Signal (DMA Bus Signal) |

TABLE 4-continued

| Mnemonic | Description |
| --- | --- |
| RPC0 | Receive Priority Chain |
| SCLR0 | System Clear Reset (DMA Bus Signal) |
| SOT0 | Start of Transmission from general processor (DMA Bus Signal) |
| TPC0 | Transmit Priority Chain (from general processor for priority) |
| XREQ0 | DMA bus request by special processor (DMA Bus Signal) |

A preferred interconnection, on a pin-by-pin basis, of a backplane 1 connector between the general processor 40 and the special processor 42 is given in Table 5. Signals not listed in Table 4 but shown in Table 5 are for other subsystems which are connected to the general processor. These other subsystems do not form a part of the invention.

TABLE 5

| | Backplane Connector 1 | |
| --- | --- | --- |
| Row 1 | Pin | Row 2 |
| P5 | 00 | GND |
| GND | 01 | GND |
| XREQ0 | 02 | QUE0 |
| SOT0 | 03 | EOT0 |
| LMRQ0 | 04 | DGND |
| LOAD0 | 05 | ANS0 |
| M1BZ0 | 06 | M0BZ0 |
| M3BZ0 | 07 | M2BZ0 |
| DMX130 | 08 | DGND |
| DMX150 | 09 | DMX120 |
| | 10 | DMX140 |
| PD000 | 11 | PD010 |
| PD020 | 12 | PD030 |
| PD040 | 13 | PD050 |
| PD060 | 14 | PD070 |
| PD080 | 15 | PD090 |
| PD100 | 16 | PD110 |
| PD120 | 17 | PD130 |
| PD140 | 18 | PD150 |
| PSR0 | 19 | PADRS0 |
| PDR0 | 20 | PCMDS |
| PCL070 | 21 | PDA0 |
| | 22 | PTACK0 |
| PSYN0 | 23 | PATN0 |
| SCLR0 | 24 | PHW0 |
| DGND | 27 | DMA000 |
| DMA010 | 28 | DMA020 |
| DMA030 | 29 | DMA040 |
| DMA050 | 30 | DGND |
| DMA070 | 31 | DMA000 |
| DMA090 | 32 | DMA080 |
| DMA110 | 33 | DMA110 |
| DGND | 34 | DMA120 |
| DMA130 | 35 | DMA140 |
| DMA150 | 36 | DMA160 |
| DMA170 | 37 | DNGD |
| GND | 40 | GND |
| P5 | 41 | GND |

The next step which is commanded by the sequential control unit 120 is to read the array value (the value of the elemental image signal) corresponding to the first point Ai in the given row of the array A from the array storage system 70. This is indicated by a functional block 182 in FIG. 6 and is executed by transmitting the contents of the array address counter 110, via the DMA I/O unit 124 and the DMA bus 80, to the array storage section 70. In response to this array address signal, the array storage section 70 outputs the contents of the addressed location corresponding to the first relevant point Ai via the DMA bus 80 and the DMA I/O unit 124, into the register 118 of the memory unit 116. From the memory unit 116, the value of the elemental image signal is read into the accumulator unit 114.

As is indicated in a block 184 in FIG. 6, the sequential control unit 120 initially causes a selected value Vij in the scan storage section 58 to be addressed and then read into the register 118 of the memory unit 116. To this end, the contents of the scan origin register 90 and the scan address register 92 are output through the DMA I/O unit 124 via the DMA bus 80 for addressing the scan storage section 58. In response to these address signals, the scan storage section 58 outputs the value Vij corresponding to the address location. The value Vij is transmitted via the DMA bus 80 and the DMA I/O unit 124 into the memory unit 116.

Next, as is indicated by a functional block 186 in FIG. 6, the sequential control unit 120 causes one of two operations to be executed depending upon which control sequence was initially specified by the general processor 40. According to the first option, control follows a path 190 to a block 208. According to the block 208, the elemental image value stored in the accumulator 114 (corresponding to the point Ai of the array to be updated) is checked to see if it is a predetermined minimum or a predetermined maximum value. If the value is neither the minimum nor the maximum value, control is transferred (via a line 212) to a block 188. According to the block 188, the sequential control unit 120 causes the contents of the accumulator unit 114 and the memory data register 118 to be transmitted to the processing unit 98 where they are combined. The resultant combined value is then transmitted from the processing unit 98 into the accumulator unit 114.

The resultant value stored in the accumulator unit 114 is then checked for underflow or overflow conditions, as is indicated by a functional block 194 in FIG. 6. Testing for underflow or overflow is performed concurrently, a time-saving feature. If either the underflow or overflow condition exists, the resultant value is erased from the accumulator 114 and either the predetermined minimum or the predetermined maximum value, according to whether underflow or overflow occurred, is written into the accumulator unit 114.

If neither underflow nor overflow has occurred, the resultant value stored in the accumulator unit 114 is written, via the DMA I/O unit 124 and the DMA bus 80 into the array storage 70 corresponding to the previous address location. Because the array counter 110 has not been incremented during this procedure, its content is still representative of the address in the array storage section 70 corresponding to the first point Ai to be updated. After the resultant, or updated value of the elemental image signal, has been written into the array storage section 70, the sequential control unit 120 causes simultaneous incrementing of the operation counter 100 and the array address counter 110. This is a feature of the invention as it reduces the overall time the scan address calculator 74 and the array address calculator 72 need for calculating the respective new address locations corresponding to the next point in the array A to be updated. This is indicated by a pair of functional blocks 197, 198 in FIG. 6.

Referring again to the functional block 186 in FIG. 6, if the value of the elemental image signal stored in the accumulator unit 114 equals the predetermined minimum or maximum value, the sequential control unit 120 bypasses any further operations for updating the corresponding point in the array A and jumps to the functional block 198.

Once the operation counter 100 and the array address counter 110 are incremented, the state of the operation counter 100 is tested. If incrementing of the counter 100 has resulted in a carry, meaning that all points in a particular row of the array A have been updated, the task of the special processor 42 has been completed for that row. A functional block 202 indicates this condition and the operation according to the functional block 158 in FIG. 5 would be finished.

If no carry has been generated out of the operation counter 100, the value of DELTA storaged in the delta scan register 96 and the value (the previous scan address) stored in the scan address register 92 are transmitted to the the processing unit 98 and are combined. The absence of a logic one in the sign bit of the delta scan register causes the processing unit 98 to add the values stored in the registers 92, 96. Otherwise, the DELTA value stored by the delta scan register 96 is subtracted from the value stored in the scan address register 92. This process provides a new scan address corresponding to the next point in the array A and is transmitted both to the scan address register 92 and to the scan address extension register 94 for reconditioning those registers. The new scan address is also transmitted to the accumulator unit 114. From the accumulator 114, the new scan address is transferred via the DMA I/O unit 124 and the DMA bus 80 to the scan storage section 58 for addressing the next relevant location containing another value Vij.

As indicated by a line 206 in FIG. 5, the process defined by the blocks 182-204 continues until incrementing of the operation counter 100 indicates that all points in the array A for a given row have been updated.

According to the second option, indicated by the block 186, the special processor 42 does not test for the array value (the value of the elemental image signal) corresponding to the point Ai to be updated prior to the step of adding the scan value Vij to the array value (functional block 192). This has significance in that the values Vij stored in the scan storage section 58 may assume negative numbers. More specifically, water is utilized as a reference and all detected intensities corresponding to densities in a subject greater than the density of water have values Vij positive in sign, and all detected intensities corresponding to densities less than that of water have values Vij negative in sign. Accordingly, even though the value of the point Ai to be updated is already a minimum or a maximum, subsequent combinations of the new scan value Vij could move the updated value away from the minimum or maximum.

According to the option 2, the operations according to the functional blocks 192-204 are invariably executed after (as indicated by a line 188) the operation described by the block 184.

Specific programs for implementing the flow diagram of FIG. 6 (both options) are given and described in detail subsequently.

The DMA I/O Unit 124

Figure 7:
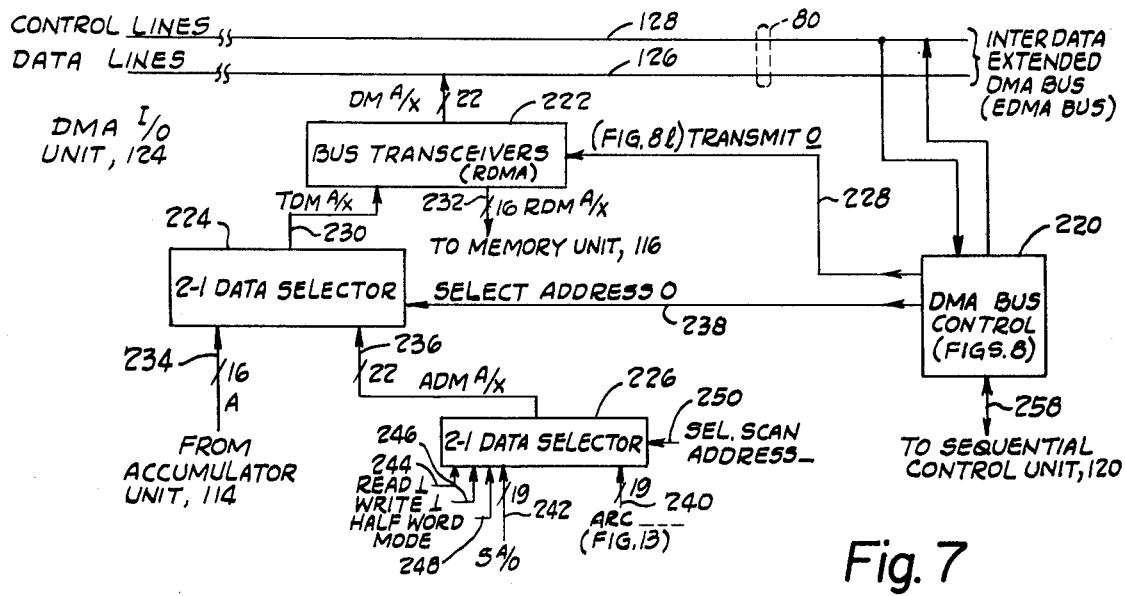
FIG. 7 is a block diagram of a direct memory access input/output unit of the special processor depicted in FIG. 4.

Referring to FIG. 7, the DMA I/O Unit 124 includes a DMA bus control circuit 220, a bus transceiver circuit 222, and a pair of data selectors 224, 226. The bus transceiver circuit 222 is coupled to the data lines 126 of the DMA bus 80 for transmitting and receiving up to twenty-two bits of data. The transceiver circuit 222 receives the values of the elemental image signal and the values of Vij in the form of the DMAxxO and DMXxxO signals (hereafter the DMA/X signals) from the general processor 40. The transceiver circuit 222 transmits the updated elemental signals and the scan and array addresses to the general processor 40 also via the DMA/X signals. The transceiver circuit 222 is enabled by a TRANSMITO signal on a line 228 from the DMA bus control circuit 220. A logic zero state dictates that the circuit 222 is in a transmit mode and a logic one state dictates a receive mode.

The transceiver circuit 222 has sets of input terminals coupled to the data selector 224 and to the memory unit 116 via TDM lines 230 and RDM lines 232, respectively. The data selector 224 generates TDMAxxl and IDMXxxl signals (hereafter the TDMA/X signals) onto lines 230 representative of either (1) the updated value of the elemental image signal, (2) the address of the next scan storage location to be considered, or (3) the address of the next array storage location to be considered. These TDMA/X signals are transmitted by the transceivers 222 as the DMA/X signals.

The transceiver circuit 222 also provides (via the DMA/X signals) RDMAxxl and RDMXxxl signals (hereafter the RDMA/X signals) on the lines 232. The RDMA/X signals are the values Vij and the values of the next elemental image signal to be updated and they are transmitted to the memory unit 116.

The data selector 224 has one input coupled to a set of A lines 234 of the accumulator unit 114 and has a set of ADM lines 236 coupled to the data selector 226. The data selector 224 selects either Axxl signals (hereafter the A signals) from the accumulator unit 114 or ADMAxxl and ADMXxxl signals (hereafter the ADMA/X signals) from the data selector 226, whenever enabled, for transmission as the TDMA/X signals. A SELADDRESSO signal on a line 238 is generated by the DMA bus control 220 for enabling operation of the selector 224.

The data selector 226 has input terminals coupled to a set of ARC lines 240, coupled to a set of SA/O lines 242, and to a set of lines 244, 246, 248. The ARC lines 240 are coupled to the array address counter 110 for transmitting via ARCxxl signals (hereafter the ARC signals), (1) the address of the array storage section 70 currently being updated for specifying into which array storage location the updated elemental image signal is to be written, and (2) the address of the next array storage location corresponding to the next point Aij to be updated. The SA/O lines 242 are connected to the scan address register 92 and to the scan origin register 90 for coupling to the selector 226 the address of the next scan storage location to be considered.

The selector 226 also has its input terminals connected to the lines 244, 246, respectively for receiving READ1, WRITE1 signals from the sequential control unit 120. The line 248 is coupled to circuit ground to define a HALFWORD and MODE signal which defines the sixteen-bit operation (as opposed to the thirty-two bit "word" operation of the INTERDATA 7/32 computer) on the DMA bus 80. The selector 226 has an enable terminal coupled to receive a SELSCANADDRESSO signal on a line 250 from the sequential control unit 120.

The selectors 224, 226 are each six, quad 2/1 data selectors commercially available from Texas Instruments, Inc. under Model No. 74S157. The bus transceivers 222 are six, quad bus transceivers commercially available from Advanced Micro Devices, Inc. under Model No. 26S12.

The DMA bus control 220 is shown in FIGS. 8a-8l. The control 220 is responsive to timing commands (indicated generally at 258 in FIG. 7) from the sequential control unit 120 for initiating direct memory access requests the general processor 40 in order to acquire scan and array values from the storage sections 58, 70 of the general processor 40 and in order to return the results of a back projection to the array storage section 70.

Figure 8A:
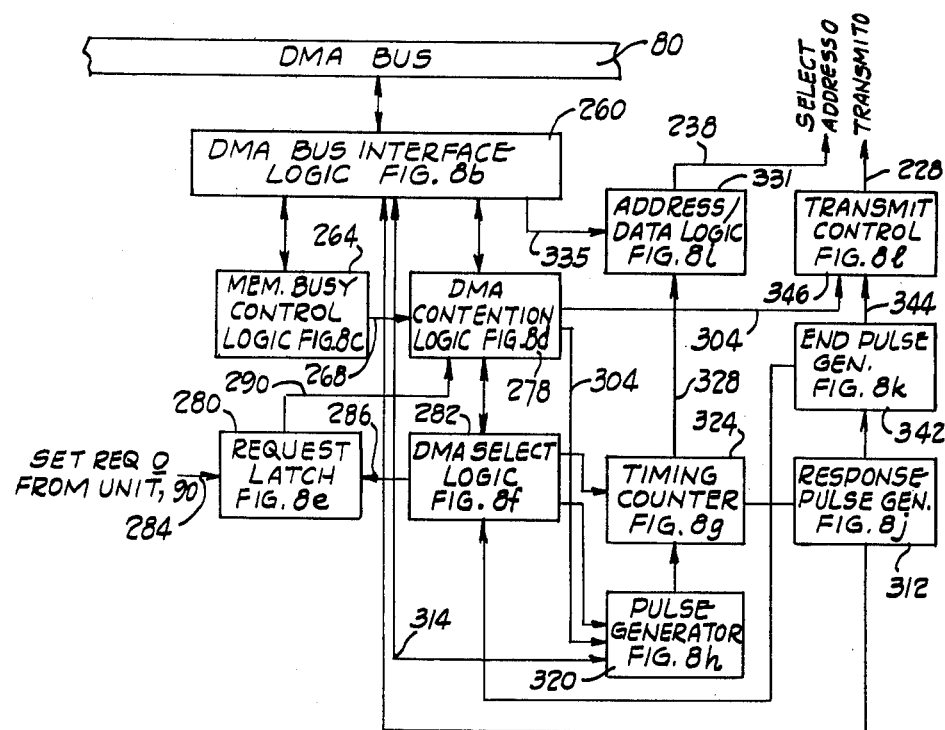
FIG. 8a is a functional block diagram of FIGS. 8b-8f which are detailed circuit schematics of control circuitry for the direct memory access input/output unit of FIG. 7.
Figure 8B:
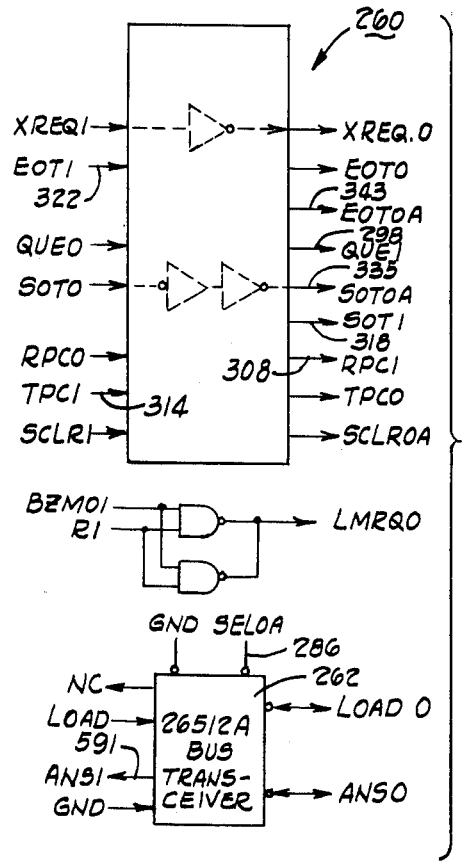
Figure 8C:
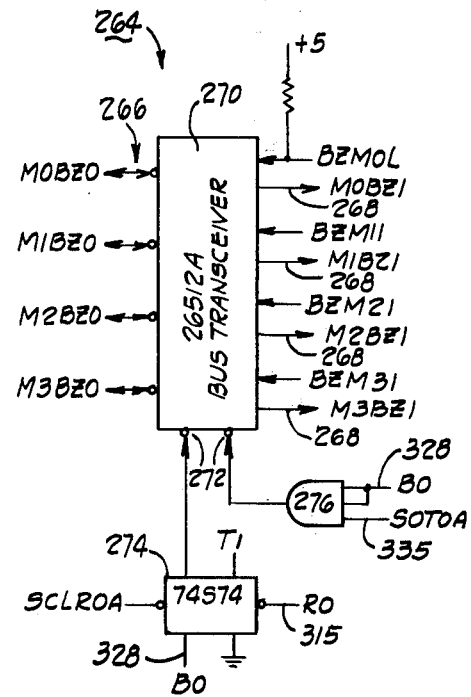

The DMA bus control 220 is shown in detail in FIGS. 8a-8l. FIG. 8a is a functional representation of the bus control 220, and FIGS. 8b-8l are circuit schematics depicting each of the functional representations in FIG. 8a. The specific implementation shown in FIGS. 8b-8l is for the Interdata 7/32 extended DMA bus, although most presently available minicomputers are similar in general function.

The DMA bus control 220 includes a DMA bus interface logic circuit 260 (shown in detail in FIG. 8b) which directly interfaces with the DMA bus 80. The logic circuit 260 is primarily provided to accomplish line driving and receiving and is designed according to recommended procedures specified in Interdata documentation. Via the logic circuit 260, a plurality of signals listed in Tables 4 and 5 are transmitted to the general processor 40 and are received from the general processor 40. Namely, an XREQI signal is transmitted to the processor 40 whenever the special processor 42 is requesting control of the DMA bus 80 for direct memory access. An EOTO signal is transmitted to the general processor 40 when the special processor has finished transmitting its scan storage and array storage address information and its updated elemental image signal information. A QUEO signal is received by the circuit 260 whenever, in response to a XREQI priority request by the special processor, the general processor 40 gives direct memory access to the special processor. A SOTO signal is received by the logic 260 whenever the general processor 40 begins transmission of the scan data signals and the elemental image signals to be updated. An LMRQO signal is transmitted by the logic 260 after the special processor 42 has accepted direct memory access control. An RPCO signal is received by the circuit 260 when the general processor 40 is establishing priority for direct memory access control by devices peripheral to the general processor 40, such as the special processor 42. A TPCO signal is transmitted to the processor 40 whenever the special processor 42 has completed its task and is passing priority elsewhere. A LOADO signal is transmitted to the general processor 40 for instructing the processor 40: (1) to accept address data, and then (2) to accept the updated elemental image signal data. An ANSO signal is received by the circuit 260 when the general processor 40 is conveying the .Vij values and the values of the elemental image signals which were previously addressed. The LOADO and the ANSO signals are transmitted and received via a transceiver 262. A SELOA signal (which is described subsequently) determines whether the transceiver 262 is in the transmit or receive mode.

The signals described with respect to the DMA bus interface logic circuit 260 are the control signals utilized by and produced by circuits shown by the FIGS. 8c-8l. The circuits produce the TRANSMITO signal on the line 228 and the SELECT ADDRESSO signal on the line 238. These circuits are logic circuits which are designed to implement a control sequence according to Interdata specifications.

In more detail, a memory busy control logic circuit 264 (FIG. 8c) is provided to sense (via MOBZO -M3-BZO signals on a set of lines 266) the status of four possible memory banks (M0, M1, M2, M3) in the general processor 40. When finding a memory bank in the general processor 40 which is busy, the control logic circuit 264 asserts a busy signal (a set of BZM01 – BZM31 signal on a set of lines 268) indicative that the particular memory bank is busy. In the illustrated and preferred embodiment, only one memory bank, memory M0, is utilized. The other memory banks and associated circuitry are provided for future expansion of the general processor 40.

The control logic circuit 264 includes a transceiver 270 for receiving the MOBZ0 signal and for transmitting the BZM01 signal. The transceiver 270 has a pair of enable terminals 272 which determine whether the transceiver 270 is to receive or transmit signals. If both of the terminals 272 have logic zero states supplied to them, the transceiver is in a transmit state and vice versa. One of the terminals 272 is coupled to a D-type flip-flop 274, and the other terminal 272 is coupled to an AND gate 276. Operation of the gate 276 and the flip-flop 274 is described subsequently.

A DMA contention logic circuit 278 is provided for resolving conflicts which arise when several devices peripheral to the general processor 40 request direct memory access control simultaneously. The DMA contention logic circuit 278 is coupled to a DMA request latch 280 and to a DMA select logic circuit 282. The DMA request latch 280 is a latch circuit which is set by a SETREQ0 signal on a line 284 from the sequential control unit 120. The latch 280 is reset by an SEL0 signal on a line 286 from the DMA select logic circuit 282. The latch 280 is also reset by a STOP0 signal on a line 288 from the sequential control unit 120.

When the SETREQ0 signal sets the latch 280, a REQ1 signal is generated on a line 290 and a REQ0 signal is generated on a line 292.

The DMA contention logic circuit 278 includes an AND gate 294 having inputs coupled to the lines 286, 290 and through an inverter to the line 268 carrying the MOBZ1 signal. Whenever the latch 280 is set via the SETREQ0 signal to produce the REQ1 signal in the absence of the memory M0 being busy, and in the absence of the DMA select logic circuit 282 having generated the SEL0 signal, AND gate 294 generates the XREQ1 signal signifying that the special processor 42 is requesting direct memory access from the general processor 40. The XREQ1 signal is coupled to the DMA bus interface logic 260 for transmission to the general processor 40 and is coupled to a "Q"-flip-flop 296 in the DMA contention logic circuitry 278.

In response to the XREQ0 signal, the general processor 40 generates the QUE0 signal and transmits it to the DMA bus interface logic circuit 260. In response thereto the circuit 260 generates the QUE1 signal on line 298 to the Q flip-flop 296 causing it to be conditioned into the SET state, generating a Q1 signal on a line 300.

The logic circuit 278 also includes an "S" flip-flop 302 (a D-type flip-flop) having its DATA input coupled to a line 300 for receiving the Q1 signal. The TRIGGER input of the S flip-flop 302 is coupled to the line 298 via an inverter to cause the flip-flop 302 to be set into a logic one state by the trailing edge of the QUE1 signal in the presence of the Q1 signal. Setting of the S flip-flop 302 generates an S1 signal on a line 304.

The S1 signal is transmitted to a gate in the DMA response pulse generator 312. The gate is also responsive to an ANS1 signal from the transceiver 262 for generating a LOAD MEM REG 0 signal on a line 305. The LOAD MEM REG 0 signal causes loading of the data memory register 113 with the RDMA/X signals on the lines 232. The ANS1 signal is generated when the general processor 40 indicates that the data from the storage sections is valid on the bus 80.

The DMA contention logic circuit 278 includes an "R" flip-flop 306 (another D-type flip-flop). The R flip-flop 306 has its DATA input coupled to the line 304 for receiving the S1 signal and has its TRIGGER input coupled to the DMA bus interface logic circuit 260 for receiving the RPC1 signal on a line 308.

The RPC0 signal is generated by the general processor 40 after it has generated the QUE0 signal. The general processor 40 transmits the RPC0 signal sequentially to all peripheral devices which may seek direct memory access. The special processor 42 is arranged to receive the RPC0 signal first (is physically located to receive the RPC0 signal before any other peripheral device) and accordingly is offered top priority for obtaining direct memory access control. When the general processor 40 generates the RPC0 signal, the RPC1 signal is generated on the line 308, setting the R flip-flop 306 and producing an R1 signal on a line 310 and an R0 signal on a line 315. The R0 signal is coupled to the transceiver 270 for providing a logic zero to one of the terminals 272, conditioning the transceiver 270 to be rendered into the transmit mode when a B0 signal is generated to the gate 276.

A DMA response pulse generator 312 (shown in FIG. 8j) is also responsive to the RPC1 signal on the line 308. If the S1 signal on the line 304 has not been generated, indicating that the special processor 42 has not requested direct memory access control, then a TPC1 signal is generated on a line 314 to the DMA bus logic interface circuit 260. The TPC0 signal is then transmitted onto the DMA bus 80 in a logic state which indicates whether the next in-line peripheral device is to be offered control of the direct memory access. If the S flip-flop 302 has been set, the TPC1 signal on the line 314 is generated in a logic one state, preventing the propagation of the TPC0 signal on the bus 80 to other peripheral devices.

Figure 8D:
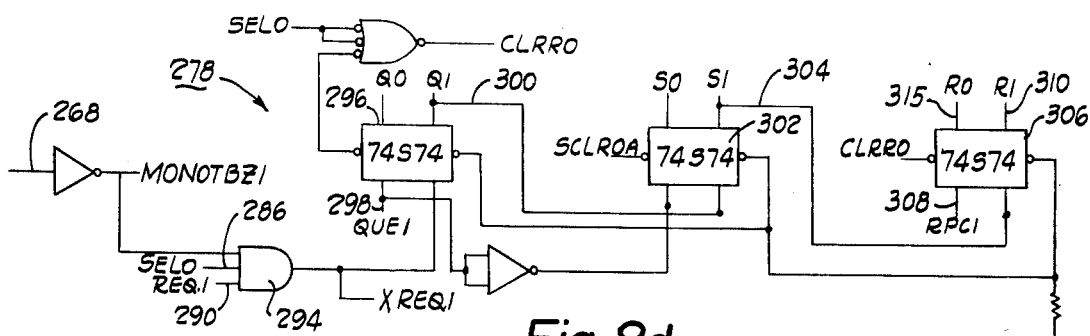
Figure 8E:
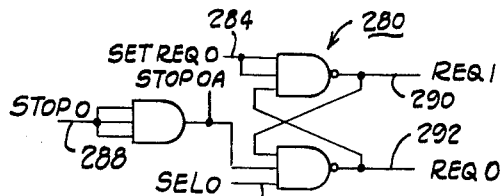
Figure 8F:
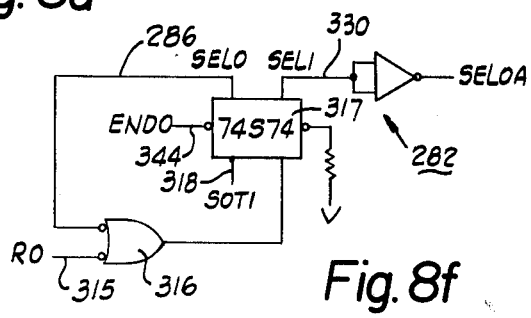

Referring again to the DMA select logic circuit 282 in FIG. 8f, the setting of the R flip-flop 306 (FIG. 8d) generates an R0 signal on a line 315 which is input to the gate 316. The logic circuit 282 includes a SEL flip-flop 317 (of the D-type) having its DATA input coupled to the gate 316. The R0 signal on the line 315 is transmitted through the gate 316 to the DATA input of the flip-flop 317. The TRIGGER input of the flip-flop 317 is coupled by a line 318 to the DMA bus interface logic circuit 260 for receiving an SOT1 signal. The SOT1 signal is generated in response to the general processor 40 as soon as the processor 40 is ready to receive address information from the special processor 42 in the case of a READ or address and data in the case of a WRITE. Generation of the SOT0 signal by the processor 40 causes the SOT1 signal on the line 318 to set the SEL flip-flop 317.

Setting of the SEL flip-flop 317 generates the SEL0 signal on the line 286, which is also coupled as an input to the gate 316. This maintains the set state of the SEL flip-flop 317 and disables the gate 294 of the DMA contention logic 278 (FIG. 8d). The setting of the flip-flop 317 also generates a SELOA signal which is connected to the transceiver 262 for rendering it into a transmit mode.

Generation of the SEL0 signal also resets or clears the DMA request latch 280 (FIG. 8e). This allows other peripheral devices to request direct memory access control, even though the general processor 40 will not grant the request until the special processor 42 has completed its DMA transaction.

Figure 8G:
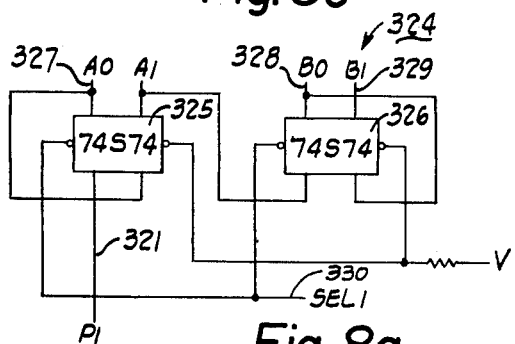
Figure 8I:
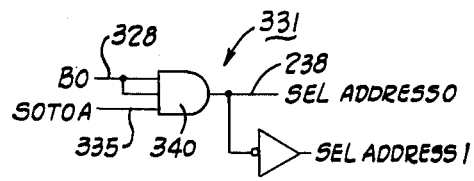
Figure 8J:
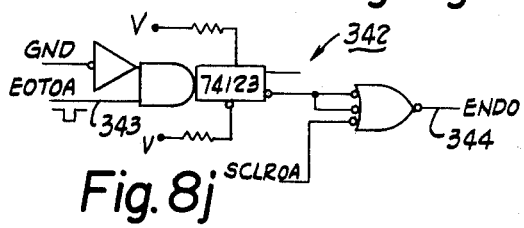
Figure 8H:
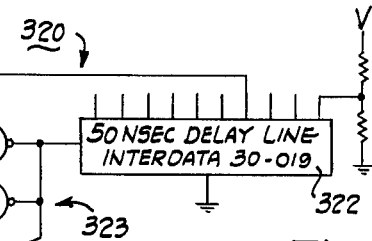

The DMA bus control circuit 220 also includes a timing pulse generator 320 which is shown in FIG. 8h. The timing pulse generator 320 is responsive to setting of the SEL flip-flop 317 (to the SEL0 signal on the line 286) for generating a series of P1 pulses on a line 321. The timing pulse generator 320 includes a 50-nanosecond delay line 322 and a latch circuit 323 which are operable to cause the pulses P1 to be generated on the line 321 at approximately a 20-megahertz repetition rate.

The DMA bus control circuit 220 also includes a DMA timing counter 324 which is shown in detail in FIG. 8g. The DMA timing counter 324 includes an "A" flip-flop 325 and a "B" flip-flop 326. The flip-flops 325, 326 are D-type flip-flops and are series connected as a binary counter for respectively producing A0, B0 timing pulses. The A flip-flop 325 has its TRIGGER input coupled to the line 321 so that the A0, B0 pulses are generated at ten and five megahertz repetition rates, respectively. The A0 and B0 pulses are generated on lines 327 and 328 respectively and a B1 signal is generated on a line 329. The flip-flops 325, 326 are reset or cleared upon clearing of the SEL flip-flop 317 (FIG. 8f) which generates a SEL1 signal on a line 330.

The A0, B0 pulses are transmitted to the DMA response pulse generator 312 (FIG. 8k) and to an address-/data logic circuit 331 (FIG. 8i). The DMA response pulse generator 312 includes a set of logic gates which generate an EOT1 signal on a line 332 and a LOAD1 signal on a line 333. The LOAD1 signal is generated by a gate 334 which has inputs connected to the SEL1 slignal on the line 330, to the A0 signal on the line 327 and to the SOTOA signal on a line 335 from the DMA bus interface logic circuit 260. When the SEL flip-flop 317 is set, and when the general processor 40 indicates that data may be transmitted onto the DMA bus 80, the first occurrence of an A0 pulse generates the LOAD1 signal. The LOAD1 signal on the line 333 is transmitted to the DMA bus interface logic circuit 260 for transmission to the general processor 40, indicating that the general processor 40 is to accept the data on the bus 80. During read operations, the LOAD1 signal is generated concurrently with the EOT1 signal to signify that the special processor is expecting a single memory transaction. This this end, the READ1 signal on the line 244 and the B1 pulse on the line 329 and the SEL1 signal on the line 330 are input to a gate 336. This causes a gate 337, which is also coupled to the output of the gate 334, to produce the EOT1 signal concurrently with the LOAD1.

Also, the pulse B0 on the line 328 is coupled to the gate 276, as is the SOTOA signal on the line 335 for providing a logic zero to the one of the terminals 272. The B0 pulse is also connected to the TRIGGER input of the flip-flop 274 for insuring a logic zero condition to the terminals 272. When both of the terminals 272 are in the logic zero state, the transceiver 270 transmits a "memory busy" signal to the general processor 40.

During the WRITE operations when the special processor 42 first sends an array storage address and then sends the updated elemental image signal, the EOT1 signal is generated concurrently with the second of first and second successively transmitted LOAD1 pulses. To this end a gate 338 is responsive to the inverse of the READ1 signal on a line 339, to the B0 pulse on the line 328 and to the SEL1 signal on the line 330. The gate 338 effects a logic one condition upon the input of the gate 337 concurrently with the occurrence of the second LOAD1 signal to produce the EOT1 signal concurrently therewith. The gate 338 effects this operation because two A0 pulses occur while one B0 pulse occurs.

The address/data logic 331 includes a gate 340 which is responsive to the B0 pulse on the line 328 and to the SOTOA signal on the line 335 for producing the SELADDRESS0 signal on the line 238. The SELADDRESS0 signal is coupled to the data selector 224 for determining whether the TDMA/X signal is indicative of an address on the ADM lines 236 or an updated elemental image signal on the A lines 234.

An end pulse generator 342 is provided and is shown in detail in FIG. 8j. The end pulse generator 342 is a one shot generator which is triggered by an EOTOA signal on a line 343 for generating an END0 signal on a line 344. The EOT1 signal which is provided to the DMA bus interface logic circuit 260 causes the EOTOA signal on the line 343 to be generated. Generation of the END0 signal is indicative that the particular memory transaction has been completed and that the DMA bus control 220 should be reset in anticipation of another transaction. The END0 signal 344 is transmitted to the DMA select logic circuit 282 for clearing the SEL flip-flop 317.

Figures 8K, 8L:
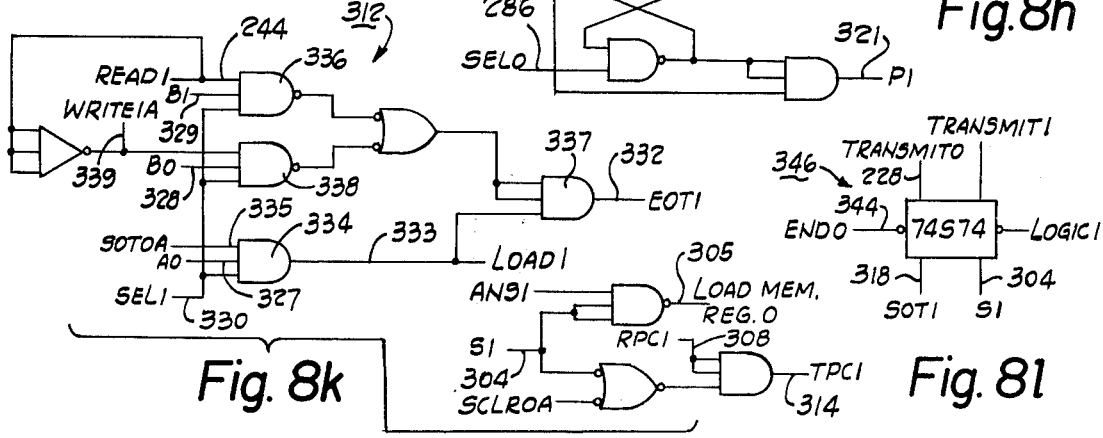

A DMA transmit control 346 is provided as part of the DMA bus control 220 for producing the TRANSMIT0 signal on the line 228 to the transceiver circuit 222. The TRANSMIT0 signal determines whether the transceiver circuit 222 is in the transmit or receive mode. The DMA transmit control 346 is shown in FIG. 8l and includes a D-type flip-flop having its DATA input coupled to the line 304 for receiving the S1 signal. The TRIGGER input is coupled to the line 318 so that the TRANSMIT0 signal on the line 228 is generated whenever the S flip-flop 302 (FIG. 8d) is set and whenever the general processor 40 indicates that data may be transmitted on the bus 80. The flip-flop is cleared for disabling the transceiver circuit 222 via the END0 signal on the line 344.

The Accumulator Unit 114

Figure 9:
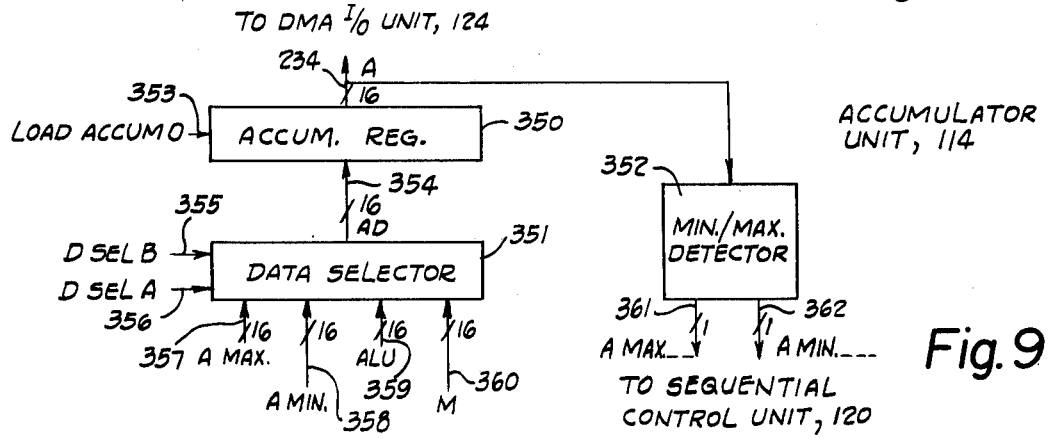
FIG. 9 is a functional diagram of an accumulator unit utilized in the special processor of FIG. 4.

Referring now to FIG. 9, the accumulator unit 114 includes an accumulator register 350, a data selector 351 and a min/max detector 352. The accumulator register 350 is enabled by a LOAD ACCUM0 signal on a line 353 from the sequential control unit 120 to receive a set of signals on a set of lines 354 from the data selector 351. The accumulator register 350 comprises four, quad D-type flip-flops which provides the sixteen-bit A signals on the lines 234.

The data selector 351 selectively generates a set of ADxx1 signals (hereafter the AD signals) on the lines 354 according to whether it is enabled by a DSELB signal on a line 355 or by a DSELA signal on a line 356. The DSELB and DSELA signals are generated via the sequential control unit 120.

The data selector 351 comprises eight, dual, 4/1 data selectors. The selectors have inputs for receiving four, sixteen-bit input signals. The four input signals are AMAXxx1 (hereafter the AMAX signals); AMINxx1 (hereafter the AMIN signals); ALUxx1 signals (hereafter the ALU signals); and Mxx1 signals (hereafter the M signals). The AMAX signals are preestablished to provide a value on a set of lines 357 which represent a maximum value for the updated elemental image signal.

In the preferred embodiment the AMAX signal represents a value of plus 32000 (to the base 10).

The AMIN signals are preestablished to provide a minimum value on a set of lines 358. In the preferred embodiment the value provided by the AMIN signals is minus 32000 (to the base 10).

The ALU signals are provided on a set of lines 359 from the processing unit 98. The ALU signals represent the value of the updated image signal which is to be written into the array storage section 70.

The M signals are generated on a set of lines 360 from the memory data register 118. The M signals coupled to the selector 351 are the RDMA/X signals representing the value of the elemental image signal c1) transmitted from the array storage section 70 which is to be updated by a particular value Vij from the scan storage section 58, and c2) which is written into the memory data register 118.

The MIN/MAX detector 352 is a conventional logic circuit which interrogates the A signals on the lines 234 to see whether the value of the sixteen bits comprising the A signal equals the preestablished maximum value (32000) or the preestablished minimum value (−32000). The detector 352 generates an AMAX1 signal on a line 361 and an AMIN1 signal on a line 362 if, respectively, the A signals exceed the maximum or minimum values. The AMAX1 and AMIN1 signals are coupled to the sequential control unit 120.

The Processing Unit 98

Figure 10:
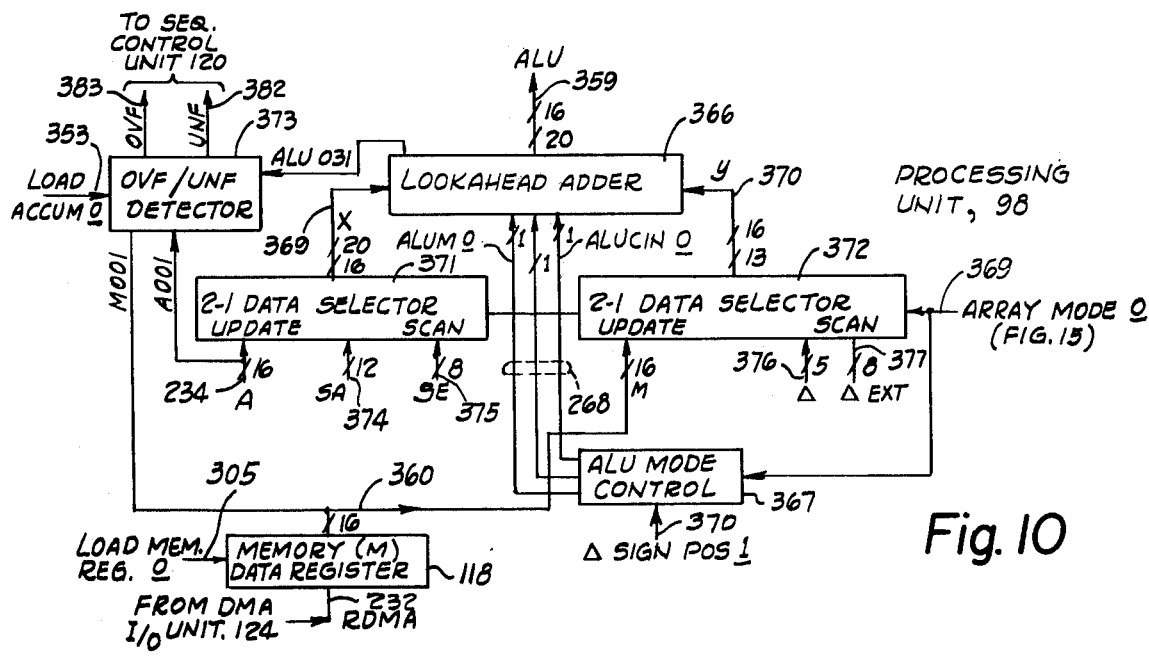
FIG. 10 is a functional diagram of a processing unit utilized in the special processor of FIG. 4.

Referring now to FIG. 10, the processing unit 98 includes a carry look-ahead adder 366 which is coupled to a mode control 367 by a set of lines 368. Depending on the signals generated on the lines 368 by the mode control 367, the adder 366 either adds or subtracts data signals on a set of X data lines 369 and on a set of Y data lines 370.

Referring to FIG. 11a, the adder 366 and the mode control 367 are shown in detail. The adder 366 comprises five, Model 74S181 arithmetic logic units from Texas Instruments, Inc. which are connected to provide a twenty-bit twos-complement adder. Model 74S182 look-ahead carry generators from Texas Instruments, Inc. are connected to the five arithmetic logic units according to prescribed specifications to implement a carry look-ahead adder.

The mode control 367 includes a set of logic gates which provide ALUM0 and ALUNCIN0 signals on the lines 268. The ALUM0 signal is invariably a logic zero to specify an arithmetic mode of operation to the arithmetic logic units. The ALUCIN0 signal represents a carry input supplied to the five arithmetic logic units.

The logic gates of the mode control 367 are responsive to a SCAN MODE1 signal on a line 369 from the sequential control unit 120 and to a Δ SIGN POS1 signal on a line 370 from the delta scan address register 96. Generation of these signals is respectively shown in FIG. 15 and in FIG. 12.

Referring again to FIG. 10, the processing unit 98 also includes an X data selector 371, a Y data selector 372, and an overflow/underflow detector 373. The selectors 371, 372 each comprise five of the Model No. 74S157 quad 2-1 data selectors. The X data selector 371 has a sixteen-bit input coupled to the lines 234 for receiving the A signals from the accumulator register 350 and has a twenty-bit input coupled to the scan address register 92 and to the scan address extension register 94 via sets of lines 374, 375 respectively. The lines 374 receive twelve bits of a signal SAxx1 (hereafter referred to as the SA signals) and the lines 375 receive eight bits of a signal SExx1 (hereafter referred to as the SE signals). The SA signals and the SE signals define a twenty-bit scan address utilized in determining the location within scan storage section 58 of the relevant Vij value.

The Y data selector 372 has a sixteen-bit input coupled to the lines 360 for receiving the M signals from the memory data register 118 and has a thirteen-bit input coupled to the delta scan address register 96 via sets of lines 376, 377. The lines 376 are coupled to receive the five most significant bits of the DELTA value, and the lines 377 are coupled to receive the eight least significant bits of the DELTA value. The most significant bits and the least significant bits are respectively denoted by DELTAxx1 hereafter the DELTA signals) and by the DELTA EXTxx1 signals (hereafter the DELTA EXT signals). The selectors 371, 372 are coupled to receive an ARRAY MODE0 signal (which is the same signal as the SCAN MODE1 signal) transmitted on the line 369 from the sequential control unit 120. The ARRAY MODE0 signal determines (1) whether the X selector transmits the A signals on the sixteen-bit input while the Y selector transmits the sixteen-bit M signals, or (2) whether the X selector 371 transmits the twenty bits of the SA and SE signals while the Y data selector 372 transmits the sixteen bits of the DELTA and the DELTA EXT signals.

The overflow/underflow detector 373 is another timesaving feature of the invention. It performs its underflow/overflow detection in a near minimum amount of time, and is adapted to perform its operation in parallel, i.e., concurrently, with other operations on the special processor 42. The overflow/underflow detector 373 is shown in detail in FIG. 11b.

The detector 373 includes an "OK" flip-flop 380 and a "carry" flip-flop 381 in combination with logic gates which provide a UNF1 signal on a line 382 and an OVF1 signal on a line 383. The carry flip-flop 381 is set to indicate whether there was a carry out of the adder 366. The OK flip-flop 380 is set to indicate when neither overflow nor underflow conditions have been encountered. This is upon the condition that the signs of the operands are different. If the OK flip-flop 380 remains cleared, indicating that the signs of the operand are the same, the possibility of either underflow or overflow exists. For this condition the value of the "same" sign of the operand is compared with the sign of the result. Only if the signs are different has either overflow or underflow occurred. For this condition, if the carry flip-flop is set to indicate the occurrence of a carry, then underflow occurred; if no carry occurred, overflow occurred.

The flip-flops 380, 381 have their TRIGGER input terminals coupled to receive the LOAD ACCUM0 signal on the line 353 from the sequential control unit 120. The OK flip-flop 380 has its DATA input terminal coupled via a line 384 to an exclusive-OR circuit 385. The exclusive-OR circuit 385 has a pair of inputs coupled to receive the A001 signal on the line 234 and to receive the M001 signal on the line 360. The A001 and the M001 signals are the sign bits of the A and M signals, respectively. Whenever the A001 and the M001 signals are unequal, a logic one is generated on the line 384, setting the OK flip-flop 380 upon the occurrence of the LOAD ACCUM0 signal. Setting of the OK flip-flop 380 produces an OKFF0 signal on a line 386, preventing generation of the UNF1 and the OVF1 signals.

If the exclusive-OR circuit 385 generates a zero on the line 384, indicating that the signs of the A and M signals are the same, the OK flip-flop 380 remains cleared, generating a logic one on the line 386. As soon as the adder 366 has completed its task, then the result is written into the accumulator unit 114, and the A001 bit becomes the sign bit of the result. Accordingly, the circuit 385 compares the sign bit of the result with the sign bit of the operands, and, if they are the same, generates a logic zero on the line 384 for preventing generation of the UNF1 and OVF1 signals.

If the signs of the result and of the operands are different, a set of lines 387, 388 determines which of the overflow or underflow conditions occurred. Specifically, if a carry occurred, the ALV031 bit on the line 359 sets the carry flip-flop 381 upon the occurrence of the LOAD ACCUM0 signal on the line 353. Setting generates a logic zero on the line 388, determining overflow. If no carry occurred, the carry flip-flop generates a logic zero on the line 387, determining underflow.

Figure 12:
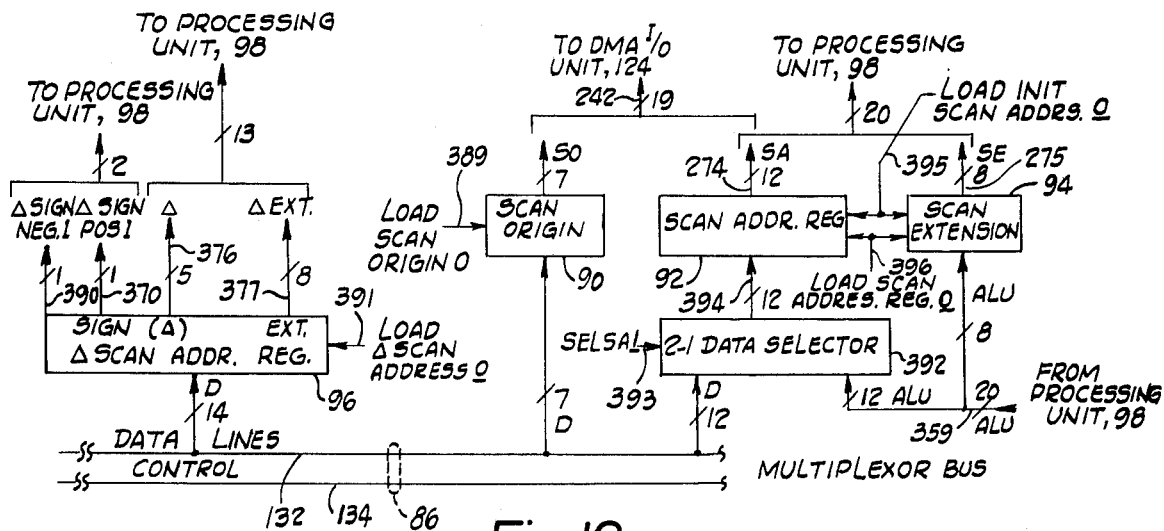
FIG. 12 is a functional diagram of registers which are utilized in a scan address calculator in the special processor of FIG. 4.

The registers 90, 92, 94, 96 are shown in more detail in FIG. 12. The scan origin register 90 and the delta scan address register 96 are directly coupled to the data lines 132 for respectively receiving the location of the origin 77 of the SCAN($\theta i$) and the value of the DELTA increment. To this end the scan origin register 90 is responsive to the D signals for producing the S0 signals which are schematically shown as being transmitted by the line 242 to the DMA I/0 unit 124. The delta scan address register 96 is responsive to the D signals to generate the DELTA EXT signals on the lines 377, the DELTA signals on the line 376, the . $\Delta$ SIGN POS1 signal on the line 370, and a $\Delta$ SIGN NEG1 signal on a line 390. The delta scan address register 96 is enabled to load the D signals via a LOAD $\Delta$ SCAN ADDRES0 signal on a line 391 which is coupled from the multiplexor channel control unit 130. The scan origin register 190 is enabled to receive the D signals by a LOAD SCAN ORIGIN0 signal on a line 389 from the multiplexor channel control unit 130.

The scan address register 92 is associated with a data selector 392. The data selector 392 has one twelve-bit set of inputs coupled to the multiplexor bus 86 for selectively receiving the D signals, and has another twelve-bit set of inputs coupled to the lines 359 for receiving the ALU signals. The data selector 392 is conditioned by a SELSA1 signal on a line 393 which is coupled from the multiplexor channel control unit 130. The twelve-bit D signals represent the address of the scan storage location containing the first relevant value Vij to be used in the update. The twelve-bit ALU signal is representative of the updated scan address which is to be utilized subsequent to the first update for a given row of the array A.

The data selector 392 selects the proper twelve-bit input and transmits it on a line 394 to the scan address register 92. Upon a LOAD SCAN ADDRES REG0 signal on a line 396, which is coupled from the sequential control unit 120, the selected twelve bits are input into the scan address register 92 to define the twelve most significant bits of the next relevant location Lij. This address is output as the SA signal on the line 274. For the first scan address, a LOAD INIT SCAN ADDR0 signal on a line 395 enables input of the twelve bits into the register 92.

The scan extension register 94 has an eight-bit input coupled to the lines 359 for receiving the least significant eight bits of the ALU signal from the processing unit 98. The eight-bit signal is loaded upon the occurrence of the LOAD SCAN ADDRES REG0 signal on the line 396, and is initially set to a value $80_{16}$ by the LOAD SCAN ADDRS0 signal on the line 395. The scan extension register 94 transmits the eight ALU bits as the SE signals on the lines 275 for transmission to the processing unit 98.

Figure 13:
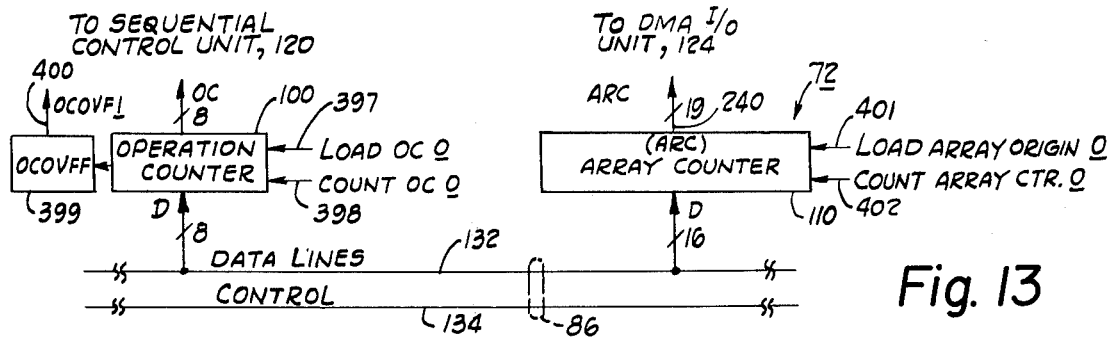
FIG. 13 is a functional diagram of an operation counter and an array counter respectively utilized in the scan address calculator and an array address calculator of the special processor in FIG. 4.

Referring now to FIG. 13, the association of the operation counter 100 and the array counter 110 with the multiplexor bus 86 is shown in more detail. The operation counter 100 is selectively responsive to eight bits of the D signal on the data lines 132 whenever a LOAD OC0 signal is generated on a line 397. This initially loads a value in the operation counter 100 which is indicative of the number of points in a given row of the array A to be updated. The counter 100 is responsive to COUNT OC0 signal on a line 398 which is coupled from the sequential control unit 120 and is generated after each point in the particular row has been updated.

An operation counter overflow flip-flop, OCOVFF, 399 is coupled to the operation counter 100 and is set whenever the operation counter 100 overflows. Overflow of the operation counter 100 indicates that all points in a given row of the array A have been updated, and the flip-flop 399 generates an OCOVF1 signal on a line 400 upon this condition.

The array counter 110 of the array address calculator 72 has a sixteen-bit input coupled to receive the D signals from the multiplexor bus 86 upon the occurrence of a LOAD ARRAY ORIGIN0 signal on a line 401 from the multiplexor channel control unit 130. The counter 110 is coupled to a line 402 and is incremented by a COUNT ARRAY CTR0 signal upon completion of updating for each point in a given row. The contents of the counter 110 is output on the lines 240 as the ARC signal for transmission to the DMA I/0 unit 124.

The array counter 110 comprises five, four-bit up-/down, synchronous counters commercially available under the Model Number 74193 from Texas Instruments, Inc. The operation counter 100 comprises two of the 74193 synchronous counters.

Referring now to FIG. 14a, the multiplexor channel control unit 130 is shown in more functional detail as it provides the mechanism by which the registers 90-96, 122 and the counter 110 are initially loaded by the general processor 40 for initiating back projection. The multiplexor channel control 130 also allows the general processor 40 to sense the status of the special processor 42 to determine completion of the update task.

The control unit 130 includes a set of multiplexor channel data buffers 410 which are shown in detail in FIG. 14b. The data buffers 410 are primarily line drivers and inverters. They received the Dxx0 signals and provide Dxx1 and DxxOA signals which respectively are inverted and noninverted buffered forms of the Dxx0 signals. In a similar manner, the buffers 410 provide inverted and buffered forms of the ADRS0 signal, of the DA0, of the CMD0 signal and of the SR0 signal on the lines 411-418 respectively. These signals have been described with respect to Tables 1 and 3.

The data buffers 410 are coupled to a device address decoder circuit 420 which is shown in detail in FIG. 14c. The device address decoder 420 includes a decode circuit 421, such as a Model Number 7442 decoder commercially available from Texas Instruments, Inc., which is enabled by a DEVADDR03x0 signal on a line 422. Logic circuitry 423 is connected to the line 422 and has inputs coupled to the 6-12 bits of the D signal. The circuitry 423 determines whenever a device address 30-37 has been called up by the general processor 40. More specifically, the 6-8 bits, the 9-11 bits, and the 12-14 bits of the D signals are octal representations of the 03x device location, where x ranges from 0 to 7. When the circuitry 423 generates the DEVADDR03x0 signal, its inverse is generated on a line 424.

Whenever the decode circuit 421 is enabled by the DEVADDR03x0 signal on the line 422, the particular called-up device location is indicated on a set of lines 425 as DD3x0 signals.

Referring to FIG. 14d, a device decoded storage buffer 430 is provided, coupled to the lines 425 for receiving the DD3x0 signals. Because the DD3x0 signals are momentary in nature, and because the decoding of the device location must be preserved, the storage buffer 430 includes a pair of quad D-type flip-flops 431, 432 having their inputs connected to the lines 425. The DD3x0 signals on the lines 425 are entered into the flip-flops 431, 432 whenever the general processor 40 sends over the ADRS0 signal, producing the ADRS1 signal on the line 411. The general processor 40 generates the ADRS0 signal during the execution of any I/0 instruction, instructing the special processor 42 to interpret the data in the form of the D signals on the data lines 132 as a device address. The flip-flops 431, 432 are reset or cleared by the general processor 40 when it sends over the SYSTEM CLEAR signal, SCLR0, on a line 433. The flip-flops 431, 432 provide FDD3xx signals on a set of lines 434 and on the line 393 which indicate the called-up device address location. The FDD3xx signals are latched on the lines 393 and 434 until the general processor 40 sends over a subsequent device address location.

Referring again to FIG. 14a, the lines 434 from the storage buffer 430 are coupled to a multiplexor channel status generator 440 and to a multiplexor channel pulse generator 460. The multiplexor channel status generator 440 senses and transmits busy status and synchronization information to the general processor 40 via the multiplexor bus 86. The multiplexor channel control pulse generator 460 responds to specific device addresses and generates appropriate control pulses to effect the desired input of data at the prescribed address locations and to otherwise effect operations within the special processor 42.

The multiplexor channel status generator 440 is shown in detail in FIG. 14f. It includes an ENABLE flip-flop 441 which is set by an ADDRSYN0 signal on a line 442, and has its reset terminal coupled to a line 443. The ADDRSYN0 signal on the line 442 is generated as a function of the ADRS1 signal on the line 411 and the DEVADDR03x1 signal on the line 424. The flip-flop 441 is set, generating a DENB1 signal on a line 444, whenever one of the device locations 30-37 have been called up. The ENABLE flip-flop 441 is reset whenever any other device address location has been called up. The DENB1 signal on the line 444 is inverted and provided to the general processor 40 as the HW0 signal via line 445.

The HW0 signal signifies that the general processor 40 is to send data in a halfword mode. A halfword is defined as a sixteen-bit word, as the Interdata computer defines a word to be thirty-two bits.

As has been previously described with respect to FIG. 5, the general processor 40 sends over three types of I/0 instructions: write halfword or data instructions, command instructions, and status request instructions. For these instructions the general processor 40 sends over the DA0 signal, the CMD0 signal and the SR0 signal to identify the instruction. The special processor 42 must thereafter communicate to the general processor 40 that it has received the I/0 instruction. To this end the special processor 42 generates internal synchronization pulses which are used to produce the SYN0 synchronization pulse which is transmitted to the general processor 40 via a line 446. The SYN0 pulse on the line 446 is generated upon generation of any of the internal synchronization pulses.

Specifically, the internally generated synchronization pulses include the ADRSYN0 signal on the line 442, a DASYN0 signal on a line 447, a CMDSYN0 signal on a line 448, and a SRSYN0 signal on a line 449. The DASYN0 signal on the line 447 is generated whenever the ENABLE flip-flop 441 has been set to generate the DENB1 signal on the line 444 and whenever the general processor 40 has caused the DA1 signal on the line 413 to be generated. The CMDSYN0 signal on the line 448 is generated whenever the general processor 40 causes the CMD1 signal on the line 415 to be generated and whenever the flip-flop 431 (FIG. 14d) has generated the FDD301 signal on the respective one of the lines 434. The SRSYN0 on the line 449 is generated when the general processor 40 causes the SR1 signal on the line 417 to be generated concurrently with the flip-flop 431 generating the FDD301 signal on the respective one of the lines 434.

Also, as shown in FIG. 14f, the special processor generates a D120 signal on a line 450. This indicates the status of the special processor 42. The status signal is generated according to (1) the inverse of the SRSYN0 signal as transmitted on a line 452, and (2) the state of a RUN1 on a line 453 from the sequential control unit 120 whenever the FDD301 signal has been generated on the respective one of the lines 434.

The multiplexor channel control pulse generator 460 is shown in detail in FIG. 14e. It includes a plurality of gates 461-466 having inputs coupled to various ones of the lines 434 from the device decoded storage buffer 430. The gates 461-465 respectively generate the LOAD DELTA SCAN ADDRS0 on the line 391, the LOAD ARRAY ORIGIN0 signal on the line 401, the LOAD SCAN ORIGIN0 signal on the line 389, the load INIT SCAN ADDR0 signal on the line 395 and the LOADOC0 signal on the line 397. These gates are enabled by the DA1 signal on the line 413.

The gate 466 is also responsive to the DA1 signal on the line 413 and to one of the FDD3xx signals on one of the lines 434 and produces an MPX LOAD CROM ADDRES REG0 signal on a line 467. This signal is transmitted to the sequential control unit 120 and its function will be described subsequently. The 3x representations in each of the FDD3x1 signals indicates which device location was called up by the generator processor 40. The correlation of the resulting output signals from the gate 461-467 to the signals FDD3x1 is seen in Table 2.

The multiplexor channel control pulse generator 460 also includes logic circuitry 470 which generates an INITIATE0 signal on a line 471 and INITIATE1 signal on a line 472, and INITIATE DECODED1 signal on a line 473, and a RESET0 signal on a line 474. The circuitry 470 is responsive (1) to the FDD301 signal on the line 434, (2) to a CMDPLS signal on a line 475 carring the inverse of the CMDSYN0 signal, and (3) to the bits D140A, D151, and D141 from the data buffers 410.

Whenever the device address location 30 has been called up, as indicated by the occurrence of the FDD301 signal on the line 434, and whenever a command I/O instruction has been sent by the general processor 40 as indicated by the CMDPLS signal on the line 475, the general processor 40 is either dictating that the special processor 42 (1) be reset, or (2) initiate back projection. The selection of these functions is determined by the bits 14 and 15 of the D signals, whereby setting of bit 14 generates the reset signal and setting of the bit 15 generates the initiate signal.

The Sequential Control Unit 120

Figure 15:
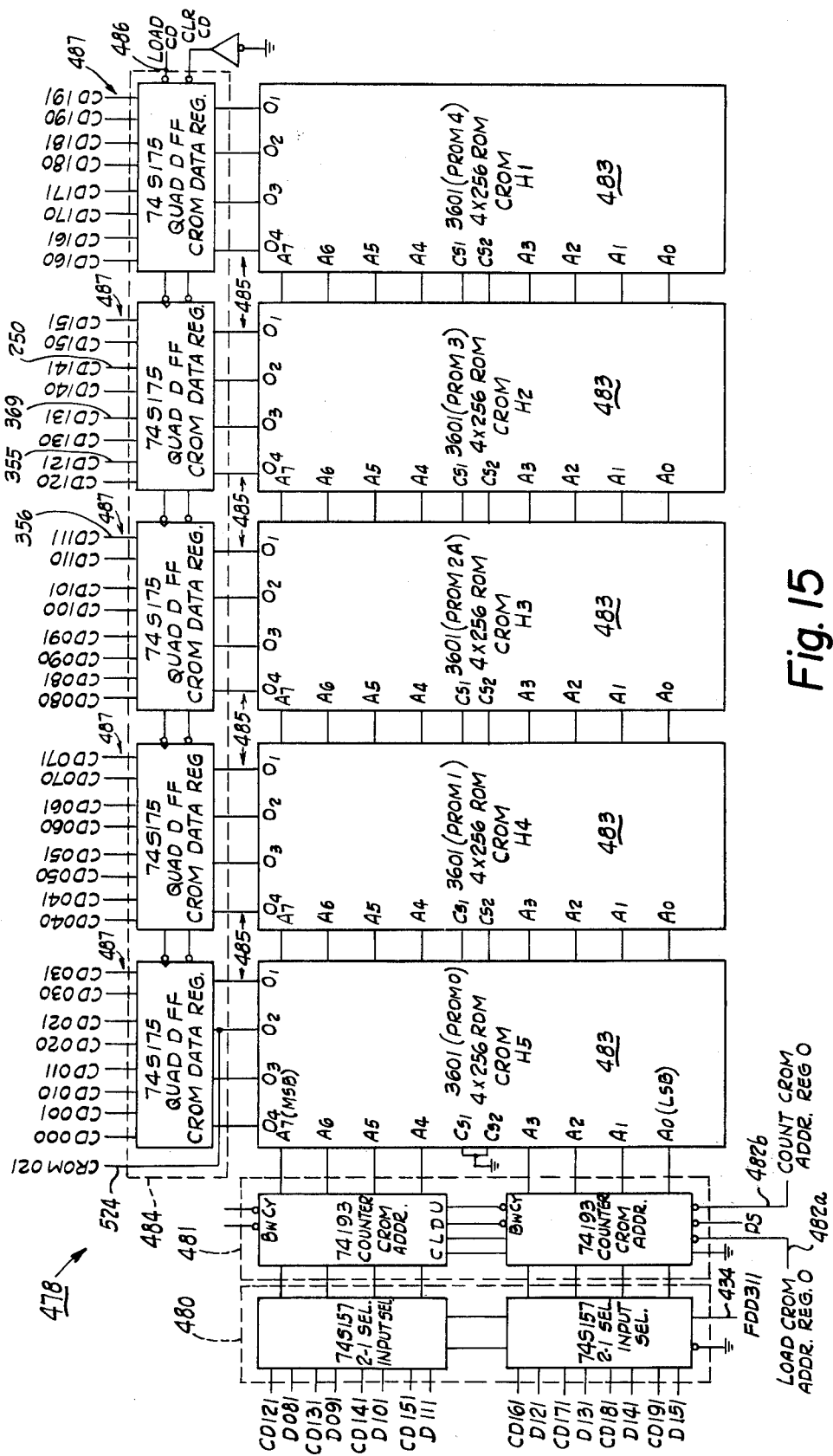
FIG. 15 is a functional diagram of a sequential control unit in the special processor of FIG. 4.

The sequential control unit 120 includes a control memory circuit 478 which is functionally shown in FIG. 15. After the special processor 42 has been initialized by the general processor 40, the control memory circuit 478 controls operations of the special processor 42 for effecting the back projection and updating process.

The control memory circuit 478 includes a data selector 480 having a pair of eight-bit inputs and a control read-only memory address register 481 coupled to the outputs of the data selector 480. The data selector 480 has one of its eight-bit inputs coupled to the data lines 132 of the bus 86 and, upon the generation of the FDD311 signal on one of the lines 434, transmits eight bits of the D signals into the address register 481. Upon generation of a LOAD CROM ADDR REG0 signal on a line 482a, the eight bits of the D signals are entered into the register 481. This signal is utilized initially when the general processor 40 transmits an address dictating the start of the desired operating sequence and is utilized whenever a branch condition has been specified and met. For other operations, a COUNT CROM ADDR REG0 signal on a line 482b is utilized for incrementing the count in the register 481.

A READ-ONLY memory 483 is provided and is connected to the output of the address register 481. The memory 483 sequentially stores a succession of program words which dictate operation of the special processor 42. In the preferred embodiment, the memory 483 comprises five, 1024-bit read-only memories which are commercially available from Intel Corporation under Model No. 3601. The memories are interconnected in a conventional manner to provide storage for 256, twenty-bit program words.

Figure 16J:
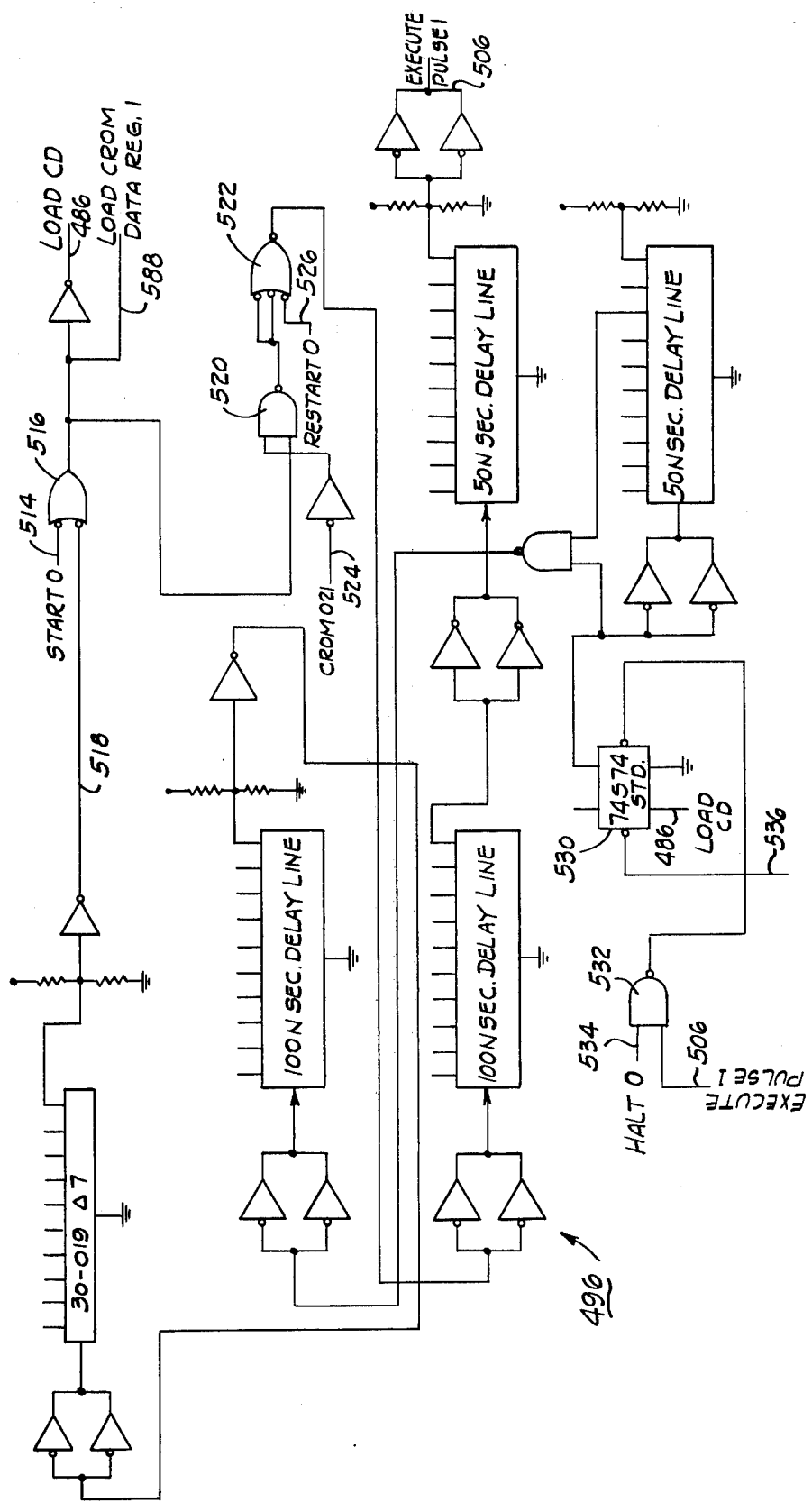
FIG. 16a is a functional block diagram of FIGS. 16b–16j which are detailed, sectioned circuit schematics of control circuits utilized in the sequential controller of FIG. 17.

A data register 484 is coupled via a set of lines 485 to the output of the read-only memory 483. The data register 484 comprises five, quad D-type flip-flops, one for each of the Model 3601 read-only memories. The data register 484 is enabled by a LOAD CD signal on a line 486. The data register 484 has a set of output lines 487 for producing a set of output signals CDxxx (hereafter the CD signals. The CD signals are transmitted to the other eight-bit inputs of the data selector 480 and are transmitted to a sequence control signal generator 490 (FIG. 16).

In operation, the eight bits of the D signal which are stored in the address register 481, address a specific location within the memory 483. This causes the addressed program word to be output by the set of lines 485 into the data register 484 for transmission as the CD signals.

Figure 17:
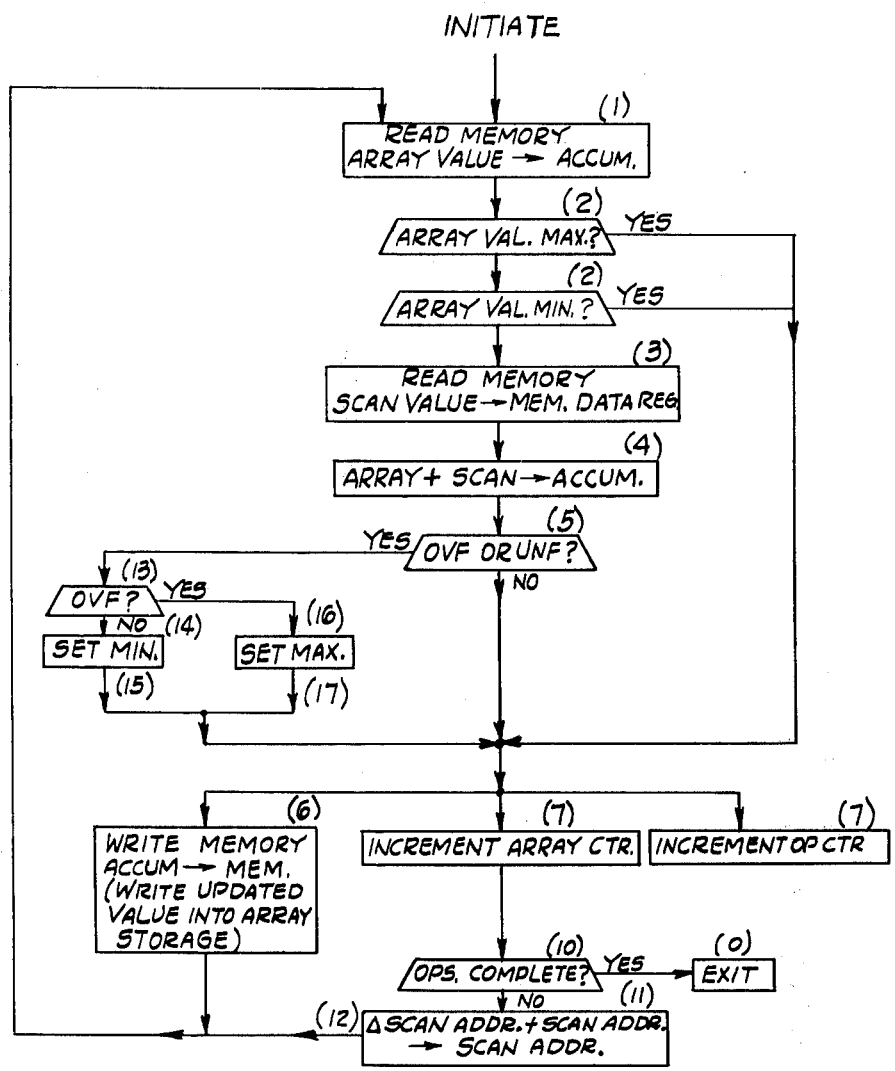
FIGS. 17, 18 are alternate flow diagrams characterizing programming of a memory unit of the sequential control unit of FIG. 15; and, FIG. 19 is a functional diagram of a control Read-only memory (ROM) of the sequential control unit of FIG. 15.
Figure 18:
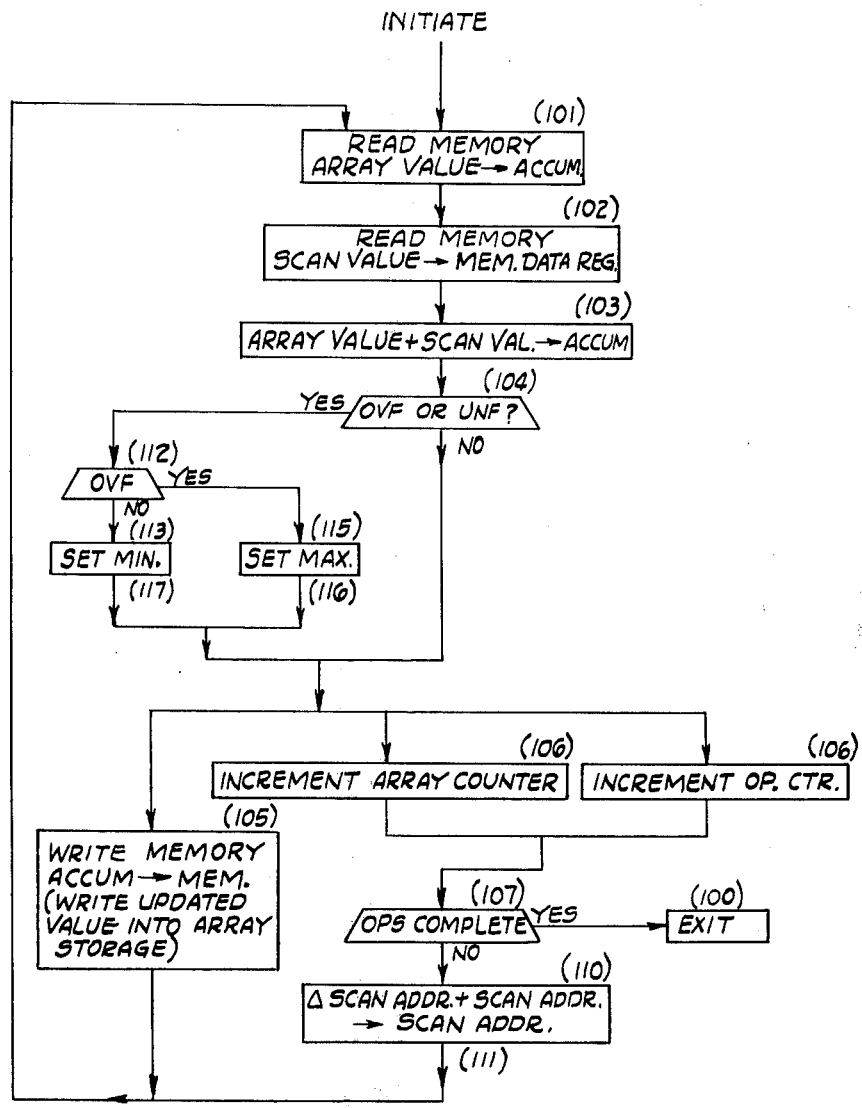

The read-only memory 483 is programmed with the succession of program words to effect one of the two flow diagrams shown in FIGS. 17 and 18. The flow diagrams in FIGS. 17 and 18 are specific implementations of the flow diagram previously described with respect to FIG. 6 and OPTION 1 and OPTION 2. Except for mentioning that the stored program word which implements the listed function in FIGS. 17, 18 is parenthetically given for the particular function, further description is unneeded. The specific ROM coding used for implementing the flow diagrams in FIGS. 17 and 18 are respectively set forth in Tables 6 and 7 below.

TABLE 6

| | | Option 1 Microprogram | | | | | | | | | | | | | | | | | | |
|---|---|---|---|---|---|---|---|---|---|---|---|---|---|---|---|---|---|---|---|---|
| | | PROM 0 | | | | PROM 1 | | | | PROM 2A | | | | PROM 3 | | | | PROM 4 | | |
| OCTAL | | OP | | W | R/W | CONTROL | | | | | | | | | | | | | | |
| ADDRESS | INSTR. | 00 | 01 | 02 | 03 | 04 | 05 | 06 | 07 | 08 | 09 | 10 | 11 | 12 | 13 | 14 | 15 | 16 | 17 | 18 | 19 |
| 000 | HLT | 0 | 0 | 0 | 0 | 0 | 0 | 0 | 0 | 0 | 0 | 0 | 0 | 0 | 0 | 0 | 0 | 0 | 0 | 0 | 0 |
| 001 | EXC | 0 | 1 | 1 | 0 | 0 | 0 | 1 | 0 | 0 | 0 | 0 | 1 | 1 | 0 | 1 | 0 | 0 | 0 | 0 | 0 |
| 002 | BRN MIN/MAX | 1 | 0 | 0 | 0 | 1 | 1 | 0 | 0 | 0 | 0 | 0 | 0 | 0 | 0 | 0 | 0 | 0 | 1 | 1 | 1 |
| 003 | EXC | 0 | 1 | 1 | 0 | 0 | 0 | 0 | 0 | 0 | 0 | 0 | 0 | 1 | 0 | 0 | 0 | 0 | 0 | 0 | 0 |
| 004 | EXC | 0 | 1 | 0 | 0 | 0 | 0 | 1 | 0 | 0 | 0 | 0 | 0 | 1 | 0 | 1 | 0 | 0 | 0 | 0 | 0 |
| 005 | BRN OVF/UNF | 1 | 0 | 0 | 0 | 0 | 0 | 1 | 1 | 0 | 0 | 0 | 0 | 0 | 0 | 0 | 0 | 1 | 0 | 1 | 1 |
| 006 | EXC | 0 | 1 | 1 | 1 | 0 | 0 | 0 | 0 | 0 | 0 | 0 | 0 | 0 | 1 | 0 | 0 | 0 | 0 | 0 | 0 |
| 007 | EXC | 0 | 1 | 0 | 0 | 1 | 0 | 0 | 1 | 0 | 0 | 0 | 0 | 1 | 0 | 0 | 0 | 0 | 0 | 0 | 0 |
| 010 | BOPC | 1 | 0 | 0 | 0 | 0 | 0 | 0 | 0 | 1 | 0 | 0 | 0 | 0 | 0 | 0 | 0 | 0 | 0 | 0 | 0 |
| 011 | EXC | 0 | 1 | 0 | 0 | 0 | 1 | 0 | 0 | 0 | 0 | 0 | 0 | 1 | 0 | 0 | 0 | 0 | 0 | 0 | 0 |
| 012 | BUNC | 1 | 0 | 0 | 0 | 0 | 0 | 0 | 0 | 1 | 0 | 0 | 0 | 0 | 0 | 0 | 0 | 0 | 0 | 0 | 1 |
| 013 | BOVF | 1 | 0 | 0 | 0 | 0 | 0 | 1 | 0 | 0 | 0 | 0 | 0 | 0 | 0 | 0 | 1 | 1 | 1 | 0 |
| 014 | EXC | 0 | 1 | 0 | 0 | 0 | 0 | 1 | 0 | 0 | 0 | 0 | 0 | 0 | 0 | 0 | 0 | 0 | 0 | 0 | 0 |
| 015 | BUNC | 1 | 0 | 0 | 1 | 0 | 0 | 0 | 0 | 1 | 0 | 0 | 0 | 0 | 0 | 0 | 1 | 1 | 0 |
| 016 | EXC | 0 | 1 | 0 | 1 | 0 | 0 | 1 | 0 | 0 | 0 | 1 | 0 | 0 | 0 | 0 | 0 | 0 | 0 | 0 |
| 017 | BUNC | 1 | 0 | 0 | 1 | 0 | 0 | 0 | 0 | 1 | 0 | 0 | 0 | 0 | 0 | 0 | 1 | 1 | 0 |

TABLE 7

| | | Option 2 Microprogram | | | | | | | | | | | | | | | | | | |
|---|---|---|---|---|---|---|---|---|---|---|---|---|---|---|---|---|---|---|---|---|
| | | PROM 0 | | | | PROM 1 | | | | PROM 2A | | | | PROM 3 | | | | PROM 4 | | |
| OCTAL | | OP | | W | R/W | CONTROL | | | | | | | | | | | | | | |
| ADDRESS | INSTR. | 00 | 01 | 02 | 03 | 04 | 05 | 06 | 07 | 08 | 09 | 10 | 11 | 12 | 13 | 14 | 15 | 16 | 17 | 18 | 19 |
| 100 | HLT | 0 | 0 | 0 | 0 | 0 | 0 | 0 | 0 | 0 | 0 | 0 | 0 | 0 | 0 | 0 | 0 | 0 | 0 | 0 | 0 |
| 101 | EXC | 0 | 1 | 1 | 0 | 0 | 0 | 1 | 0 | 0 | 0 | 0 | 1 | 1 | 0 | 1 | 0 | 0 | 0 | 0 | 0 |

TABLE 7-continued

| | | Option 2 Microprogram | | | | | | | | | | | | | | | | | | |
|---|---|---|---|---|---|---|---|---|---|---|---|---|---|---|---|---|---|---|---|---|
| | | PROM 0 | | | | PROM 1 | | | | PROM 2A | | | | PROM 3 | | | | PROM 4 | | |
| OCTAL | | OP | | W | R/W | | | | | | | CONTROL | | | | | | | | |
| ADDRESS | INSTR. | 00 | 01 | 02 | 03 | 04 | 05 | 06 | 07 | 08 | 09 | 10 | 11 | 12 | 13 | 14 | 15 | 16 | 17 | 18 | 19 |
| 102 | EXC | 0 | 1 | 1 | 0 | 0 | 0 | 0 | 0 | 0 | 0 | 0 | 0 | 1 | 0 | 0 | 0 | 0 | 0 | 0 | 0 |
| 103 | EXC | 0 | 1 | 0 | 0 | 0 | 0 | 1 | 0 | 0 | 0 | 0 | 0 | 1 | 0 | 1 | 0 | 0 | 0 | 0 | 0 |
| 104 | BRN OVF/UNF | 1 | 0 | 0 | 0 | 0 | 0 | 1 | 1 | 0 | 0 | 0 | 0 | 0 | 1 | 0 | 0 | 1 | 0 | 1 | 0 |
| 105 | EXC | 0 | 1 | 1 | 1 | 0 | 0 | 0 | 0 | 0 | 0 | 0 | 0 | 0 | 0 | 1 | 0 | 0 | 0 | 0 | 0 |
| 106 | EXC | 0 | 1 | 0 | 0 | 1 | 0 | 0 | 1 | 0 | 0 | 0 | 0 | 0 | 0 | 0 | 0 | 0 | 0 | 0 | 0 |
| 107 | BOPC | 1 | 0 | 0 | 0 | 0 | 0 | 0 | 0 | 1 | 0 | 0 | 0 | 0 | 1 | 0 | 0 | 0 | 0 | 0 | 0 |
| 110 | EXC | 0 | 1 | 0 | 0 | 0 | 1 | 0 | 0 | 0 | 0 | 0 | 0 | 0 | 1 | 0 | 0 | 0 | 0 | 0 | 0 |
| 111 | BUNC | 1 | 0 | 0 | 0 | 0 | 0 | 0 | 0 | 0 | 1 | 0 | 0 | 0 | 1 | 0 | 0 | 0 | 0 | 0 | 1 |
| 112 | BOVF | 1 | 0 | 0 | 0 | 0 | 0 | 1 | 0 | 0 | 0 | 0 | 0 | 0 | 1 | 0 | 0 | 1 | 1 | 0 | 1 |
| 113 | EXC | 0 | 1 | 0 | 0 | 0 | 0 | 1 | 0 | 0 | 0 | 0 | 0 | 0 | 0 | 0 | 0 | 0 | 0 | 0 | 0 |
| 114 | BUNC | 1 | 0 | 0 | 0 | 0 | 0 | 0 | 0 | 0 | 1 | 0 | 0 | 0 | 1 | 0 | 0 | 0 | 1 | 0 | 1 |
| 115 | EXC | 0 | 1 | 0 | 0 | 0 | 0 | 1 | 0 | 0 | 0 | 0 | 1 | 0 | 0 | 0 | 0 | 0 | 0 | 0 | 0 |
| 116 | BUNC | 1 | 0 | 0 | 0 | 0 | 0 | 0 | 0 | 0 | 1 | 0 | 0 | 0 | 1 | 0 | 0 | 0 | 1 | 0 | 1 |

Figure 19A:
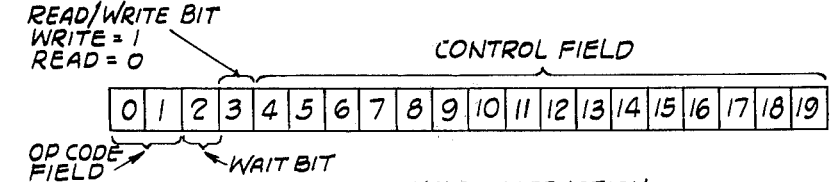

The program words stored in the memory 483 take the form of: (1) HALT instructions; (2) EXECUTE instructions; (3) BRANCH instructions. The general formats of the twenty bits for each instruction word are shown respectively in FIGS. 19a-19d. FIG. 19a shows the general format of the twenty-bit program words where bits 0, 1 define an OP CODE field which identifies the type of instruction the program word is. The only operation of the HALT instruction is to cause the special processor to cease operation, to increment the READ-ONLY MEMORY address register 481 and to clear the BUSY status. If the WAIT bit 2, is set, generating the CROM021 signal on the line 524, execution of the HALT instruction occurs only after the particular direct memory access transaction with the general processor 40 has been completed. Bit number 3 is a Read/Write bit which signifies whether the data on the bus 80 is to be read from, or written into, the storage sections of the processor 40. The remaining bits define a general control field.

Figure 19B:
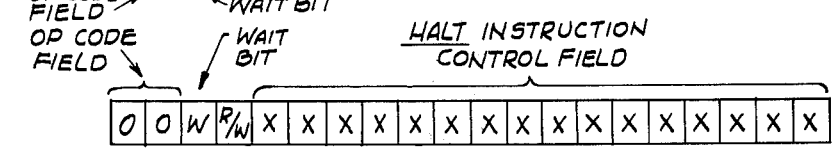

FIG. 19b shows the format for a HALT instruction. Bits 2, 3 are as previously described, and the bits 4-19 are meaningless. The bits 0, 1 are set to a 00 state to signify the HALT instruction, which generates the HALT0 signal on the line 534.

Figure 19C:
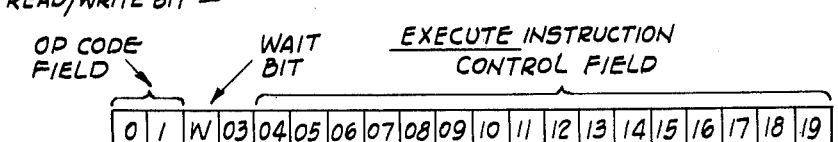

FIG. 19c shows the format for an EXECUTE instruction. The bits 0, 1 are set to a logic 01 state to signify that the program word is an EXECUTE instruction. The bits 2-19 are as previously described. Table 8 below sets forth the relationship between a particular one of the 4-19 control field bit positions in the EXECUTE instruction and the function which is effected by the particular setting of the particular bit position. Table 8 also defines whether a voltage pulse or a voltage level is generated in response to the particular setting of the bit position.

TABLE 8

| CONTROL FIELD BIT POSITION | FUNCTION | PULSE OR LEVEL |
|---|---|---|
| 04 | Count Array Counter | P |
| 05 | Load Scan Addrs Register | P |
| 06 | Load Accumulator | P |
| 07 | Count Operation Counter | P |
| 08 | Test Pulse | P |
| 09 | (Spare) | — |
| 10 | (Spare) | — |
| 11 | | L |
| 12 | Accum Input Sel A, Accum Input Sel B → A B Function / 0 0 AMIN / 0 1 ALU / 1 0 AMAX / 1 1 MEMORY | L |
| 13 | ALU Input Sel (0 = update, 1 = address) | L |
| 14 | DMA Array/Scan Addrs Sel (0 = Scan, 1 = Array) | L |
| 15 | (Spare) | — |
| 16 | (Spare) | — |
| 17 | (Spare) | — |
| 18 | (Spare) | — |
| 19 | (Spare) | — |

Figure 19D:
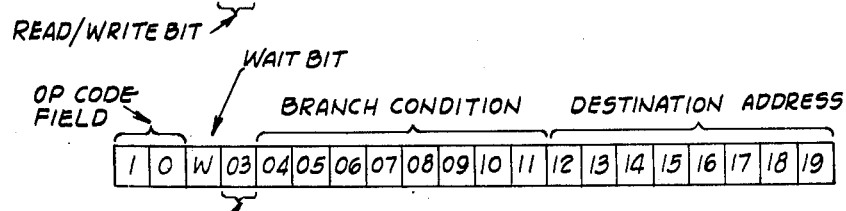

FIG. 19d shows the format for a BRANCH instruction. The bits 0, 1 are set 1, 0 states and the bits 2-3 are as previously described. The bits 4-11 define a branch condition, and the bits 12-19 define the location within the memory 483 to which control transfers if the branch condition is met.

Table 9 below sets forth the relationship between the branch condition bit positions of the BRANCH instruction and the condition which is tested for by the setting of the particular bit position. Table 9 also shows the MNEMONIC corresponding to each bit setting.

TABLE 9

| BRANCH CONDITION BIT POSITION | CONDITION | MNEMONIC |
|---|---|---|
| 04 | ACCUM MAX | BAMAX |
| 05 | ACCUM MIN | BAMIN |
| 06 | ALU OVERFLOW | BOVF |
| 07 | ALU UNDERFLOW | BUNF |
| 08 | OPERATION COMPLETE | BOPC |
| 09 | UNCONDITIONAL | BUNC |
| 10 | (SPARE) | |
| 11 | (SPARE) | — |

Referring now to FIG. 16a, the sequence control signal generator 490 is functionally shown in association with the control memory circuit 478.

The sequence control signal generator 490 (FIG. 16a) includes a run logic circuit 492, a microinstruction decoder 494, and a master timing chain 496. The run logic circuit 492 is shown in detail in FIG. 16f and includes a "run" flip-flop 498. The run flip-flop 498, when conditioned into a set state generates, the RUN1 signal on the line 453 to indicate that the special processor is excuting the back projection and update task. The run flip-flop 498 is conditioned into the set state by the INITIATE0 signal on the line 471 from the multiplexor channel control pulse generator 460. The run flip-flop 498 is reset by the STOP0 signal on the line 288 upon a plurality of conditions. One of the conditions which resets the run flip-flop 498 is the generation of the RESET0 signal on the line 474 from the multiplexor channel pulse generator 460. Another condition is the generation of the SCLR1 signal on a line 500 carrying the inverse of the SCLR0 signal on the line 433 from the bus 80. The run flip-flop 498 is also reset by the generation of a HALT PULSE0 signal on a line 502. The HALT PULSE0 signal on the line 502 is generated upon the simultaneous generation by the microinstruction decoder 594 of a HALT1 signal on a line 504 and by the generation of a EXECUTE PULSE1 signal on a line 506 by the master timing chain 496.

The sequence control signal generator 490 also includes a start pulse generator 508 (FIG. 16a) which is shown in detail in FIG. 16i. The start pulse generator includes a 50-nanosecond delay line 510 and a NAND gate 512. The delay line 510 and the gate 512 are responsive to the setting of the run flip-flop 498 via the RUN1 signal on the line 453. In response to the RUN1 signal, the gate 512 generates a START0 signal on a line 514. The START0 signal is of a 40-nanosecond duration due to connection of the delay line 510 as an input to the gate 512. Accordingly, the START0 pulse is of a standardized duration regardless of the duration during which the run flip-flop 498 is in the set state.

The START0 pulse on the line 514 from the start pulse generator 508 is transmitted to the master timing chamber 496 (FIG. 16j) for initiating a continuing timing sequence. The master timing chain 496 includes a start gate 516 having one of a pair of inputs coupled to the line 514 for receiving the START0 signal. Upon generation of the START0 signal, the gate 516 causes the LOAD CD signal to be generated on the line 486. This causes the data register 484 to be loaded with the addressed twenty-bit memory word from the memory 483.

The master timing chain 496 comprises generally a first series of delay lines coupled to the output of the gate 516 and a second series of delay lines coupled to the input of the gate 516 via a line 518. Propagation of the START0 pulse down the first series of delay lines eventually provides the EXECUTE PULSE1 signal on the line 506. As a feature the START0 signal is not allowed to unconditionally propagate down the first sequence of delay lines to invariably provide the EXECUTE PULSE1 signal. Instead, a pair of gates 520, 522 are serially connected to the output of the gate 516. The gates 520, 522 are respectively coupled to receive a CROM021. signal on a line 524 and a RESTART0 signal on a line 526. The CROM021 signal corresponds to setting of the WAIT bit 2 of a program word in the memory 483. This allows conditional halting of operations by the special procesor 42 until, for example, memory transactions with the general processor 40 have been completed. At that time, the RESTART0 signal on the line 526 is generated for restarting a pulse propagating down the first sequence of delay lines to provide the EXECUTE PULSE1 signal.

The second series of delay lines is provided to supply subsequent (to the START0 pulse) 40-nanosecond pulses propagating down the first series of delay lines. Each of the subsequent pulses are generated after each generation of one EXECUTE PULSE1 signal. To this end, a standardizing flip-flip 530 is provided at the beginning of the second series of delay lines. The standardizing flip-flop 530 has its DATA input terminal grounded and has its TRIGGER input terminal coupled to the LOAD CD signal on the line 486. Accordingly, the standardizing flip-flop 530 is reset or cleared upon each generation of the LOAD CD signal.

The set terminal of the standardizing flip-flop 53o is coupled to a gate 532 which is responsive to the EXECUTE PULSE1 signal on the line 506 and to a HALT0 signal on a line 534. The HALT0 signal on the line 534 is the inverse of the HALT1 signal on the line 504 (FIG. 16b) generated by the microinstruction decoder 494. The reset or clear terminal of the standardizing flip-flop 530 is coupled to a line 536 upon which a logic zero is generated upon (1) every occurrence of the RESET0 signal on the line 474, and (2) every occurrence of the SCLR1 signal on the line 500. Accordingly, the standardizing flip-flop 530 is cleared upon generation of every LOAD CD signal, and is set upon every EXECUTE PULSE1 signal.

Setting of the standardizing flip-flop 530 initiates a 40-microsecond pulse propagating down the second series of delay lines. This pulse eventually is input to the gate 516 via the line 518.

The microinstruction decoder 494 is shown in detail in FIG. 16b. It includes a plurality of gates 540-543 which are coupled to the first and second bits of the CD signals on the lines 487. These signals correspond to the first two bits of each program word and are encoded to define whether the particular program work is the HALT instruction, the EXECUTE instruction, or the BRANCH instruction. The gates 540-542, respectively, generate the HALT0 signal on the line 534, an EXECUTE0 signal on a line 544, and a BRANCH0 signal on a line 545.

The signal generator 490 also includes a microcontrol pulse generator 550 (FIG. 16a) which is shown in detail in FIG. 16c. The microcontrol pulse generator 550 includes a set of gates 551-555 which are enabled by the simultaneous occurrence of the EXECUTE0 pulse on the line 544 and the EXECUTE PULSE1 signal on the line 506. The gates 551-555 have their respective other inputs coupled to receive the fourth through eighth bits of the CD signals for respectively generating the COUNTOC0 signal on the line 398, the COUNT ARRAY CTR0 signal on the line 402, the LOAD SCAN ADDRS REG0 signal on the line 396, the LOAD ACCUM0 on the line 353 and a TEST PULSE0 signal on a line 556.

The signal generator 490 also includes a branch condition detector 560 (FIG. 16a) which is shown in detail in FIG. 16d. The branch condition detector 560 generates a BCM1 signal on a line 561 whenever (1) a program word has been decoded to define a branch instruction, and (2) the branch condition specified within the program word has been met. To this end, the branch condition detector 560 includes a plurality of gates 562–566. The gates 562–566 are respectively coupled to receive the bits 4–8 of the CD signals on the lines 486 and are respectively coupled to: the AMA 1 signal on the line 361; the AMIN1 signal on the line 362; the OVF1 signal on the line 383; the UNF1 signal on the line 382; and the OCOVF1 signal on the line 400. Accordingly, by enabling the proper one of the gates 562–566 via the respective bit of the CD signal (1) the maximum and minimum conditions of the updated elemental image signal value may be checked, (2) the overflow and underflow conditions of the updated elemental image signal may be checked, and (3) the condition of overflow of the operation counter 100 may be checked.

The signal generator 490 also includes a control read-only memory address control 570 (FIG. 16*a*) which is shown in detail in FIG. 16*e*. The address control 570 generates the LOAD CROM ADDRS REG0 signal on the line 482*a* and generates the COUNT CROM ADDRS REG0 signal on the line 482*b* which control operation of the memory address register 481 (FIG. 15).

The value of the memory address register 481 is incremented or counted upon generation of every EXECUTE PULSE1 signal on the line 506 whenever (1) a branch condition has not been met, as indicated by input of the signals BCM1 on the line 561 and the BRANCH0 signal on the line 545; (2) upon every HALT instruction, as indicated by the HALT0 signal on the line 534; and (3) upon execution of every program word, as indicated by the EXECUTE0 signal on the line 544 and the EXECUTE PULSE1 signal on the line 506. For all these conditions, the address control 570 generates the COUNT CROM ADDRS REG0 signal on the line 482*b*.

The memory address register 481 is loaded with a new address from the data selector 480 whenever (1) the MPX LOAD CROM ADDRS REG0 signal is generated on the line 467; (2) and whenever a program word has been decoded as a branch instruction and the branch condition has been met, as indicated by the BRANCH0 signal on the line 545 and by the BCM1 signal on the line 561 occurring concurrently with the EXECUTE PULSE1 signal on the line 506.

The signal generator 490 further includes a wait logic circuit 580 (FIG. 16*a*) which is shown in detail in FIG. 16*g*. The wait logic 580 includes a wait flip-flop 582 which, when set, generates a WAIT0 signal on a line 584. The WAIT0 signal indicates that a wait condition has been decoded from one of the program words, causing the special processor 42 to go into a wait mode of operation. To this end, the flip-flop 582 has its set terminal coupled to a gate 586 which (1) is responsive to the CROM021 signal on one of the lines 524 indicating that the wait bit of the program word has been set; and (2) is responsive to the LOAD CROM DATA REA1 signal on a line 588. The LOAD CROM DATA REA1 signal on the line 588 is the inverse of the LOAD CD signal on the line 486 (FIG. 16*f*). The gate 586 generates the SET REQ0 signal on the line 284 concurrently as it sets the wait flip-flop 582.

The wait flip-flop 582 is reset by generation of a READ RESTART1 signal via a line 590 or by generation of a WRITE RESTART1 signal via a line 592. The READ RESTART1 signal is generated upon the transmission of the ANS0 signal by the general processor 40 (as indicated by the ANS1 signal on a line 594 from the transceiver 262 of the DMA bus interface logic circuit 260) being concurrent with the occurrences of (1) the RUN1 signal on the line 453, (2) the S1 signal on the line 304, and (3) the wait flip-flop 582 being set, as indicated by a WAIT1 signal on a line 595.

The WRITE RESTART1 signal on the line 592 is generated upon the concurrent occurrences of (1) the EOT/1 signal on the line 332, the WRITE1 signal on he line 246 (i.e., the CD031 signal from the register 484 of FIG. 15); (2) the RUN1 signal on the line 455, (3) the S1 signal on the line 304, and the WAIT1 signal on the line 595.

The wait flip-flop 582 has its reset terminal coupled via the line 536 to be reset by the RESET0 signal on the line 474 (FIG. 16*f*), or by the SCLR1 signal on the line 500 (FIG. 16*f*). Accordingly, once the wait flip-flop 582 has been set indicating that the special processor is to suspend operations, it is not reset to allow resumption of operations until the direct memory access transaction has been completed.

The signal generator 490 also includes a restart pulse generator 600 (FIG. 16*a*) which is shown in detail in FIG. 16*h*. The generator 600 produces the RESTART0 pulse on the line 526. The structure of the pulse generator 600 is similar to the structure of the pulse generator 508, except that the pulse generator 600 is responsive to the WAIT0 signal on the line 584 for generating the 40-nonosecond pulse which eventually produces the EXECUTE PULSE1 signal.

Having described the specifics of the special processor 42, specific operation by the special processor 42 in carrying out the example of updating a 3 × 3 array is readily apparent from Table 10 below. The sequence tabulated in the Table 10 reflects (1) option 2 of the flow diagram of FIG. 6 and (2) the microprogram corresponding to the flow diagram of FIG. 18 and as defined in Table 7. In Table 10, the type of operation (i.e., by the general processor 40 or by the special processor 42) is respectively denoted by a "C" or "P" in the second column. The other columns show the contents of major registers within the special processor 42 at various times. The entries on a given line represent the contents and the conclusion of the specific operation.

TABLE 10

| LINE | * TYP | AR-RAY COUN-TER | SCAN ORIG REG | SCAN ADDR REG | SCAN EXT REG (numbers) to base 16) | Δ SCAN ADDR REG | ACCUMU-LATOR | MEM DATA REG | CROM ADDRS REG (to base 16) | OPER-ATION CTR (to base 10) | REMARKS |
|---|---|---|---|---|---|---|---|---|---|---|---|
| 1 | C | A(A1) | | | | | | | | | LOAD ARRAY CTR |
| 2 | C | A(A1) | SO1 | | | | | | | | LOAD SCAN ORIG |
| 3 | C | A(A1) | SO1 | A(V11) | 80 | | | | | | LOAD INIT SCAN ADR |
| 4 | C | A(A1) | SO1 | A(V11) | 80 | D1 | | | | | LOAD SCAN ADDR |
| 5 | C | A(A1) | SO1 | A(V11) | 80 | D1 | | | 41 | | LOAD CROM ADDRS |
| 6 | C | A(A1) | SO1 | A(V11) | 80 | D1 | | | 41 | 253 | LOAD OP CTR |
| 7 | C | A(A1) | SO1 | A(V11) | 80 | D1 | | | 41 | 253 | INITIATE (Row 1) |
| 8 | P | A(A1) | SO1 | A(V11) | 80 | D1 | A1 | A1 | 42 | 253 | ARRAY VAL⟶ACC |

TABLE 10-continued

| LINE | *TYP | ARRAY COUNTER | SCAN ORIG REG | SCAN ADDR REG | SCAN EXT REG (numbers to base 16) | Δ SCAN ADDR REG | ACCUMULATOR | MEM DATA REG | CROM ADDRS REG (to base 16) | OPERATION CTR (to base 10) | REMARKS |
|---|---|---|---|---|---|---|---|---|---|---|---|
| 9 | P | A(A1) | SO1 | A(V11) | 80 | D1 | A1 | V11 | 43 | 253 | SCAN VAL⟶MDR |
| 10 | P | A(A1) | SO1 | A(V11) | 80 | D1 | A1 + V11 | V11 | 44 | 253 | {ARRAY VAL + SCAN VAL⟶ACCUM |
| 11 | P | A(A1) | SO1 | A(V11) | 80 | D1 | A1 + V11 | V11 | 45 | 253 | TEST OVF/UNF |
| 12 | P | A(A1) | SO1 | A(V11) | 80 | D1 | A1 + V11 | V11 | 46 | 253 | WRITE ACC⟶MEM |
| 13 | P | A(A2) | SO1 | A(V11) | 80 | D1 | A1 + V11 | V11 | 47 | 254 | {INCREMENT ARRAY CTR AND OPER CTR |
| 14 | P | A(A2) | SO1 | A(V11) | 80 | D1 | A1 + V11 | V11 | 48 | 254 | TEST OP CTR |
| 15 | P | A(A2) | SO1 | A(V12) | EXT 11 | D1 | A1 + V11 | V11 | 49 | 254 | {CALCULATE NEXT SCAN ADDR |
| 16 | P | A(A2) | SO1 | A(V12) | EXT 11 | D1 | A1 + V11 | V11 | 41 | 254 | {RETURN TO UPDATE NEXT ARRAY POINT |
| 17 | P | A(A2) | SO1 | A(V12) | EXT 11 | D1 | A2 | A2 | 42 | 254 | ARRAY VAL⟶ACC |
| 18 | P | A(A2) | SO1 | A(V12) | EXT 11 | D1 | A2 | V12 | 43 | 254 | SCAN VAL⟶MDR |
| 19 | P | A(A2) | SO1 | A(V12) | EXT 11 | D1 | A2 + V12 | V12 | 44 | 254 | {ARRAY VAL + SCAN VAL⟶ACCUM |
| 20 | P | A(A2) | SO1 | A(V12) | EXT 11 | D1 | A2 + V12 | V12 | 4A | 254 | TEST OVF/UNF |
| 21 | P | A(A2) | SO1 | A(V12) | EXT 11 | D1 | A2 + V12 | V12 | 4D | 254 | OVF ? |
| 22 | P | A(A2) | SO1 | A(V12) | EXT 11 | D1 | MAX VALUE | V12 | 4E | 254 | SET ACC=MAX |
| 23 | P | A(A2) | SO1 | A(V12) | EXT 11 | D1 | MAX VALUE | V12 | 45 | 254 | GO TO WRITE |
| 24 | P | A(A2) | SO1 | A(V12) | EXT 11 | D1 | MAX VALUE | V12 | 46 | 254 | WRITE ACC⟶MEM |
| 25 | P | A(A3) | SO1 | A(V12) | EXT 11 | D1 | MAX VALUE | V12 | 47 | 255 | {INCREMENT ARRAY CTR AND OPER CTR |
| 26 | P | A(A3) | SO1 | A(V12) | EXT 11 | D1 | MAX VALUE | V12 | 48 | 255 | TEST OP CTR |
| 27 | P | A(A3) | SO1 | A(V13) | EXT 12 | D1 | MAX VALUE | V12 | 49 | 255 | {CALCULATE NEXT SCAN ADDR |
| 28 | P | A(A3) | SO1 | A(V13) | EXT 12 | D1 | MAX VALUE | V12 | 41 | 255 | {RETURN TO UPDATE NEXT ARRAY PT |
| 29 | P | A(A3) | SO1 | A(V13) | EXT 12 | D1 | A3 | A3 | 42 | 255 | ARRAY VAL⟶ACC |
| 30 | P | A(A3) | SO1 | A(V13) | EXT 12 | D1 | A3 | V13 | 43 | 255 | SCAN VAL⟶MDR |
| 31 | P | A(A3) | SO1 | A(V13) | EXT 12 | D1 | A3 + V13 | V13 | 44 | 255 | {ARRAY VAL + SCAN VAL⟶ACCUM |
| 32 | P | A(A3) | SO1 | A(V13) | EXT 12 | D1 | A3 + V13 | V13 | 4A | 255 | TEST OVF/UNF |
| 33 | P | A(A3) | SO1 | A(V13) | EXT 12 | D1 | A3 + V13 | V13 | 4B | 255 | OVF ? |
| 34 | P | A(A3) | SO1 | A(V13) | EXT 12 | D1 | MIN VALUE | V13 | 4F | 255 | SET ACC=MIN |
| 35 | P | A(A3) | SO1 | A(V13) | EXT 12 | D1 | MIN VALUE | V13 | 45 | 255 | GO TO WRITE |
| 36 | P | A(A3) | SO1 | A(V13) | EXT 12 | D1 | MIN VALUE | V13 | 46 | 255 | WRITE ACC⟶MEM |
| 37 | P | A(A4) | SO1 | A(V13) | EXT 12 | D1 | MIN VALUE | V13 | 47 | 256 | {INCREMENT ARRAY CTR AND OPER CTR |
| 38 | P | A(A4) | SO1 | A(V13) | EXT 12 | D1 | MIN VALUE | V13 | 40 | 256 | TEST OP CTR |
| 39 | P | A(A4) | SO1 | A(V13) | EXT 12 | D1 | MIN VALUE | V13 | 41 | 256 | HALT, First Row Compl. |
| 40 | C | A(A4) | SO1 | A(V13) | EXT 12 | D1 | MIN VALUE | V13 | 41 | 256 | SENSE STATUS (not busy) |
| 41 | C | A(A4) | SO1 | A(V14) | 80 | D1 | MIN VALUE | V13 | 41 | 256 | LOAD INIT SCAN ADR |
| 42 | C | A(A4) | SO1 | A(V14) | 80 | D1 | MIN VALUE | V13 | 41 | 253 | LOAD OP CTR |
| 43 | C | A(A4) | SO1 | A(V14) | 80 | D1 | MIN VALUE | V13 | 41 | 253 | INITIATE (Row 2) |
| 44 | P | A(A4) | SO1 | A(V14) | 80 | D1 | A4 | A4 | 42 | 253 | ARRAY VAL⟶ACC |

(Remainder of Row 2 back projection as per steps 9 through 39 above).
(Row 3 back projection started after not-busy status sensed and $A(S\theta_{17})$ loaded into scan address register plus operation counter preset to $253_{10}$.)
*C - main computer operation.
P - special processor operation.

A(Ai) represents the array Address of the ith point of the array A; SO1 represents the scan origin 77 corresponding to view number one; A(Vlj) represents the scan address of the jth point in the SCAN ($\theta$1) view stored in the scan storage section 58; EXT 1j represents the extension bits of the A(Vlj) scan address after having been incremented by Delta; D1 represents the value of DELTA for the $\theta$ view; Ai represents the incremental image value at the ith point; and Vlj represents the value in the scan storage section at the address location A(Vlj).

Table 10 shows back projection corresponding to a scan acquired by an angle of θ1. In order to show all possibilities, Table 10 is based on (1) the result of array update of the first point, A1, resulting in no adder 366 overflow or underflow; (2) the update of point A2 resulting in an overflow; and (3) the update of point A3 resulting in an underflow.

The termination of updating the first row of the array A is shown, as are the actions necessary to be taken by the general processor 40 for setting up the initiation of the row 2 back projection. As is readily apparent there are considerably fewer operations required by the general processor 40 to initiate row back projections after the first row. This is a feature attributed to the design of the unit 24, as many of the parameters are stored within the special processor 42 and remain constant for a given angle of view θ.

In the described example, the data which is transferred between the processors 40, 42 is transferred with a predetermined alignment between data paths. This alignment is given in Table 11.

TABLE 11

| | | Alignment of Data Paths | | | |
|---|---|---|---|---|---|
| Δ SCAN ADDR | BYTE ADDRESS (CONSOLE) | DATA (ACCUM TO MEMORY) | ARRAY ADDRESS | INTER-POLATED SCAN ADDRESS | DMA BUS LINES |
| | | | ARC 001 | SO 001 | DMX 120 |
| | | | ARC 011 | SO 011 | DMX 130 |
| | | | ARC 021 | SO 021 | DMX 140 |
| | | | ARC 031 | | |
| | | | | SO 031 | DMX 150 |
| | BA 00 | A 001 | ARC 041 | SO 041 | DMA 000 |
| | BA 01 | A 011 | ARC 051 | SO 051 | DMA 010 |
| | BA 02 | A 021 | ARC 061 | SO 061 | DMA 020 |
| | BA 03 | A 031 | ARC 071 | | |
| | | | | SA 001 | DMA 030 |
| | BA 04 | A 041 | ARC 081 | SA 011 | DMA 040 |
| | BA 05 | A 051 | ARC 091 | SA 021 | DMA 050 |
| | BA 06 | A 061 | ARC 101 | SA 031 | DMA 060 |
| | BA 07 | A 071 | ARC 111 | | |
| | | | | SA 041 | DMA 070 |
| | BA 08 | A 081 | ARC 121 | SA 051 | DMA 080 |
| (Δ SIGN) | BA 09 | A 091 | ARC 131 | SA 061 | DMA 090 |
| AΔ001 | BA 10 | A 101 | ARC 141 | SA 071 | DMA 100 |
| | BA 11 | A 111 | ARC 151 | | |
| Δ001 | | | | SA 081 | DMA 110 |
| Δ011 | BA 12 | A 121 | ARC 161* | SA 091 | DMA 120 |
| Δ021 | BA 13 | A 131 | ARC 171* | SA 101 | DMA 130 |
| Δ031 | BA 14 | A 141 | ARC 181* | SA 111 | DMA 140 |
| | BA 15 | A 151 | | | |
| ΔEXT 001 | | | | | DMA 150 |
| ΔEXT 011 | | | | | DMA 160 |
| ΔEXT 021 | | | | | DMA 170 |
| ΔEXT 031 | | | | | |
| ΔEXT 041 | | | | | |
| ΔEXT 051 | | | | | |
| ΔEXT 061 | | | | | |
| ΔEXT 071 | | | | | |

*ARC 161, 171, 181 set to "0" when array counter loaded from MPX channel.

For example, bit 14 of the DMA signal corresponds to bit 11 of the SA signal when the scan address is being transmitted to the general processor 40. Bit 18 of the ARC signal corresponds to bit 14 of the DMA signal when an array address is being transmitted to the processor 40.

Although a preferred embodiment has been described in a fair amount of detail, it is understood that the description is only by way of example, as other changes are readily apparent. For example, referring to the flow diagram of FIG. 6, the function of block 204 may readily be executed concurrently with execution of the blocks 197, 198 merely by changing the micro program in the memory 483. This and other such changes are understood not to depart from the spirit and the scope of the invention as hereinafter claimed.

What is claimed is:

1. A transverse section tomography system for providing a reconstructed image of a planar section of a subject, comprising:

a. a movably supported radiation detector for detecting radiation which has passed through the planar section of the subject and for generating a sequence of scan data signals indicative of the intensity of the radiation after it has passed through the subject, said scan data signals being generated at predetermined orientations and positions whereby detection of the radiation at a given orientation and position defines a scan element and detection of the radiation at all predetermined orientations and positions defines a scan cycle; and, b. data processing means responsive to the sequence of scan data signals for generating a set of repeatedly updated, elemental image signals characterizing structure of the planar section of the subject, said data processing means including:

i. input storage means for storing the respective scan data signals in particular input storage locations;

ii. filter processing means coupled to the input storage for successively retrieving the scan data signals from the input storage locations of the filter processing means and for producing filtered scan signals from the retrieved scan data signals which are representative of the reconstructed image contribution of each of the scan data signals;

iii. scan storage means for retrievably storing the filtered scan signals in scan storage locations corresponding to scan elements occurring at predetermined orientations during the scan cycle;

iv. array storage means for storing as they are generated, elemental image signals which are to be repeatedly updated; the elemental image signals being stored in array storage locations coordinated with a preselected array of points of said planar section;

v. an array storage address calculator for addressing a selected array storage location containing the elemental image signal corresponding to a selected one of said preselected points of the planar section;

vi. a scan storage address calculator for addressing the scan storage location containing the filtered scan signal corresponding to a given scan element which resulted in the detection of radiation sufficiently near said selected point to contribute to the reconstruction of the image at said selected point;

vii. updating means for combining the addressed filtered scan signal with the addressed elemental image signal to provide one of the updated, elemental image signals; and, viii. a controller coupled to the storage address calculators for operating them concurrently.

2. The scanning system according to claim 1 and further including addressing means operable concurrently with at least one of said address calculators for writing said one elemental image signal into one of the array storage locations.

3. The scanning system according to claim 2 wherein the addressing means is operated to write said one elemental image signal into the array storage location corresponding to said selected point.

4. The scanning system according to claim 1 wherein said controller includes a memory unit for storing a sequence of program words which characterize at least partial operation of the data processing means.

5. In a transverse section tomography system for providing a reconstructed image of a planar section of a subject and having a radiation detector for detecting radiation which has passed through the planar section of the subject and for generating a sequence of scan data signals indicative of the intensity of the radiation after it has passed at predetermined orientations and positions through the subject, whereby detection of the radiation at a given orientation defines a scan element and detection of the radiation through all predetermined orientations and positions defines a scan cycle, and further having data processing means responsive to the sequence of scan data signals for generating repeatedly updated elemental image signals which eventually characterize structure of the planar section of the subject, the improvement wherein the data processing means comprises:

a. input storage means for storing the respective scan data signals in particular input storage locations;

b. filter processing means coupled to the input storage for successively retrieving the scan data signals from the input storage locations and for producing therefrom filtered scan signals representative of the reconstructed image contribution of each of the scan data signals;

c. scan storage means for retrievably storing the filtered scan signals in scan storage locations corresponding to scan elements occurring at predetermined orientations during the scan cycle;

d. array storage means for storing as they are generated, the elemental image signals which are to be updated; the storing being in array storage locations coordinated with a preselected array of points of said planar section;

e. an array storage address calculator for addressing a selected array storage location containing the elemental image signal corresponding to a selected one of said preselected points of the planar section;

f. a scan storage address calculator for addressing the scan storage location containing the filtered scan signal corresponding to a given scan element which resulted in the detection of radiation sufficiently near said selected point to contribute the reconstruction of the image at said selected point;

g. updating means for combining the addressed filtered scan signal with the addressed elemental image signal to provide the updated, elemental image signal; and, h. addressing means coupled to the updating means and operable concurrently with at least one of said address calculators for writing said updated, elemental image signal into a location in said array storage.

6. The improved tomography system according to claim 5 wherein the addressing means is configured to write said updated, elemental image signal into the array storage location corresponding to said selected point.

7. The improved tomography system according to claim 5 and further including control means coupled to the address calculators for operating them concurrently.

8. The improved tomography system according to claim 7 wherein the control means includes a memory unit for storing a sequence of program words which characterize at least partial operation of the data processing means.

9. A transverse section tomographic scanning system for providing a reconstructed image of a planar section of a subject, comprising:

a. a scanner for directing at least one beam of X-radiation of relatively small cross-section through a plane of the subject from a succession of predetermined orientations and positions coplanar with said plane and for generating a sequence of scan data signals indicative of the intensity of the beam of radiation after it has passed through the subject, whereby passing the beam through the subject at a given orientation and position defines a scan element and passing the beams through all predetermined orientations and positions defines a scan cycle; and, b. data processing means responsive to the sequence of scan data signals for generating a set of repeatedly updated, elemental image signals characterizing structure of the planar section of the subject, said data processing means including:

i. input storage means for storing the respective scan data signals in particular input storage locations;

ii. filter processing means coupled to the input storage for successively retrieving the scan data signals from the input storage locations, the filter processing means producing filtered scan signals from the retrieved scan data signals which are representative of the reconstructed image contribution of each of the scan data signals;

iii. scan storage means for retrievably storing the filtered scan signals in scan storage locations corresponding to scan elements occurring at predetermined orientations during the scan cycle;
iv. array storage means for storing, as they are generated, the elemental image signals which are to be repeatedly updated; the storing being in array storage locations coordinated with a preselected array of points of said planar section;
v. an array storage address calculator for addressing a selected array storage location containing the elemental image signal corresponding to a selected one of said preselected points of the planar section;
vi. a scan storage address calculator for addressing the scan storage location containing the filtered scan signal corresponding to a given scan element which resulted in the passage of radiation sufficiently near said selected point to contribute to the reconstruction of the image at said selected point;
vii. updating means for combining the addressed filtered scan signal with the addressed elemental image signal to provide an updated elemental image signal; and,
viii. a controller coupled to the scan storage address calculator and the array storage address calculator for operating them concurrently.

10. The scanning system according to claim 9 and further including addressing means operable concurrently with at least one of said address calculators for writing said updated, elemental image signal into the array storage location corresponding to said selected point.

11. The scanning system according to claim 9 wherein the controller includes a memory unit for storing a sequence of program words which characterize at least in part the operations of the data processing means.

12. A transverse section tomographic scanning system for providing a reconstructed image of a planar section of a subject, comprising:
   a. a scanner for directing at least one beam of X-radiation of relatively small cross-section through a plane of the subject from a succession of predetermined orientations and positions coplanar with said plane and for generating a sequence of scan data signals indicative of the intensity of the beam of radiation after it has passed through the subject, whereby passing the beam through the subject at a given orientation and position defines a scan element and passing the beams through all predetermined orientations and positions defines a scan cycle; and,
   b. data processing means responsive to the sequence of scan data signals for generating repeatedly updated, elemental image signals characterizing structure of the planar section of the subject, said data processing means including:
      i. input storage means for storing the respective scan data signals in particular input storage locations;
      ii. filter processing means coupled to the input storage for successively retrieving the scan data signals from the input storage locations, the filter processing means producing filtered scan signals from the retrieved scan data signals which are representative of the reconstructed image contribution of each of the scan data signals;
      iii. scan storage for retrievably storing the filtered scan signals in scan storage locations corresponding to scan elements occurring at predetermined orientations during the scan cycle;
      iv. array storage means for operably storing, as the are generated and for operably providing, the elemental image signals which are to be repeatedly updated; the storing being in array storage locations coordinated with a preselected array of points of said planar section;
      v. an array storage address calculator for addressing a selected array storage location containing the elemental image signal corresponding to a selected one of said preselected points of the planar section;
      vi. a scan storage address calculator for addressing the scan storage location containing the filtered scan signal corresponding to a given scan element which resulted in the passage of radiation sufficiently near said selected point to contribute to the reconstruction of the image at said selected point;
      vii. updating means for combining the addressed filtered scan signal with the addressed elemental image signal to provide the updated elemental image signal; and,
      viii. addressing means coupled to the updating means and operable concurrently with at least one of said address calculators for operating the array storage means.

13. The scanning system according to claim 12 wherein the addressing means is structured to write said updated, elemental image signal into the array storage location corresponding to said one point.

14. A transverse section tomographic scanning system for providing a reconstructed image of a planar section of a subject, comprising:
   a. a scanner for directing at least one beam of X-radiation of relatively small cross-section through a plane of the subject from a succession of positions coplanar with said plane about the subject, the scanner including:
      i. generator means for axially producing the at least one beam in said plane;
      ii. detector means for detecting the at least one beam and producing scan data signals indicative of the intensity of the beam of radiation after the beam has passed at predetermined scan orientations and positions through the subject; and,
      iii. support means for relatively moving the generator means and the detector means about the subject for passing the beam through the subject at said predetermined orientations and positions, whereby the passage of the beam through a given orientation and positions defines a scan element which produces the associated scan data signal, and passing the beam through all said predetermined orientations and positions defines a scan cycle;
   b. a first data processor having:
      i. input storage means for storing the respective scan data signals in particular input storage locations;
      ii. filter processing means coupled to the input storage for successively retrieving the scan data signals and for producing therefrom filtered scan signals representative of the contribution of each of the scan data signals towards reconstructing said image;

iii. scan storage means for retrievably storing the filtered scan signals in groups of scan storage locations respectively corresponding to each scan element occurring at predetermined orientations during the scan cycle; and, iv. array storage means for storing, as they are produced, elemental image signals in array storage locations;

c. a second data processor operated in association with said first data processor and responsive to said filtered scan signals for producing elemental image signals, said elemental image signals each being successively updated to eventually represent the density at each of a preselected array of points of said planar section, the second data processor including:

i. an array storage address calculator for generating an array storage address signal which specifies the array storage location containing a particular elemental image signal corresponding to a selected point of the planar section;

ii. a scan storage address calculator for generating a scan storage address signal for specifying the scan storage location containing a particular filtered scan signal corresponding to a given scan element which resulted in the passage of an X-ray beam sufficiently near said selected point to contribute to the reconstruction of the image at said selected point;

iii. scan addressing means responsive to said scan storage address signals for addressing the scan storage means to provide said particular filtered scan signal;

iv. array addressing means responsive to said array storage address signals for addressing the array storage means to provide said particular elemental image signals;

v. updating means for combining the particular filtered scan signal with the particular elemental image signal to provide the updated, elemental image signal;

vi. said array addressing means also being responsive to said updated, elemental image signal for writing it into a selected array storage location; and, vii. a controller coupled to the scan storage address calculator and to the array storage address calculator for operating them concurrently.

15. The scanning system according to claim 14 wherein said array addressing means is structured to write said updated, elemental image signal into the array storage location corresponding to said selected point.

16. The scanning system according to claim 14 wherein the controller includes a programmable memory unit for storing a sequence of program words which characterize operation of the second data processor.

17. A transverse section tomographic scanning system for providing a reconstructed image of a planar section of a subject, comprising:

a. a scanner for directing at least one beam of X-radiation of relatively small cross-section through a plane of the subject from a succession of positions coplanar with said plane about the subject, the scanner including:

i. generator means for axially producing the at least one beam in said plane;

ii. detector means for detecting the at least one beam and producing scan data signals indicative of the intensity of the beam of radiation after the beam has passed at predetermined scan orientations and positions through the subject; and, iii. support means for relatively moving the generator means and the detector means about the subject for passing the beam through the subject at said predetermined orientations and positions, whereby the passage of the beam through a given orientation and position defines a scan element which produces the associated scan data signal, and passing the beam through all said predetermined orientations and positions defines a scan cycle;

b. a first data processor having:

i. input storage means for storing the respective scan data signals in particular input storage locations;

ii. filter processing means coupled to the input storage for successively retrieving the scan data signals and for producing therefrom filtered scan signals representative of the contribution of each of the scan data signals towards reconstructing said image;

iii. scan storage means for retrievably storing the filtered scan signals in groups of scan storage locations respectively corresponding to each scan element occurring at predetermined orientations during the scan cycle; and, iv. array storage means for storing, as they are produced, elemental image signals in array storage locations;

c. a second data processor operated in association with said first data processor and responsive to said filtered scan signals for producing elemental image signals, said elemental image signals each being successively updated to eventually represent the density at each of a preselected array of points of said planar section, the second data processor including:

i. an array storage address calculator for generating an array storage address signal which specifies the array storage location containing a particular elemental image signal corresponding to a selected point of the planar section;

ii. a scan storage address calculator for generating a scan storage address signal for specifying the scan storage location containing a particular filtered scan signal corresponding to a given scan element which resulted in the passage of an X-ray beam sufficiently near said selected point to contribute to the reconstruction of the image at said selected point;

iii. scan addressing means responsive to said scan storage address signals for addressing the scan storage means to provide said particular filtered scan signal;

iv. array addressing means responsive to said array storage address signals for addressing the array storage means to provide said particular elemental image signals;

v. updating means for combining the particular filtered scan signal with the particular elemental image signal to provide the updated, elemental image signal;

vi. said array addressing means also being responsive to said updated, elemental image signal for writing it into a selected array storage location;

vii. a controller for operating said array addressing means concurrently with at least one of said address calculators.

18. The scanning system according to claim 17 wherein the array addressing means is structured to write said updated, elemental image signal into the array storage location corresponding to said selected point.

19. The scanning system according to claim 17 wherein the controller includes a memory unit for storing a sequence of program words which characterize operation of the second data processor.

20. The scanning system according to claim 17 wherein the updating means includes:
   a. an arithmetic unit for performing arithmetic operations on values of the filtered scan signal and on the elemental image signal; and,
   b. a detector coupled to the arithmetic unit for detecting, during the arithmetic operations on the filtered scan and the elemental image signals, simultaneously whether overflow or underflow conditions have occurred.

21. The scanning system according to claim 17 wherein said first data processor includes a control unit operable concurrently with said controller, whereby said data processor can operate concurrently with said second data processor.

22. The scanning system according to claim 21 wherein there is direct memory access by the second data processor to the storage means of the first data processor and said second data processor comprises contention circuitry for assigning control of memory access to either the first data processor or to the second data processor.

23. The scanning system according to claim 22 wherein the contention circuitry is structured to assign priority to the second data processor whenever both data processors seek memory access to the storage means.

24. In a tomographic scanning system for providing a reconstructed image of a planar section of a subject which is relatively scanned from a plurality of predetermined scan orientations and positions by X-radiation, a method of providing elemental image signals which are successively updated and stored to represent the reconstructed image, comprising the steps of:
   a. defining at least one beam of X-radiation having a relatively small cross-section;
   b. directing the at least one beam through a plane of the subject from a succession of orientations and positions coplanar with the plane, whereby passing the beam through a given orientation and position defines a scan element and passing the beam through all the predetermined orientations and positions defines a scan cycle;
   c. detecting the intensity of the beam after it passes through the subject at the succession of positions;
   d. generating a sequence of scan data signals representative of the intensity of the detected radiation corresponding to each scan element;
   e. storing the respective scan data signals in input storage locations;
   f. filtering the scan data signals to provide filtered scan signals representative of the contribution of each of the scan data signals towards reconstructing said image;
   g. retrievably storing the filtered scan signals in scan storage locations corresponding to scan elements occurring at respective predetermined orientations during the scan cycle;
   h. defining a preselected array of points corresponding to positions in said planar section;
   i. storing, as they are produced, in array storage locations elemental image signals which are to be repeatedly updated;
   j. calculating the address of the array storage location containing the elemental image signal corresponding to a selected one of said point;
   k. concurrently with said step of calculating the address of said elemental image signal, calculating the address of the scan storage location containing the filtered scan signal corresponding to a particular scan element which resulted in the passage of a beam of X-radiation sufficiently close to said selected point to contribute to the reconstruction of the image at said selected point;
   l. retrieving the addressed filtered scan signal and the addressed elemental image signal;
   m. combining the addressed filter scan signal with the addressed elemental image signal to provide an updated, elemental image signal; and,
   n. writing the updated, elemental image signal into one of said array storage locations.

25. The method according to claim 24 wherein said step of writing comprises the step of writing the updated, elemental image signal to the array storage locations corresponding to said selected point.

26. In a tomographic scanning system for providing a reconstructed image of a planar section of a subject which is relatively scanned from a plurality of predetermined scan orientations and positions by X-radiation, a method of providing elemental image signals which are successively updated and stored to represent the reconstructed image, comprising the steps of:
   a. defining at least one beam of X-radiation having a relative small cross-section;
   b. directing the at least one beam through a plane of the subject from a succession of orientations and positions coplanar with the plane, whereby passing the beam through a given orientation and position defines a scan element and passing the beam through all the predetermined orientations and positions defines a scan cycle;
   c. detecting the intensity of the beam after it passes through the subjecft at the succession of positions;
   d. generating a sequence of scan data signals representative of the intensity of the detected radiation corresponding to each scan element;
   e. storing the respective scan data signals in input storage locations;
   f. filtering the scan data signals to provide filtered scan signals representative of the contribution of each of the scan data signals towards reconstructing said image; g. retrievably storing the filtered scan signals in scan storage locations corresponding to scan elements occurring at respective predetermined orientations during the scan cycle;
   h. defining a preselected array of points corresponding to positions in said planar section;
   i. storing, as they are produced, in array storage locations elemental image signals which are to be repeatedly updated;

j. calculating the address of the array storage locations containing the elemental image signal corresponding to a selected one of said points;

k. calculating the address of the scan storage locations containing the filtered scan signal corresponding to a particuar scan element which resulted in the passage of a beam of X-radiation sufficiently close to said selected point to contribute to the reconstruction of the image at said selected point;

retrieving the addressed filter scan signal and the addressed elemental image signal;

m. combining the addressed filtered scan signal with the addressed elemental image signal to provide an updated, elemental image signal; and, n. concurrently with said step of calculating the address of said filtered scan signal, the step of writing the updated, elemental image signal into one of said array storage locations.

27. The method according to claim 26 wherein said step of writing comprises writing the updated, elemental image signal into the array storage locations corresponding to said selected point.

* * * * *

UNITED STATES PATENT AND TRADEMARK OFFICE
CERTIFICATE OF CORRECTION

PATENT NO. : 4,044,240

DATED : August 23, 1977

INVENTOR(S) : Jerome R. Cox, Jr., et al

It is certified that error appears in the above-identified patent and that said Letters Patent are hereby corrected as shown below:

[75] Correct name of one of the inventors to --Jerome R. Cox, Jr.--.

Column 1, line 39, "crosssectional" should be --cross-sectional--; line 57, "rectinlinear" should be --rectilinear--; line 68, "give" should be --given--.

Column 2, line 22, "oribital" should be --orbital--; line 24, "oribital" should be --orbital--.

Column 4, line 6, before "The" begin new paragraph; line 27, "scaner" should be --scanner--.

Column 8, line 55, "operation" should be --operations--.

Column 12, after line 16, sub-title "THE DATA PROCESSING UNIT 14" should be --THE DATA PROCESSING UNIT 24--.

Column 13, line 24, "filted" should be --filtered--; line 25, "angle" should be --angles--.

Column 14, line 12, "paralleogram" should be --parallelogram--.

Column 16, line 31, after sin ")" should be --(--.

Column 17, line 6, "if" should be --of--; line 53, "indicated" should be --indicate--.

Column 18, line 36, "arrow" should be --array--.

Column 19, line 66, "status" should be --STATUS--.

Column 25, line 45, after "updated." begin new paragraph.

Column 26, line 5, "storaged" should be --stored--; line 8, after "the" delete --the--, second occurrence; line 65, after "elemental" insert --image--.

Column 27, line 50, after "HALFWORD" delete --and--; line 60, after "commercially" delete --)--.

Column 29, line 51, after "on" insert --a--.

Column 31, line 35, "slignal" should be --signal--; line 48, delete "This" first occurrence, substitute --To--.

Column 33, line 14, change "Cl)" to --(1); line 17, change "C2)" to --(2)--.

UNITED STATES PATENT AND TRADEMARK OFFICE
CERTIFICATE OF CORRECTION

PATENT NO. : 4,044,240

DATED : August 23, 1977

INVENTOR(S) : Jerome R. Cox, Jr., et al

It is certified that error appears in the above-identified patent and that said Letters Patent are hereby corrected as shown below:

Column 35, line 17, change "ALVO31" to --ALU031--; line 34, after "the" and before " △ " delete --.--.
Column 36, line 7, after "LOAD" insert --INIT--.
Column 38, line 50, "load" should be --LOAD--.
Column 39, line 2, "carring" should be --carrying--.
Column 40, line 20, after "signals" first occurrence and before "." insert -- ) --.
Column 43, line 10, "excuting" should be --executing--.
Column 44, line 19, change "53o" to --530--; line 42, "work" should be --word--.
Column 45, line 4, "AMA 1" should be --AMAX1--; line 55, "REA1" should be --REG1--.
Column 46, line 1, "REA1" should be --REG1--; line 19, "he" should be --the--.
Column 48, line 64, "Delta" should be --DELTA--.
Column 54, line 5, "the" should be --they--; line 56, "positions" should be --position--.

UNITED STATES PATENT AND TRADEMARK OFFICE
CERTIFICATE OF CORRECTION

PATENT NO. : 4,044,240
DATED : August 23, 1977
INVENTOR(S) : Jerome R. Cox, Jr., et al It is certified that error appears in the above-identified patent and that said Letters Patent are hereby corrected as shown below:

Column 58, line 51, "subjecft" should be --subject--; line 60, new paragraph after "imager;".
Column 59, line 4, "locations" should be --location--; line 11, before "retrieving" insert --1.--; same line, "filter" should be --filtered--.
Column 60, line 10, "locations" should be --location--.

Signed and Sealed this

Twenty-third Day of May 1978

[SEAL]

Attest:

RUTH C. MASON
Attesting Officer

LUTRELLE F. PARKER
Acting Commissioner of Patents and Trademarks